(12) United States Patent
Makriyannis et al.

(10) Patent No.: US 9,102,622 B2
(45) Date of Patent: Aug. 11, 2015

(54) FATTY ACID AMIDE HYDROLASE INHIBITORS

(75) Inventors: Alexandros Makriyannis, Watertown, MA (US); Spyridon P. Nikas, Waltham, MA (US); Shakiru O. Alapafuja, Lynn, MA (US); Vidyanand G. Shukla, Boston, MA (US)

(73) Assignee: University of Connecticut, Farmington, CT (US)

( * ) Notice: Subject to any disclaimer, the term of this patent is extended or adjusted under 35 U.S.C. 154(b) by 1315 days.

(21) Appl. No.: 12/309,661

(22) PCT Filed: Jul. 27, 2007

(86) PCT No.: PCT/US2007/016953

§ 371 (c)(1),
(2), (4) Date: Aug. 5, 2009

(87) PCT Pub. No.: WO2008/013963

PCT Pub. Date: Jan. 31, 2008

(65) Prior Publication Data

US 2009/0306016 A1    Dec. 10, 2009

Related U.S. Application Data

(60) Provisional application No. 60/833,937, filed on Jul. 28, 2006.

(51) Int. Cl.

| C07D 213/75 | (2006.01) |
|---|---|
| C07C 17/16 | (2006.01) |
| C07C 45/41 | (2006.01) |
| C07D 263/56 | (2006.01) |
| C07D 271/10 | (2006.01) |
| C07D 275/06 | (2006.01) |
| C07D 277/64 | (2006.01) |
| C07C 45/44 | (2006.01) |
| C07C 45/45 | (2006.01) |
| C07C 45/67 | (2006.01) |
| C07C 49/233 | (2006.01) |
| C07C 49/255 | (2006.01) |
| C07C 49/84 | (2006.01) |
| C07C 69/712 | (2006.01) |
| C07C 69/738 | (2006.01) |
| C07C 271/12 | (2006.01) |
| C07C 271/14 | (2006.01) |

(Continued)

(52) U.S. Cl.
CPC .............. *C07D 213/75* (2013.01); *C07C 17/16* (2013.01); *C07C 45/41* (2013.01); *C07C 45/44* (2013.01); *C07C 45/45* (2013.01); *C07C 45/673* (2013.01); *C07C 49/233* (2013.01); *C07C 49/255* (2013.01); *C07C 49/84* (2013.01); *C07C 69/712* (2013.01); *C07C 69/738* (2013.01); *C07C 271/12* (2013.01); *C07C 271/14* (2013.01); *C07C 271/16* (2013.01); *C07C 271/24* (2013.01); *C07C 271/38* (2013.01); *C07C 271/58* (2013.01); *C07C 309/68* (2013.01); *C07C 309/81* (2013.01); *C07C 309/82* (2013.01); *C07D 213/30* (2013.01); *C07D 213/40* (2013.01); *C07D 213/50* (2013.01); *C07D 263/56* (2013.01); *C07D 271/10* (2013.01); *C07D 275/06* (2013.01); *C07D 277/64* (2013.01); *C07C 2101/14* (2013.01); *C07C 2103/74* (2013.01)

(58) Field of Classification Search
None
See application file for complete search history.

(56) References Cited

U.S. PATENT DOCUMENTS 4,616,026 A * 10/1986 Richardson et al. .......... 514/381
2005/0101542 A1 * 5/2005 Piomelli et al. ............... 514/23

FOREIGN PATENT DOCUMENTS

EP    0117100    *   8/1984
EP    0271731 A2 * 11/1987
(Continued)

OTHER PUBLICATIONS

Eto et al, Chemical & Pharmaceutical Bulletin (2001), 49(2),pp. 173-182.*

(Continued)

*Primary Examiner* — Zinna Northington Davis
(74) *Attorney, Agent, or Firm* — Alix, Yale & Ristas, LLP

(57) ABSTRACT

Disclosed are compounds of formula R—X—Y that may be used to inhibit the action of fatty acid amide hydrolase (FAAH). Inhibition of fatty acid amide hydrolase (FAAH) will slow the normal degradation and inactivation of endogenous cannabinoid ligands by FAAH hydrolysis and allow higher levels of those endogenous cannabinergic ligands to remain present. These higher levels of endocannabinoid ligands provide increased stimulation of the cannabinoid CB1 and CB2 receptors and produce physiological effects related to the activation of the cannabinoid receptors. They will also enhance the effects of other exogenous cannabinergic ligands and allow them to produce their effects at lower concentrations as compared to systems in which fatty acid amide hydrolase (FAAH) action is hot inhibited. Thus, a compound that inhibits the inactivation of endogenous cannabinoid ligands by fatty acid amide hydrolase (FAAH) may increase the levels of endocannabinoids and, thus, enhance the activation of cannabinoid receptors. Thus, the compound may not directly modulate the cannabinoid receptors but has the effect of indirectly stimulating the cannabinoid receptors by increasing the levels of endocannabinoid ligands. It may also enhance the effects and duration of action of other exogenous cannabinergic ligands that are administered in order to elicit a cannabinergic response.

6 Claims, No Drawings

(51) Int. Cl.

| | |
|---|---|
| *C07C 271/16* | (2006.01) |
| *C07C 271/24* | (2006.01) |
| *C07C 271/38* | (2006.01) |
| *C07C 271/58* | (2006.01) |
| *C07C 309/68* | (2006.01) |
| *C07C 309/81* | (2006.01) |
| *C07C 309/82* | (2006.01) |
| *C07D 213/30* | (2006.01) |
| *C07D 213/40* | (2006.01) |
| *C07D 213/50* | (2006.01) |

(56) References Cited

FOREIGN PATENT DOCUMENTS

| | | | |
|---|---|---|---|
| FR | 2126545 | * | 10/1972 |
| WO | WO03007923 A2 | | 1/2003 |
| WO | WO2004033652 A2 | | 4/2004 |
| WO | WO 2004108684 A1 | * | 12/2004 |

OTHER PUBLICATIONS

Karanian. D.A. The Journal of Neurosciences. Aug. 2005, vol. 25. No. 34, pp. 7813-7820.*
Solodukhin et al, Molecules (2004), 9(3), 164-169.*
English language translation of WO 2004108684, Dec. 2004.*
Singh et al, Journal of Organic Chemistry, 2001, 66 (19), pp. 6263-6267.*
Buck et al, Journal of the American Chemical Society (1932), 54, pp. 4359-4365.*
Kappe et al, Chemical Abstract Service, Database Accession No. 1972:405389 of Monatsh. Chem. (1972), 103(2), 426-34.*
Barhdadi et al,Tetrahedron (1993), 49(23), 5091-8.*
Buss et al, Journal of Fluorine Chemistry (1998), 88(2), 111-116.*
Kappe et al, Monatsh. Chem. (1972), 103(2), 426-34 (English Translation).*
Merck & Co., Inc, Chemical Abstract Service, Database Accession No. 78:110853 of FR 2126545.*
Merck & Co., Inc, Chemical Abstract Service, Database Accession No. 78:110853 of FR 2126545 (1973).*
Machine Translation of FR 2126545 (Oct. 1972).*
European Search Report dated Feb. 7, 2012.
Boger, D. L. et al., "Trifluoromethyl Ketone Inhibitors of Fatty Acid Amide Hydrolase: a Probe of Structural and Conformational Features Contributing to Inhibition", Bioorganic & Medicinal Letters, Pergamon, Elsevier Science, GB, vol. 9, No. 2, Jan. 18, 1999.
Rice, H. L et al., "An Improved Procedure for the Preparation of Alkyl Halide Derivatives of Saccharin", Journal of the American Chemical Society, Washington, DC, vol. 76, Jan. 1, 1954.
Abe, K., "A New Method for the Preparation of Secondary Amines, IV Syntheses of Ethylenediamine, Ethanolamine, Triethylenediamine and Propanolamine Derivatives", Yakugaku Zasshi, vol. 75, Jan. 1, 1955.
Sah, P. P. T. et al., "p-Bromobenzazide as a Reagent for the Identification of Alcohols", Receuil Des Travaux Chimique Des Pays-Bas, vol. 58, Jan. 1, 1939.
Shimizu, H. et al., "Sythesis of Alpha-Keto Esters by the Rhodium-Catalysed Reaction of Cynoformate with Arylboronic Acids", Chemical Communications, Apr. 26, 2007.

* cited by examiner

FATTY ACID AMIDE HYDROLASE INHIBITORS

CONTINUING DATA

This application is a 371 of PCT/US2007/016953 filed Jul. 27, 2007 which claims benefit of 60/833,937 filed Jul. 28, 2006.

FIELD

The present disclosure relates generally to chemical compounds of formula R—X—Y and use of those compounds to inhibit fatty acid amide hydrolase (FAAH).

SUMMARY

Presently, two $G_{i/o}$ protein coupled cannabinoid receptors have been characterized in mammals and other organisms: CB1, a central receptor found in the mammalian brain and a number of other sites in peripheral tissues; and CB2, a peripheral receptor found principally in cells related to the immune system. Some compounds (cannabinergic ligands) can bind to the CB1 and/or CB2 receptors in an individual or animal. In vitro methods for assaying the ability of a compound to bind to CB 1 and/or CB2 receptors are known. Results from the in vitro assay correlate with and predict the in vivo ability of that compound to bind to CB1 and/or CB2 receptors and modulate their function(s).

When introduced in an individual or animal some of these cannabinergic ligands can bind to and directly modulate (activate or deactivate) the CB1 and/or CB2 receptors. Many physiological effects have been associated with direct modulation of the CB1 and/or CB2 receptors in an individual or animal. Examples of some cannabinergic ligands include anandanide and 2-arachidonoylglycerol (both endogenous ligands for the cannabinoid CB1 and CB2 receptors), $(-)-\Delta^9$-tetrahydrocannabinol (the principal bioactive constituent of cannabis and exogenous ligand for the cannabinoid CB1 and CB2 receptors) and other synthetic cannabinergic analogs.

Despite having a rapid onset of action, the magnitude and duration of in vivo CB1 and/or CB2 receptor modulation by cannabinergic ligands such as anandamide is relatively short, presumably because of a rapid inactivation process comprising hydrolysis of that cannabinergic ligand by fatty acid amide hydrolase (FAAH). Fatty acid amide hydrolase (FAAH), also referred to as anandamide amidase (AEAase) and anandamide amidohydrolase (AAH) in early studies, is an intracellular membrane-bound enzyme that degrades and inactivates members of the endocannabinoid class of signaling lipids such as anandamide (arachidonoyl ethanolamine). FAAH belongs to the amidase signature (AS) super family of serine hydrolases and in contrast to the classical serine-histidine-aspartate triad found in most serine hydrolases, the catalytic machinery of this enzyme is a serine-serine-lysine catalytic triad. FAAH has been isolated, molecularly cloned and its 2.8 Å crystal structure was recently reported. 2-arachidonoylglycerol (2-AG), 1-arachidonoylglycerol, arachidonamide and the corresponding simple ester methyl arachidonate are also substrates for FAAH.

Moreover, studies have demonstrated that this enzyme not only can hydrolyze anandamide into arachidonic acid and ethanolamine but it can also catalyze its reverse synthesis from the two hydrolysis components. Also notable is FAAH's ability to hydrolyze several bioactive fatty acid amides not belonging to the endocannabinoid family, for example, the sleep inducing lipid oleamide, the appetite-suppressing agent oleoylethanolamine, the related 1-oleoylglycerol, and the peripheral analgesic and anti-inflammatory mediator palmitoylethanolamine. Despite the fact that a range of fatty acid amides, ethanolamides and esters are hydrolyzed by FAAH, this enzyme appears to work most effectively on arachidonoyl and oleoyl substrates.

Some compounds can inhibit the inactivation of cannabinergic ligands by fatty acid amide hydrolase (FAAH). These compounds may not bind to, or may have lesser affinity for, the cannabinoid receptors. Thus, the physiological action for such compounds is inhibition of fatty acid amide hydrolase (FAAH) and not direct modulation of the CB1 and/or CB2 receptors.

Inhibition of fatty acid amide hydrolase (FAAH) in an individual or animal will slow the normal degradation and inactivation of endogenous cannabinoid ligands by FAAH hydrolysis and allow higher levels of those endogenous cannabinergic ligands to remain present in that individual or animal. These higher levels of endocannabinoid ligands provide increased stimulation of the cannabinoid CB1 and CB2 receptors and produce physiological effects related to the activation of the cannabinoid receptors. They will also enhance the effects of other exogenous cannabinergic ligands and allow them to produce their effects at lower concentrations as compared to systems in which fatty acid amide hydrolase (FAAH) action is not inhibited. Thus, a compound that inhibits the inactivation of endogenous cannabinoid ligands by fatty acid amide hydrolase (FAAH) may increase the levels of endocannabinoids and, thus, enhance the activation of cannabinoid receptors. Thus, the compound may not directly modulate the cannabinoid receptors but has the effect of indirectly stimulating the cannabinoid receptors by increasing the in vivo levels of endocannabinoid ligands. It may also enhance the effects and duration of action of other exogenous cannabinergic ligands that are administered in order to elicit a cannabinergic response.

Marijuana-like cannabinoids, in addition to acting at cannabinoid receptors also affect cellular membranes, thereby producing undesirable side effects such as drowsiness, impairment of monoamide oxidase function and impairment of non-receptor mediated brain function. The addictive and psychotropic properties of some cannabinoids also limit their therapeutic value. Compounds that inhibit FAAH activity may indirectly provide desirable pharmacological properties while avoiding the disadvantages incurred by use of cannabinergic ligands that directly activate the cannabinoid receptors. Compounds that inhibit FAAH activity (FAAH inhibitors) provide an alternative mechanism for indirectly stimulating cannabinoid receptors and may provide desirable pharmacological properties without the addictive and psychotropic properties as well as other undesirable properties associated with increased concentrations of cannabinoids.

FAAH analogs comprise two pharmacophoric subunits responsible for enzyme recognition and inactivation. The "inhibition" subunit typically comprises an activated sulfonyl or carbonyl group which inhibits the fatty acid amide hydrolase. The "binding" subunit, which is linked to the inhibition subunit, enhances the inhibitory action of the molecule. The presence of a lipid-like binding subunit may confer on the molecule a number of unfavorable biopharmaceutical properties, for example, high accumulation in fat tissues, low water solubility, high plasma protein binding and limited target selectivity.

The present disclosure provides compounds. In some embodiments the compounds can be new and structurally improved FAAH inhibitors. In some embodiments the compounds comprise the saccharin nucleus and the difluoromethyleneketo group as novel FAAH inhibition subunit pharmacophores. Biological test results of some synthesized compounds confirm that introduction of substituents containing heteroatoms in the binding subunit pharmacophore significantly enhances the ligands' affinity. This can be seen by comparison of the "% inhibition" (Table 1) of compounds 4.1, 4.2, and 4.3 with compounds 13.1-4, 14.1-4, and 17; and comparison of compounds 83.1 with compounds 83.2, 83.3, and 84, as well as by comparison of the "Ki" values (Table 1) of compounds 27.1-3 with, for example, compounds 23.7, 23.9, and 24.4; and comparison of compound 89.10 with compound 89.11; and comparison of compound 89.12 with compound 89.13. This was a surprising discovery that allowed the inventors to obtain novel analogs possessing superior properties for FAAH inhibition.

One aspect of the disclosure provides compounds represented by the general formula I and pharmaceutically acceptable (i.e. non-toxic, physiologically acceptable) salts thereof. In the general formula I, Y represents the inhibition subunit pharmacophore, and R—X represents the binding subunit pharmacophore. The disclosure includes all stereoisomers (geometric isomers, diastereomers and enantiomers).

R—X—Y    (I)

wherein:

Y is selected from the following structures:

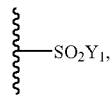
I1

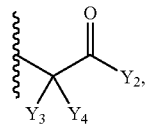
I2

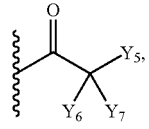
I3

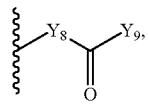
I4

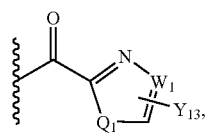
I5

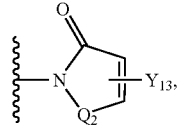
I6

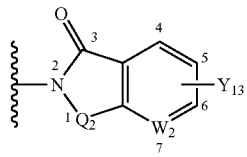
I7

$Y_1$ is selected from —F, —Cl, —O-alkyl, —O-cycloalkyl, —O-heterocyclic, —O-aryl, —O-heteroaryl and —O-adamantyl.

$Y_2$ is selected from —H, —OH, —NH$_2$, —OMe, —OEt, —CF$_3$, —C≡CH, —CH$_2$—C≡CH, —CH=CH$_2$, fluoroalkyl, —C$_{1-5}$-alkyl, -aryl, -aryl-alkyl, -aryl-alkyl-Y$_{14}$, -aryl-heteroaryl, -aryl-aryl, -heteroaryl, -heteroaryl-alkyl, -heteroaryl-alkyl-Y$_{14}$, -heteroaryl-aryl, -heteroaryl-heteroaryl, -cycloalkyl, -cycloalkyl-alkyl, -cycloalkyl-alkyl-Y$_{14}$, -heterocyclic, -heterocyclic-alkyl, -heterocyclic-alkyl-Y$_{14}$, -adamantyl, —C$_{1-5}$-alkyl-Y$_{14}$, -aryl-Y$_{14}$, -heteroaryl-Y$_{14}$, -cycloalkyl-Y$_{14}$, -heterocyclic-Y$_{14}$ and -adamantyl-Y$_{14}$.

$Y_3$ and $Y_4$ are each independently selected from —F, —Cl and —OH or $Y_3$ and $Y_4$ together form an oxo group, that is Y3 and Y4 together with the common carbon atom form the structure >C=O.

$Y_5$ is selected from —F, —CONH$_2$, —SO$_2$NH$_2$, —COOH, —COOMe, —COOEt, —CF$_3$, —C≡CH, —CH$_2$—C≡CH, —CH=CH$_2$, fluoroalkyl, —C$_{1-5}$-alkyl, aryl, heteroaryl, cycloalkyl, heterocyclic, adamantyl, —C$_{1-5}$-alkyl-Y$_{14}$, -aryl-Y$_{14}$, -heteroaryl-Y$_{14}$, -cycloalkyl-Y$_{14}$, adamantyl-Y$_{14}$ and -heterocyclic-Y$_{14}$.

$Y_6$ and $Y_7$ are each independently selected from —F, —Cl and —OH.

$Y_8$ is selected from >NH and —O—.

$Y_9$ is selected from —OY$_{10}$ and —N(Y$_{11}$)Y$_{12}$.

$Y_{10}$ is selected from alkyl, aryl, benzyl, difluorophenyl, fluorophenyl, heteroaryl, cycloalkyl, adamantyl, heterocyclic, —C$_{1-5}$-alkyl-Y$_{14}$, -aryl-Y$_{14}$, -heteroaryl-Y$_{14}$, -cycloalkyl-Y$_{14}$, -adamantyl-Y$_{14}$ and -heterocyclic-Y$_{14}$.

$Y_{11}$ is —H.

$Y_{12}$ is selected from alkyl, aryl, heteroaryl, cycloalkyl, adamantyl, heterocyclic, —C$_{1-5}$-alkyl-Y$_{14}$, —C$_{1-5}$-alkyl-aryl, —C$_{1-5}$-alkyl-heteroaryl, -aryl-Y$_{14}$, -heteroaryl-Y$_{14}$, -cycloalkyl-Y$_{14}$, -adamantyl-Y$_{14}$ and -heterocyclic-Y$_{14}$, or Y$_{11}$ and Y$_{12}$ together comprise part of a 5 or 6 membered saturated heterocyclic ring containing up to one additional heteroatom selected from N, O and S.

$Y_{13}$ is selected from —H, —OH, —SH, —NH$_2$, —CN, —N$_3$, —NCS, —NCO, —CONH$_2$, —SO$_2$NH$_2$, —COOH, —COOMe, —COOEt, —NO$_2$, —CF$_3$, —SO$_3$H, —P(O)(OH)$_2$, —C≡CH, —CH$_2$—C≡CH, —CH=CH$_2$, fluoroalkyl, —C$_{1-6}$-alkyl, aryl, heteroaryl, cycloalkyl, adamantyl, heterocyclic, —C$_{1-6}$-alkyl-Y$_{14}$, -aryl-Y$_{14}$, -heteroaryl-Y$_{14}$, -cycloalkyl-Y$_{14}$, -adamantyl-Y$_{14}$ and -heterocyclic-Y$_{10}$.

$Y_{14}$ is selected from —F, —Cl, Br, —I, —OH, —OMe, —OEt, —OPh, —OBn, —SH, —NH$_2$, —CN, —N$_3$, —NCS, —NCO, —CONH$_2$, —SO$_2$NH$_2$, —COOH, —COOMe, —COOEt, —NO$_2$, —CF$_3$, —SO$_3$H, —P(O)(OH)$_2$, —C≡CH, —CH$_2$—C≡CH and —CH=CH$_2$.

$W_1$ is selected from CH and N if Y$_{13}$ is not bonded to W$_1$, or W$_1$ is C if Y$_3$ is bonded to W$_1$.

W₂ is selected from CH and N if W₂ is not bonded to Y₁₃, or W₂ is C if W₂ is bonded to Y₁₃. If W₂ is N then it can occupy any position selected from 4, 5, 6 and 7 in I 7.

Q₁ is selected from >CH₂, >O, >S and >NH if Q₁ is not bonded to Y₁₃, or Q₁ is selected from >CH and >N if Q₁ is bonded to Y₁₃.

Q₂ is selected from >SO₂, >C(O) and >S(O).

X is selected from —(CH₂)ₙ— and —(CH₂)ⱼ-A-(CH₂)ₖ—.

A is selected from —CH=CH—, —C≡C—, C=O, O, S and NH.

n is an integer from 0 to about 15.

j is an integer from 0 to about 10.

k is an integer from 0 to about 10.

R is selected from the following structures:

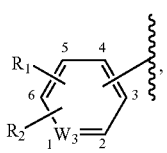
I 8

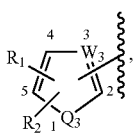
I 9

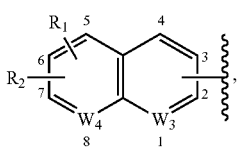
I 10

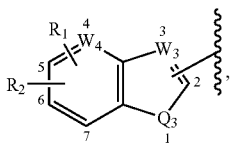
I 11

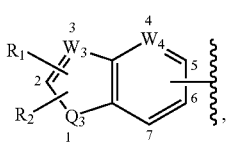
I 12

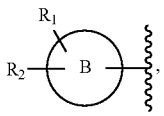
I 13

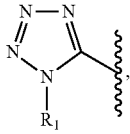
I 14

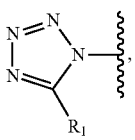
I 15

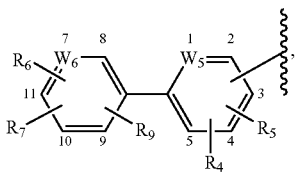
I 16

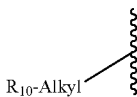
I 17 wherein:

W₃ is selected from CH and N if W₃ is not bonded to X or R₁ or R₂, or W₃ is C if W₃ is bonded to X or R₁ or R₂. If W₃ is N then it can occupy any position selected from 1, 2, 3, 4, 5 and 6 in I 8; 2, 3, 4 and 5 in I 9; 1, 2, 3 and 4 in I 10; 2 and 3 in I 11, I 12.

W₄ is selected from CH, N if W₄ is not bonded to X or R₁ or R₂, or W₄ is C if W₄ is bonded to X or R₁ or R₂. If W₄ is N then it can occupy any position selected from 5, 6, 7 and 8 in I 10; 4, 5, 6 and 7 in I 11, I 12.

W₅ is selected from CH and N if W₅ is not bonded to X or R₄ or R₅, or W₅ is C if W₅ is bonded to X or R₄ or R₅. If W₅ is N then it can occupy any position selected from 1, 2, 3, 4, and 5 in I 16.

W₆ is selected from CH and N if W₆ is not bonded to R₆ or R₇ or R₈ or R₉, or W₆ is C if W₆ is bonded to R₆ or R₇ or R₈ or R₉. If W₆ is N then it can occupy any position selected from 7, 8, 9, 10, and 11 in I 16.

Q₃ is selected from CH₂, O, S and NH if Q₃ is not bonded to X or R₁ or R₂, or Q₃ is selected from CH and N if Q₃ is bonded to X or R₁ or R₂.

B is an adamantyl or a heteroadamantyl ring.

R₁ and R₂ are each independently selected from —H, —F, —Cl, —Br, —I, —OH, —SH, —NH₂, —CN, —N₃, —NCS, —NCO, —CONH₂, —SO₂NH₂, —COOH, —NO₂, —CHO, —CF₃, —SO₃H, —SO₂Cl, —SO₂F, —O—P(O)(OH)₂, —O—P(O)(O-alkyl)₂, —O—P(O)(OH)(O-alkyl), —P(O)(O-alkyl)₂, —P(O)(OH)(O-alkyl), —Sn(alkyl)₃, —Si(alkyl)₃, —C≡CH, —CH₂—C≡CH, —CH=CH₂, -alkyl-R₃, -cycloalkyl-R₃, -heterocyclic-R₃, -aryl-R₃, -heteroaryl-R₃, -alkyl-cycloalkyl-R₃, -alkyl-heterocyclic-R₃, -alkyl-aryl-R₃, -alkyl-heteroaryl-R₃, -Z-alkyl-R₃, -Z-cycloalkyl-R₃, -Z-heterocyclic-R₃, -Z-aryl-R₃, -Z-heteroaryl-R₃, -Z-alkyl-cycloalkyl-R₃, -Z-alkyl-heterocyclic-R₃, -Z-alkyl-aryl-R₃, -Z-alkyl-heteroaryl-R₃, -aryl-Z-alkyl-R₃, -aryl-Z-cycloalkyl-R₃, -aryl-Z-heterocyclic-R₃, -aryl-Z-aryl-R₃, -aryl-Z-heteroaryl-R₃, -aryl-Z-alkyl-cycloalkyl-R₃, -aryl-Z-alkyl-heterocyclic-R₃, -aryl-Z-alkyl-aryl-R₃, -aryl-Z-alkyl-heteroaryl-R₃, —CH(alkyl-R₃)₂, —C(alkyl-R₃)₃, —N(alkyl-R₃)₂, —C(O)N(alkyl-R₃)₂ and —SO₂N(alkyl-R₃)₂.

Z is selected from —O, —S, —NH, —C(O), —C(O)O, —OC(O), —C(O)NH, —NHC(O), —SO, —SO₂, —SO₂NH, —NHSO₂, —SO₂O and —OSO₂.

R₃ is selected from —H, —F, —Cl, —Br, —I, -Me, -Et, —OH, —OAc, —SH, —NH₂, —CN, —N₃, —NCS, —NCO, —CONH₂, —SO₂NH₂, —COOH, —NO₂, —CHO, —CF₃, —SO₃H, —SO₂F, —O—P(O)(OH)₂, —Sn(alkyl)₃, —Si(alkyl)₃, —OSi(alkyl)₃, —C≡CH, —CH₂—C≡CH and —CH=CH₂.

R₄, R₅, R₆, R₇, R₈, and R₉ are each independently selected from —H, —F, —Cl, —Br, —I, —OH, —OMe, —OEt, —OCH$_2$OCH$_3$, —OAc, —SH, —SMe, —SEt, —NH$_2$, —CN, —N$_3$, —NCS, —NCO, —CONH$_2$, —SO$_2$NR$_2$, —COOH, —NO$_2$, —CHO, —CF$_3$, —SO$_3$H, —SO$_2$F, —O—P(O)(OH)$_2$, —Sn(alkyl)$_3$, —Si(alkyl)$_3$, —OSi(alkyl)$_3$, -alkyl. -alkyl-R$_3$.

R$_{10}$ is selected from —H, —F, —Cl, —Br, —I, —OH, —OMe, —OEt, —OAc, —SH, —SMe, —SEt, —NH$_2$, —CN, —N$_3$, —NCS, —NCO, —CONH$_2$, —SO$_2$NH$_2$, —COOH, —NO$_2$, —CHO, —CF$_3$, —SO$_3$H, —SO$_2$F, —O—P(O)(OH)$_2$, —Sn(alkyl)$_3$, —Si(alkyl)$_3$, —OSi(alkyl)$_3$, —C≡CH, —CH$_2$—C≡CH and —CH═CH$_2$.

The following provisos can apply to some of the disclosed embodiments.

If Y is —SO$_2$—Y$_1$ (I 1) where Y$_1$ is F or O-alkyl and X is —(CH$_2$)$_n$— where n=4-15 or —(CH$_2$)$_j$-A-(CH$_2$)$_k$—, where A is selected from O, S, —CH═CH— and —C≡C—, j and k are each a positive integer such that the sum of j and k is equal to 4-15 and R is I 8, I 9, I 10, I 11 or I 12 where R$_1$ is H; then R$_2$ can not be H, F, Cl, Br, I, NO$_2$, CF$_3$, CN, CHO, aryl-R$_3$, heteroaryl-R$_3$, O-alkyl-R$_3$, O-aryl-R$_3$, C(O)—O-alkyl-R$_3$, C(O)-alkyl-R$_3$, C(O)NH-alkyl-R$_3$, C(O)N(alkyl-R$_3$)$_2$ or S-alkyl-R$_3$, where R$_3$═H.

If Y is I 3 where Y$_5$ is F, Y$_6$ is F, Y$_7$ is F and X is —(CH$_2$)$_n$— where n=5-7; then R can not be phenyl, 2-hexyl-phenyl, 3-hexyl-phenyl, 4-heptyl-phenyl or 2-octyl-phenyl.

If Y is I 3 where Y$_5$ is F, Y$_6$ is F, Y$_7$ is F and X is —(CH$_2$)$_n$— where n=3; then R can not be 2-butyl-naphthyl.

If Y is I 4 where Y$_8$ is NH and Y$_9$ is OY$_{10}$ where Y$_{10}$ is alkyl, phenyl, pyridyl or C$_{1-5}$-alkyl-Y$_{14}$ where Y$_{14}$═NH$_2$ or NO$_2$ and X is —(CH$_2$)$_n$— where n=0-3; then R can not be naphthyl, indolyl or I 8 where W$_1$ is CH and R$_1$ and R$_2$ are each selected from O—C$_{1-16}$-alkyl, O—C$_{1-16}$-alkyl-phenyl, O—C$_{1-6}$-alkyl-pyridyl, phenyl, O-phenyl, O-pyridyl or C(O)NH—C$_{1-16}$-alkyl.

If Y is I 5 where W$_1$ is CH or N, Q$_1$ is O or S, Y$_{13}$ is H, C$_{1-6}$-alkyl, aryl or heteroaryl and X is —(CH$_2$)$_n$— where n=3-9 or X is —(CH$_2$)$_j$-A-(CH$_2$)$_k$— where A is O, S or NH and the sum of j and k is equal to 2-8; then R cannot be aryl.

If Y is I 5 where W$_1$ is N, Q$_1$ is O or S, Y$_{13}$ is selected from phenyl, 2-pyridyl, 3-pyridyl, 4-pyridyl and 2-furyl and X is —(CH$_2$)$_n$— where n=5-8; then R can not be 18 where W$_1$ is CH, R$_1$ is H and R$_2$ is H.

If Y is I 5 where W$_1$ is CH, Q$_1$ is O or S, Y$_{13}$ is selected from phenyl, 2-pyridyl, 3-pyridazinyl, 4-pyrimidinyl, 2-pyrimidinyl, 5-pyrimidinyl, 3-pyrazinyl, 2-thiophenyl, 2-furyl, 2-thiazolyl or 2-oxazolyl and X is —(CH$_2$)$_n$— where n=1-10 then R can not be 18 where W$_1$ is CH, R$_1$ is H and R$_2$ is H.

If Y is I 4 where Y$_8$ is O and Y$_9$ is N(Y$_{11}$)Y$_{12}$ and X is —(CH$_2$)$_n$— where n=0-3 then R can not be selected from I 8, I 9, I 10, I 11 and I 12.

If Y is I 4 where Y$_8$ is NH and Y$_9$ is N(Y$_{11}$)Y$_{12}$ where Y$_{11}$ is H and Y$_{12}$ is cyclohexyl and X is —(CH$_2$)$_n$— where n=0, then R can not be naphthyl.

If Y is selected from structure I 1 or I 3 or I 4 or I 5, then R can not be the structure I 17.

The disclosed compounds in any formula, embodiment or variation include any and all possible isomers and stereoisomers. The content of any publication cited herein is incorporated by reference.

In general, the compositions of the disclosure may be alternately formulated to comprise, consist of, or consist essentially of, any appropriate components herein disclosed. The compositions of the disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

Unless otherwise specifically defined, "acyl" refers to the general formula —C(O) alkyl.

Unless otherwise specifically defined, "alcohol" refers to the general formula alkyl-OH and includes primary, secondary and tertiary variations.

Unless otherwise specifically defined, "alkyl" refers to a linear or branched hydrocarbon radical which may be fully saturated, mono- or polyunsaturated and can include divalent radicals, having from 1 to about 15 carbon atoms. Examples for saturated hydrocarbon radicals include, but are not limited to, groups such as methyl(Me), ethyl(Et), n-propyl, isopropyl, n-butyl, t-butyl, isobutyl, sec-butyl, homologs and isomers of, for example, n-pentyl, n-hexyl, n-heptyl, n-octyl, 1,1-dimethyl-heptyl, 1,2-dimethyl-heptyl, and the like. An unsaturated alkyl group includes one or more double bonds, triple bonds or combinations thereof. Examples of unsaturated alkyl groups include but are not limited to, vinyl, propenyl, crotyl, 2-isopentenyl, allenyl, butenyl, butadienyl, pentenyl, pentadienyl, 3-(1,4-pentadienyl), hexenyl, hexadienyl, ethynyl, propynyl, butynyl, and higher homologs and isomers. The term "divalent alkyl radicals" unless otherwise specifically defined refers to the general formula: -alkyl-. The term "Cl$_{1-m}$-alkyl" refers to an alkyl having from 1 to about m carbon atoms.

Unless otherwise specifically defined, "alkoxy" refers to the general formula —O-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, "aroyl" refers to the general formula —C(═O)-aryl.

Unless otherwise specifically defined, "aryl" refers to a polyunsaturated, aromatic hydrocarbon, which can be a single ring or multiple rings (preferably from 1 to 3 rings) which are fused together or linked covalently and can include "divalent radicals". The term "divalent aryl radicals" unless otherwise specifically defined refers to the general formula: -aryl-. Examples of aryl groups include but are not limited to, phenyl, biphenyl, and naphthyl.

Unless otherwise specifically defined, "cycloalkyl" or "cycloalkyl ring" refers to a saturated or partially saturated ring structure having about 3 to about 8 ring members that has only carbon atoms as ring atoms and can include divalent radicals. The term "divalent cycloalkyl radicals" unless otherwise specifically defined refers to the general formula: -cycloalkyl-. Examples of cycloalkyl groups include but are not limited to, cyclopropyl, cyclobutyl, cyclopentyl, cyclohexyl, cyclohexene.

Unless otherwise specifically defined, "halogen" refers to an atom selected from fluorine, chlorine, bromine and iodine.

Unless otherwise specifically defined, "heterocyclic" or "heterocyclic ring" refers to a saturated ring structure having about 3 to about 8 ring members that has carbon atoms and one or more heteroatoms, including oxygen, nitrogen and/or sulfur, as ring atoms. The term "heterocyclic" or "heterocyclic ring" can include "divalent radicals". The term "divalent heterocyclic radicals" unless otherwise specifically defined refers to the general formula: -heterocyclic-. Examples of heterocyclic groups include but are not limited to, oxetane, thietane, azetidine, diazetidine, tetrahydrofuran, thiolane, pyrrolidine, dioxolane, oxathiolane, imidazolidine, dioxane, piperidine, morpholine, piperazine, and their derivatives.

Unless otherwise specifically defined, "heteroaryl" refers to aryl groups (or rings) that contain one or more heteroatoms selected from oxygen, nitrogen and/or sulfur as ring atoms. Heteroaryl groups (or rings) also include fused polycyclic systems in which one or more monocyclic aryl or monocyclic heteroaryl group is fused to another heteroaryl group. "Heteroaryl" can include "divalent radicals", the term "divalent heteroaryl radicals" unless otherwise specifically defined refers to the general formula: -heteroaryl-. Examples of heteroaryl groups include but are not limited to, furanyl, thienyl, pyrrolyl, oxazolyl, thiazolyl, isoxazolyl, pyrazolyl, imidazolyl, oxadiazolyl, pyridinyl, pyrimidinyl, purinyl, benzoxazolyl, benzothiazolyl, benzimidazolyl, benzofuranyl, indolyl, quinolinyl, quinoxalinyl.

Unless otherwise specifically limited the term substituted means substituted by a below-described substituent group in any possible position. Substituent groups for the above moieties useful in this disclosure are those groups that do not significantly diminish the biological activity of the disclosed compound. Substituent groups that do not significantly diminish the biological activity of the disclosed compound include, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, $C(halogen)_3$, $COOX_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide, thioalkoxy or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, hydroxyloweralkyl, or alkyl-$NX_1X_2$. Unless otherwise specifically limited a substituent group may be in any possible position.

A carbonyl group of compounds disclosed herein may exist in the hydrate form, for example see compounds 24.5 and 89.9 in Table 1. Therefore, hydrates of the compounds as well as mixtures of the hydrate- and the keto-form of the compounds are included in this disclosure.

The disclosed compounds may be isolated from a naturally occurring or synthetic material. The isolated compound may be contemporaneously or subsequently "purified" or "substantially purified". As used herein a purified or substantially purified compound means a compound that has been processed to a desired purity. A person of ordinary skill can establish the desired purity for a use and method to achieve that purity without undue effort. The purified compound may be used in any disclosed embodiment.

The compounds of the present disclosure may have unnatural ratios of atomic isotopes at one or more of their atoms. For example the compounds may be labeled with isotopes, such as deuterium, tritium carbon-11, carbon-14, iodine-123, iodine-125 or fluorine-18. The present disclosure encompasses all isotopic variations of the described compounds, whether radioactive or not.

Testing of some compounds disclosed herein showed inhibition of the fatty acid amide hydrolase. Thus, another aspect is use of at least one compound, and pharmaceutically acceptable salts thereof, to inhibit fatty acid amide hydrolase.

The disclosed compounds, and pharmaceutically acceptable salts thereof, have high potential to be used as research tools to probe FAAH and related amidase mechanisms of catalysis, and to uncover the biological roles of lipid mediators such as anandamide, 2-arachidonoylglycerol and oleamide. For example, the disclosed compounds can be used as in vivo imaging agents; to maintain the level of anandamide in vitro to study the effect of anandamide on cells and to maintain the level of anandamide in vivo to study the effect of anandamide on individuals and animals. The disclosed compounds can be used to characterize cells, for example to determine if a cell type has cannabimimetic or amidase activity. For example, the disclosed compounds can be used to determine if a cell population expresses FAAH by contacting the cells with a disclosed compound and then determining if there is an increase in the concentration of anandamide. The FAAH inhibitors disclosed herein can also be used as in aid in drug design, for example as a control in assays for testing other compounds for their ability to inhibit FAAH and to determine the structure activity requirements of FAAH inhibitors.

Testing of some compounds disclosed herein showed inhibition of the fatty acid amide hydrolase in both in vitro and in vivo systems. Inhibition of fatty acid amide hydrolase (FAAH) has the effect of preventing the degradation of endocannabinoid ligands and enhancing or maintaining the level of endocannabinoid ligands in a system. Thus some disclosed compounds, and pharmaceutically acceptable salts thereof, have high potential when administered in therapeutically effective amounts for enhancing or maintaining the in vivo concentration of endogenous cannabinergic ligands in an individual or animal.

Cannabinergic ligands can bind to and directly modulate (activate or deactivate) the CB1 and/or CB2 receptors. Modulation of the CB1 and/or CB2 receptors in an individual or animal provides a physiological effect in that individual or animal. Some physiological effects provided by modulation of the CB1 and/or CB2 receptors in an individual or animal include neuroprotection; reduction of inflammation; reduction of pain; reduction of central pain; reduction of peripheral pain; modulation of memory; sleep inducement; modulation of the immune system; hypotension; reduction of emesis; effects on gastrointestinal motility; effects on motor function; effects on intestinal transit and colonic propulsion; modulation of appetite; and modulation of fertility. Inhibition of fatty acid amide hydrolase (FAAH) activity has the effect of enhancing or maintaining the concentration of existing levels of endogenous cannabinergic ligands and thereby enhancing or maintaining the magnitude and duration of the physiological effect provided by those cannabinergic ligands. Thus some disclosed compounds, and pharmaceutically acceptable salts thereof, have high potential when administered in therapeutically effective amounts for enhancing or maintaining the magnitude and duration of the physiological effects provided by an exogenously administered cannabinergic ligand in an individual or animal.

Cannabinergic ligands can bind to and directly modulate (activate or deactivate) the CB1 and/or CB2 receptors and thereby provide a physiological effect in an individual or animal that is useful to treat a condition in that individual or animal. Inhibition of fatty acid amide hydrolase (FAAH) has the effect of enhancing or maintaining the levels, magnitude and duration of endocannabinoid ligands and thereby enhancing or maintaining the magnitude and duration of the physiological effect provided by those cannabinergic ligands in an individual or animal. Some disclosed compounds, and pharmaceutically acceptable salts thereof, have high potential when administered in therapeutically effective amounts for enhancing or maintaining the magnitude and duration of the physiological effects produced by a cannabinergic ligand in an individual or animal for treatment of a condition in that individual or animal. Conditions that may be treated by inhibition of fatty acid amide hydrolase (FAAH) and indirect stimulation of the cannabinoid receptors include, for example: appetite disorders, metabolic disorders, movement disorders, inflammation, pain, central pain, peripheral pain, neuropathy, neurodegenerative diseases including multiple sclerosis, neurodegeneration, Parkinson's disease, Huntington's chorea, Alzheimer's disease, amyotrophic lateral sclerosis, memory disorders, mood disorders, sleep disorders, gastrointestinal motility disorders such as irritable bowel syndrome and diarrhea, cardiovascular disease, hypertension, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, psychological disorders including anxiety disorders (e.g. panic disorder, acute stress disorder, post-traumatic stress disorder, substance-induced anxiety disorder, obsessive-compulsive disorder, agoraphobia, specific phobia and social phobia); or to modulate the immune system; to regulate fertility; to prevent or treat diseases associated with motor function such as Tourette's syndrome, to provide neuroprotection; to produce peripheral vasodilation; to slow down intestinal transit and colonic propulsion; to treat several types of cancer; as well as other ailments in which a growing family of bioactive lipid mediators is implicated. Thus, another aspect of the disclosure is the administration of a therapeutically effective amount of a described compound, or a pharmaceutically acceptable salt thereof, to an individual or animal to provide a physiological effect for treatment of a condition in that individual or animal.

These compounds can also be used in conjunction with other cannabinergic ligands that act directly on the CB1 and CB2 receptors to enhance the ability of the other ligands to activate the CB1 and CB2 receptors.

The disclosed compounds, and pharmaceutically acceptable salts thereof may be used to prepare prodrugs. As used herein, the term "prodrug" refers to any derivative of the compounds of general formula I that are metabolized or otherwise converted into an active form upon introduction into the body of an individual or animal. Prodrugs are well known to those skilled in the art of pharmaceutical chemistry, and provide benefits such as increased adsorption and half-life. Those skilled in the art of drug delivery will readily appreciate that the pharmacokinetic properties of general formula I may be controlled by an appropriate choice of moieties to produce prodrug derivatives.

Description of Some Preferred Embodiments

As used herein a "therapeutically effective amount" of a compound, is the quantity of a compound which, when administered to an individual or animal, results in a discernible physiological effect in the individual or animal. The compounds disclosed herein, and pharmaceutically acceptable salts thereof, have pharmacological properties when administered in therapeutically effective amounts for providing a physiological effect useful to treat a number of physiological conditions. Typically, a "therapeutically effective amount" of a compound is believed to range from about 5 mg/day to about 1,000 mg/day. As used herein, an "individual" refers to a human. An "animal" refers to, for example, veterinary animals, such as dogs, cats, horses and the like, and farm animals, such as cows, pigs and the like.

One or more disclosed compounds, typically after purification, can be incorporated into a pharmaceutical composition or medicament. The disclosed compounds can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The pharmaceutical composition or medicament can also contain a pharmaceutically acceptable vehicle, diluent, excipient or carrier and optional adjuvants, flavorings, colorants, wetting agents, emulsifying agents, pH buffering agents and preservatives. Some suitable pharmaceutically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

Some analogs were tested for their FAAH inhibitory activity, which is expressed as % of inhibition or $IC_{50}/Ki$ values (Table 1). The percentage of inhibition results from one-point assay (one concentration of inhibitor is used) and it is less accurate (preliminary screening) than the $IC_{50}/Ki$ values that are determined from eight-point assay (eight different concentrations of inhibitor were used). The percentage of inhibition describes the percentage by which the inhibitor reduces the velocity/rate of anandamide hydrolysis by FAAH. The $IC_{50}$ is the concentration of the inhibitor, which results in 50% inhibition of the velocity/rate of anandamide hydrolysis by FAAH. The Ki value is the affinity constant and describes the affinity of the inhibitor for the FAAH. The lower the $IC_{50}/Ki$ values, the higher the affinity of the inhibitor for the enzyme and the higher its inhibitory activity. A detailed description of the methods used to test inhibitory activity of compounds is given below.

Methods:

Partial Purification of FAAH:

Anandamide amidase enzyme is partially purified from adult Sprague-Dawley rat brains purchased from Pel-Freeze Biologicals according to a procedure disclosed in Lang, W et al., Anal. Biochem., 1996, 238, 40-45, the contents of which are incorporated by reference. These rat brains are homogenized in 5 vol of ice-cold buffer (0.32 M Sucrose, 10 mM Tris base, 5 mM EDTA, pH 7.4) then centrifuged at 17400 g for 30 min. The supernatant is further centrifuged at 124,000 g for 90 min; the pellet from the last centrifugation step (microsomal fraction) is resuspended in TME buffer (25 mM Tris base, 5 mM $MgCl_2$, 1 mM EDTA, pH 7.4) for the anandamide amidase preparation. Aliquots (1 ml) from the preparation are flash frozen in liquid nitrogen and stored at −80° C. until used. Protein concentration of the enzyme suspension is determined using the BioRad protein assay kit.

FAAH Enzyme Assay:

All compound solutions are made to a concentration of 10 mM in DMSO. To test the stability of the compounds in enzyme assay conditions, 25 nmoles of the compound are incubated in TME buffer with 0.1% BSA (final volume of 250 µL) for 15 minutes at 37° C. Samples (100 µL) are taken at the start of the assay and after 15 minutes, diluted 1:5 with acetonitrile and centrifuged (20,000 RCF, five minutes, room temperature) to precipitate the proteins. The resulting supernatant is injected onto the HPLC. Calculations for determining the percent compound remaining are described in the following equation:

$$\% R = \text{Peak Area } (T15)/\text{Peak Area } (T0)$$

To determine whether or not the compounds are good substrates for FAAH, 25 nmoles of the compound were incubated with 75 μg enzyme preparation in TME buffer with 0.1% BSA (final volume 250 μL). The reaction mixture is treated in the same manner as described above. Concentrations of anandamide (AEA) and arachidonic acid (AA) are calculated using external standards. The rate of AA formation is calculated using the following equation:

Rate=$(T15-T0)/15$ min/75 μg

The inhibition of AEA metabolism is measured by mixing 25 nmoles of the compound with 25 nmoles AEA, and 75 μg enzyme preparation in TME buffer with 0.1% BSA (final volume of 250 μL) as disclosed in Lang, W et al., Anal. Biochem., 1996, 238, 40-45, $Q_1$n, C et al.,. Anal. Biochem., 1998, 261, 8-15 and Lang, W et al., J. Med. Chem., 1999, 42, 896-902. Again the reaction mixture is treated in the same manner as described above and the concentrations of AEA and AA are calculated using external standards. Percent inhibition is calculated using the following equation:

% Inhib.=$(AA15-AA0)c/(AA15-AA0)s$ where $(AA15-AA0)c$ is the amount of arachidonic acid formed over 15 minutes from AEA with the inhibitor present and $(AA15-AA0)s$ is the amount of arachidonic acid formed over 15 minutes from AEA when the inhibitor is not present.

In the $IC_{50}$ studies of the disclosed analogs various concentrations of compound are incubated with 25 nmoles AEA, and 75 kg enzyme preparation in TME buffer (final volume of 250 μL). The reaction mixtures are treated as described above and the amount of AA formed was calculated. Prizm software (GraphPad Software, Inc.) is utilized to calculate $IC_{50}$ and $K_i$ values.

HPLC Conditions for the Enzyme Assay:

Chromatographic separation was achieved using an Ultrasphere ODS Pre-column (4.6×45 mm) from Beckman. Hardware consisted of a Waters Millennium HPLC system with a 20 μL injection loop. The mobile phase consisted of 8.5% o-phosphoric acid:acetonitrile (3:7), run isocratically at a rate of 1 mL/min and detection at 204 nm. The total run time was 8 minutes with AEA eluting at 2.2 minutes, 2-AG at 3.0 minutes, and AA at 6.0 minutes.

The following examples are given for purposes of illustration only in order that the present disclosure may be more fully understood. These examples are not intended to limit in any way the scope of the disclosure unless otherwise specifically indicated.

EXAMPLES

Some synthesized and purified fatty acid amide amidase inhibitors of compound formula I are depicted in Table 1.

TABLE 1

FAAH inhibitors of compound formula I (R—X—Y).

| Compound number | Structure I | % Inhibition (Concentration) | $IC_{50}$ (μM) | $K_i$ (μM) |
|---|---|---|---|---|
| 4.1[a] | 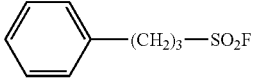 Ph—(CH$_2$)$_3$—SO$_2$F | 19% (100 μM) | | |
| 4.2[a] | 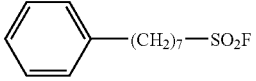 Ph—(CH$_2$)$_7$—SO$_2$F | 31% (100 μM) | | |
| 4.3[a] | 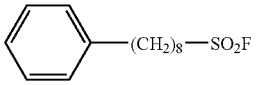 Ph—(CH$_2$)$_8$—SO$_2$F | 24% | | |
| 12.1[b] | 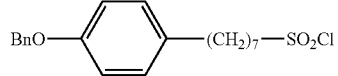 BnO—C$_6$H$_4$—(CH$_2$)$_7$—SO$_2$Cl | 99% (100 μM) | 53.8 | 12.7 |
| 12.2 | 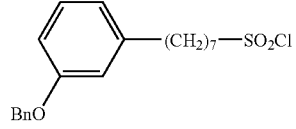 3-BnO-C$_6$H$_4$—(CH$_2$)$_7$—SO$_2$Cl | 97% (100 μM) | 12.0 | 2.9 |
| 12.3 | 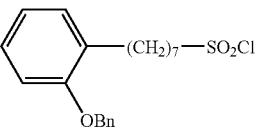 2-BnO-C$_6$H$_4$—(CH$_2$)$_7$—SO$_2$Cl | 97% (100 μM) | 1.75 | 0.41 |
| 12.4 | 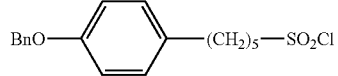 BnO—C$_6$H$_4$—(CH$_2$)$_5$—SO$_2$Cl | 95% (100 μM) | | |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 13.1 | BnO—C$_6$H$_4$—(CH$_2$)$_7$—SO$_2$F | 100% (100 μM) | 0.168 | 0.039 |
| 13.2 | 3-BnO—C$_6$H$_4$—(CH$_2$)$_7$—SO$_2$F | 97% (100 μM) | 0.165 | 0.039 |
| 13.3 | 2-BnO—C$_6$H$_4$—(CH$_2$)$_7$—SO$_2$F | 100% (100 μM) | 0.193 | 0.046 |
| 13.4 | BnO—C$_6$H$_4$—(CH$_2$)$_5$—SO$_2$F | 97% (100 μM) | 0.180 | 0.015 |
| 14.1 | HO—C$_6$H$_4$—(CH$_2$)$_7$—SO$_2$F | 100% (100 μM) | 0.098 | 0.023 |
| 14.2 | 3-HO—C$_6$H$_4$—(CH$_2$)$_7$—SO$_2$F | 99% (100 μM) | 0.113 | 0.026 |
| 14.3 | 2-HO—C$_6$H$_4$—(CH$_2$)$_7$—SO$_2$F | 100% (100 μM) | 0.054 | 0.013 |
| 14.4 | HO—C$_6$H$_4$—(CH$_2$)$_5$—SO$_2$F | 99% (100 μM) | 0.346 | 0.031 |
| 16 | C$_6$H$_5$—O—(CH$_2$)$_4$—SO$_2$Cl | 99% (100 μM) | 53.8 | 12.7 |
| 17 | C$_6$H$_5$—O—(CH$_2$)$_4$—SO$_2$F | 100% (100 μM) | 0.226 | 0.053 |
| 18 | BnO—C$_6$H$_4$—(CH$_2$)$_7$—SO$_2$OMe | 93% (100 μM) | 0.256 | 0.078 |
| 23.1 | BnO—C$_6$H$_4$—O—(CH$_2$)$_3$—COCF$_3$ | 96% (100 μM) | 1.8 | 0.15 |
| 23.2 | BnO—C$_6$H$_4$—O—(CH$_2$)$_4$—COCF$_3$ | 76% (100 μM) | 13.6 | 1.2 |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 23.3 | BnO—C$_6$H$_4$—O—(CH$_2$)$_5$—COCF$_3$ | 94% (100 μM) | 2.9 | 0.32 |
| 23.4 | BnO—C$_6$H$_4$—O—(CH$_2$)$_8$—COCF$_3$ | 88% (100 μM) | 11.8 | 0.83 |
| 23.5 | 3-BnO-C$_6$H$_4$—O—(CH$_2$)$_3$—COCF$_3$ | 93% (100 μM) | 6.9 | 0.77 |
| 23.6 | 3-BnO-C$_6$H$_4$—O—(CH$_2$)$_4$—COCF$_3$ | 97% (100 μM) | 6.6 | 0.47 |
| 23.7 | 3-BnO-C$_6$H$_4$—O—(CH$_2$)$_5$—COCF$_3$ | 96% (100 μM) | 0.47 | 0.052 |
| 23.8 | 2-BnO-C$_6$H$_4$—O—(CH$_2$)$_3$—COCF$_3$ | 46% (100 μM) | 34.6 | 2.28 |
| 23.9 | 2-BnO-C$_6$H$_4$—O—(CH$_2$)$_4$—COCF$_3$ | 97% (100 μM) | 0.66 | 0.046 |
| 23.10 | 2-BnO-C$_6$H$_4$—O—(CH$_2$)$_5$—COCF$_3$ | 95% (100 μM) | 7.9 | 0.553 |
| 23.11 | C$_6$H$_5$—O—(CH$_2$)$_3$—COCF$_3$ | 79% (100 μM) | 11.2 | 1.2 |
| 23.12 | C$_6$H$_5$—O—(CH$_2$)$_4$—COCF$_3$ | 65% (100 μM) | 25.4 | 2.8 |
| 24.1 | HO—C$_6$H$_4$—O—(CH$_2$)$_3$—COCF$_3$ | 68% (100 μM) | 14.9 | 1.7 |
| 24.2 | HO—C$_6$H$_4$—O—(CH$_2$)$_4$—COCF$_3$ | 60% (100 μM) | 23.2 | 2.6 |
| 24.3 | HO—C$_6$H$_4$—O—(CH$_2$)$_5$—COCF$_3$ | 86% (100 μM) | 11.4 | 0.80 |

TABLE 1-continued
FAAH inhibitors of compound formula I (R—X—Y).
| Compound number | Structure I | % Inhibition (Concentration) | IC$_{50}$ (µM) | Ki (µM) |
|---|---|---|---|---|
| 24.4 | 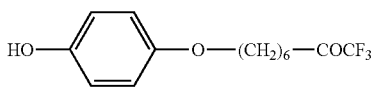 | 89% (100 µM) | 0.76 | 0.054 |
| 24.5 | 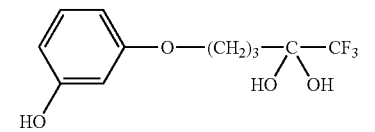 | 79% (100 µM) | 22.8 | 2.5 |
| 24.6 | 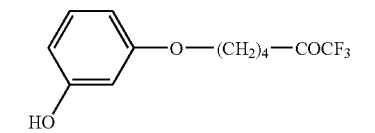 | 85% (100 µM) | 29.4 | 2.07 |
| 24.7 | 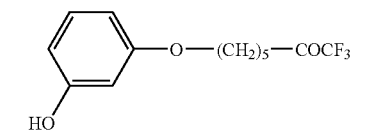 |  | 5.02 | 0.44 |
| 24.8 | 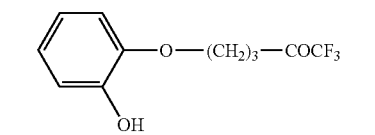 | 43% (100 µM) | 137.5 | 15.3 |
| 24.9 | 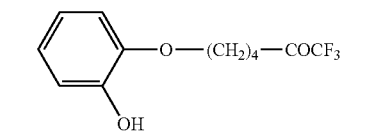 | 60% (100 µM) | 23.9 | 1.6 |
| 24.10 | 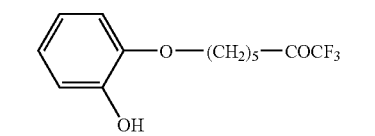 | 82% (100 µM) | 26.2 | 1.8 |
| 27.1 | 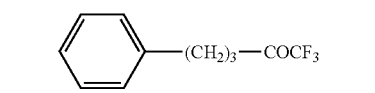 | 46% (100 µM) | 69.4 | 4.6 |
| 27.2 | 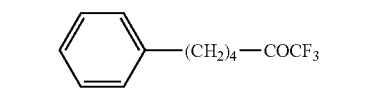 | 53% (100 µM) | 18.8 | 2.1 |
| 27.3[c] | 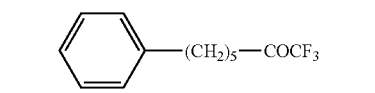 | 83% (100 µM) | 11.1 | 1.23 |
| 27.4 | 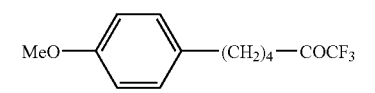 | 82% (100 µM) | 6.9 | 0.60 |
| 30 | 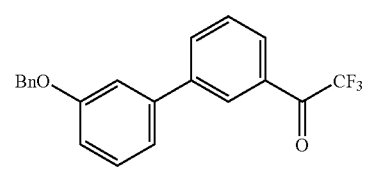 [SMILES: O=C(c1cccc(-c2cccc(OCc3ccccc3)c2)c1)C(F)(F)F] | 33% (100 µM) |  |  |

TABLE 1-continued
FAAH inhibitors of compound formula I (R—X—Y).
| Compound number | Structure I | % Inhibition (Concentration) | IC$_{50}$ (μM) | Ki (μM) |
|---|---|---|---|---|
| 35 | 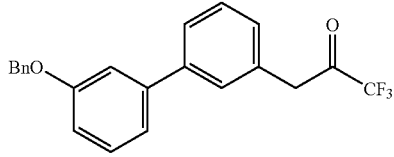 [SMILES: O=C(Cc1cccc(-c2cccc(OCc3ccccc3)c2)c1)C(F)(F)F] | 54% (100 μM) | | |
| 39.1[d] | 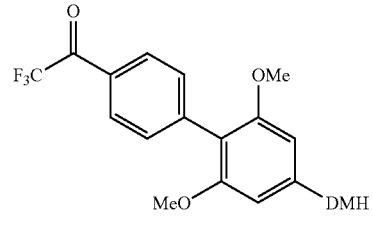 | | | |
| 39.2 | 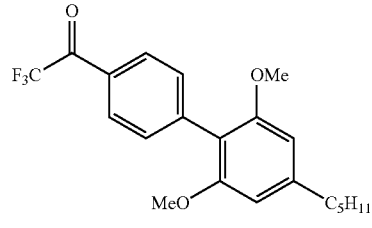 | 57% (100 μM) | | |
| 39.3 | 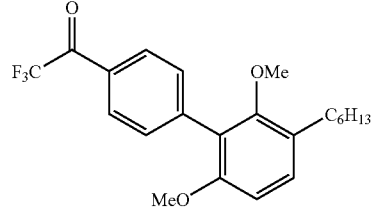 | | | |
| 39.4 | 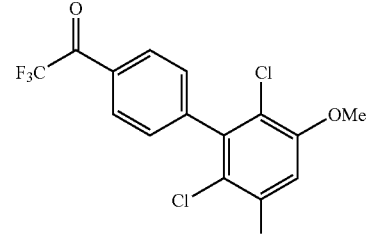 | | | |
| 40.1 | 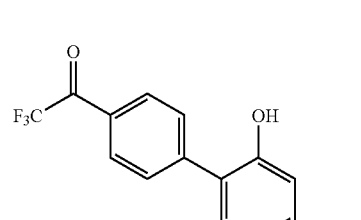 | 36% (100 μM) | | |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 40.3 | | 81% (100 μM) | | |
| 46.1 | | | | |
| 46.2 | | | | |
| 46.3 | | | | |
| 48.1 | | 25% (100 μM) | | |
| 48.2 | | 84% (100 μM) | 4.0 | 1.2 |
| 48.3 | | 36% (100 μM) | | |
| 48.4 | | 56% (100 μM) | | |
| 48.5 | | | | |

TABLE 1-continued

FAAH inhibitors of compound formula I (R—X—Y).

| Compound number | Structure I | % Inhibition (Concentration) | IC$_{50}$ (µM) | Ki (µM) |
| --- | --- | --- | --- | --- |
| 48.6 | | 84% (100 µM) | | |
| 52.1 | | | | |
| 52.2 | | 64% (100 µM) | | |
| 52.3 | | 41% (100 µM) | | |
| 52.4 | | | | |
| 53.1 | | 23% (100 µM) | | |
| 53.2 | | 15% (100 µM) | | |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 53.3 | | 89% (100 μM) | | |
| 53.4 | | 25% (100 μM) | | |
| 57.1 | | | | |
| 57.2 | | 89% (100 μM) | | |
| 59.1 | | | | |
| 59.2 | | | | |
| 65.1 | | | | |
| 65.2 | | 96% (100 μM) | 0.12 | 0.008 |
| 66 | | 97% (100 μM) | 0.10 | 0.006 |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 73.1 | | 94% (100 μM) | 0.025 | 0.002 |
| 73.2 | | 93% (100 μM) | 0.021 | 0.002 |
| 74.1 | | 96% (100 μM) | 0.015 | 0.001 |
| 74.2 | | 92% (100 μM) | 0.039 | 0.003 |
| 78 | | 56% (100 μM) | | |
| 81 | | 24% (100 μM) | | |
| 83.1 | | 42% (100 μM) | | |
| 83.2 | | 91% (100 μM) | 11.6 | |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 83.3 | | 87% (100 μM) | | 10.9 |
| 83.4 | | | | |
| 83.5 | | | | |
| 83.6 | | | | |
| 83.7 | | | | |
| 83.8 | | | | |
| 83.9 | | | | |

TABLE 1-continued

FAAH inhibitors of compound formula I (R—X—Y).

| Compound number | Structure I | % Inhibition (Concentration) | IC$_{50}$ (μM) | Ki (μM) |
| --- | --- | --- | --- | --- |
| 84 | (4-hydroxyphenoxy)-(CH$_2$)$_4$-N-saccharin sulfonamide structure | 92% (100 μM) | 9.1 | 0.9 |
| 87.1 | 3-BnO-phenoxy-(CH$_2$)$_4$-C(O)-C(O)-OEt | 100% (100 μM) | | |
| 87.2 | phenoxy-(CH$_2$)$_4$-C(O)-C(O)-OEt | | | |
| 87.3 | 4-BnO-phenoxy-(CH$_2$)$_4$-C(O)-C(O)-OEt | | | |
| 87.4 | phenoxy-(CH$_2$)$_5$-C(O)-C(O)-OEt | 100% (100 μM) | 0.29 | 0.09 |
| 87.7 | phenoxy-(CH$_2$)$_6$-C(O)-C(O)-OEt | | | |
| 89.1 | 3-BnO-phenoxy-(CH$_2$)$_4$-CF$_2$-C(O)-Me | 79% (100 nM) | 0.27 | 0.08 |
| 89.2 | phenoxy-(CH$_2$)$_4$-CF$_2$-C(O)-Me | 98% (100 μM) | | |
| 89.4 | phenoxy-(CH$_2$)$_5$-CF$_2$-C(O)-CH$_3$ | 87% (100 μM) | 0.23 | 0.07 |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 89.7 | | | 0.031 | 0.009 |
| 89.8 | | | | |
| 89.9 | | 52% (100 nM) | 0.077 | 0.024 |
| 89.9 Hydrate form | | 63% (100 nM) | 0.039 | 0.012 |
| 89.10 | | 33% (100 nM) | 0.164 | 0.052 |
| 89.11 | | 85% (100 nM) | 0.024 | 0.007 |
| 89.12 | | 20% (100 nM) | 0.31 | 0.10 |
| 89.13 | | | 0.038 | |
| 89.14 | | | | |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 91.1 | | 86% (100 μM) | 15.0 | 4.6 |
| 91.2 | | | | |
| 91.3 | | | | |
| 91.4 | | | | |
| 91.5 | | 79% (100 μM) | | |
| 91.6 | | | | |
| 93.1 | | 41% (100 nM) | 0.21 | 0.065 |
| 93.2 | | | | |
| 93.5 | | 97% (100 μM) | 1.67 | 0.53 |

TABLE 1-continued

FAAH inhibitors of compound formula I (R—X—Y).

| Compound number | Structure I | % Inhibition (Concentration) | IC$_{50}$ (μM) | Ki (μM) |
|---|---|---|---|---|
| 93.7 | | 94% (100 μM) | | |
| 93.8 | | | | |
| 93.9 | | | | |
| 96.1 | | 86% (100 μM) | | |
| 96.2 | | 61% (100 μM) | | |

[a] encompassed in Makriyannis et al., US2002/0091153 and included here for the purpose of comparison.
[b] The group BnO— is Ph-CH$_2$—O— where Ph is Phenyl.
[c] encompassed in Boger, D. L et al., Bioorg. Med. Chem. Lett., 1999, 9, 265-270 and included here for the purpose of comparison.
[d] The group DMH is as shown on Scheme 8.

Synthesis of compounds of compound formula I.

1. Synthesis of Sulfonyl Fluorides.

Phenylalkylsulfonyl fluorides 4.1, 4.2, and 4.3 (shown in Scheme 1) were synthesized by a method depicted in Scheme 1 starting from commercially available phenylalkyl alcohols 1.1, 1.2, and 1.3.

Scheme 1

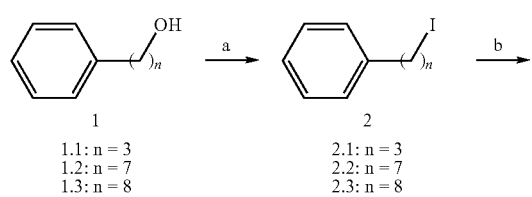

1
1.1: n = 3
1.2: n = 7
1.3: n = 8

2
2.1: n = 3
2.2: n = 7
2.3: n = 8

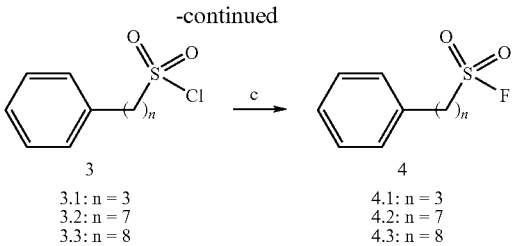

3
3.1: n = 3
3.2: n = 7
3.3: n = 8

4
4.1: n = 3
4.2: n = 7
4.3: n = 8

Reagents and conditions: (a) PPh$_3$, imidazole, 12, MeCN/Et$_2$O, 0° C. to r t, 72-85%; (b) (i) t-BuLi, Et$_2$O/pentane, −78° C., (ii) SO$_2$Cl$_2$, −78° C., 19-23%; (c) NH$_4$F, acetone, reflux, 91-93%.

Experimental Procedures:

Phenylalkyl Iodides (2).

A round bottom flask was charged with phenylalkyl alcohol 1 (1 equiv.), acetonitrile/diethyl ether mixture (1:2), triphenyl phosphine (1.3 equiv.), imidazole (1.3 equiv.), and iodine (1.3 equiv.). The solution was blanketed with argon and capped and the reaction stirred for 4-5 hours at room temperature. The resulting mixture diluted with diethyl ether, washed with water, aqueous sodium thiosulfate, and brine, dried (MgSO$_4$) and evaporated. Purification by flash column chromatography on silica gel (10% diethyl ether-hexane) gave phenylalkyl iodide 2 in 72-85% yield.

Phenylalkylsulfonyl Chlorides (3).

A solution of phenylalkyl iodide 2 (1 equiv.) in a mixture of dry n-pentane/diethyl ether (3:2) was cooled to −78° C. under argon, and t-BuLi (2.2 equiv., using a 1.7 M solution of t-BuLi in hexane) was added dropwise over a 2-min period. The mixture was stirred for 10 min at −78° C. and then was transferred by cannula to a cooled (−78° C.) and dry solution of SO$_2$Cl$_2$ in n-pentane over a 20-min period. Following the addition, the reaction mixture was stirred for 1 hour at −78° C. and then allowed to warm to room temperature over a 3 hours period. The reaction mixture was quenched with dropwise addition of water, then diluted with diethyl ether and the organic phase was separated. The aqueous phase was extracted with diethyl ether, the combined organic layer was dried (MgSO$_4$) and the solvent was evaporated. Purification by flash column chromatography on silica gel gave phenylalkylsulfonyl chloride 3 in 19-23% yield.

Phenylalkylsulfonyl Fluorides (4).

To a stirred solution of phenylalkylsulfonyl chloride 3 (1 equiv.) in dry acetone, was added anhydrous NH$_4$F (2 equiv.) and the mixture refluxed for 2 hours. The reaction mixture was cooled to room temperature, the solvent was evaporated, and the residue obtained was dissolved in diethyl ether. The ethereal solution was successively washed with water and brine, dried (MgSO$_4$) and concentrated under reduced pressure. Purification by flash column chromatography on silica gel gave phenylalkylsulfonyl fluoride 4 in 91-93% yield.

Selected Data of Synthesized Phenylalkylsulfonyl Fluorides (4):

3-Phenyl-propanesulfonyl fluoride (4.1). $^1$H NMR (200 MHz, CDCl$_3$) δ 7.46-7.15 (m, 5H), 3.40-3.27 (m, 2H), 2.82 (t, J=7.3 Hz, 2H), 2.40-2.21 (m, 2H); mass spectrum m/z (relative intensity) 202 (M$^+$, 27), 91 (100).

7-Phenyl-heptanesulfonyl fluoride (4.2). Mass spectrum m/z (relative intensity) 258 (M$^+$, 10), 105 (9), 91 (100).

8-Phenyl-octanesulfonyl fluoride (4.6). $^1$H NMR (200 MHz, CDCl$_3$) δ 7.45-7.05 (m, 5H), 3.40-3.25 (m, 2H), 2.60 (t, J=7.1 Hz, 2H), 2.10-1.20 (m, 12H).

Sulfonyl fluorides 13.1, 13.2, 13.3, 13.4, 14.1, 14.2, 14.3, 14.4 (shown in Scheme 2) were synthesized by a method depicted in Scheme 2 starting from commercially available 2- or 3- or 4-anisaldehyde and the appropriate phenoxyalkyl bromide.

Scheme 2

5
5.1: n = 4
5.2: n = 2

6
6.1: n = 4
6.2: n = 2

7
7.1: $R_1$ = OMe, $R_2$ = H, $R_3$ = H, n = 4
7.2: $R_1$ = H, $R_2$ = OMe, $R_3$ = H, n = 4
7.3: $R_1$ = H, $R_2$ = H, $R_3$ = OMe, n = 4
7.4: $R_1$ = OMe, $R_2$ = H, $R_3$ = H, n = 2

8
8.1: $R_1$ = OMe, $R_2$ = H, $R_3$ = H, n = 4
8.2: $R_1$ = H, $R_2$ = OMe, $R_3$ = H, n = 4
8.3: $R_1$ = H, $R_2$ = H, $R_3$ = OMe, n = 4
8.4: $R_1$ = OMe, $R_2$ = H, $R_3$ = H, n = 2

9
9.1: $R_1$ = OH, $R_2$ = H, $R_3$ = H, n = 4
9.2: $R_1$ = H, $R_2$ = OH, $R_3$ = H, n = 4
9.3: $R_1$ = H, $R_2$ = H, $R_3$ = OH, n = 4
9.4: $R_1$ = OH, $R_2$ = H, $R_3$ = H, n = 2

10
10.1: $R_1$ = OBn, $R_2$ = H, $R_3$ = H, n = 4
10.2: $R_1$ = H, $R_2$ = OBn, $R_3$ = H, n = 4
10.3: $R_1$ = H, $R_2$ = H, $R_3$ = OBn, n = 4
10.4: $R_1$ = OBn, $R_2$ = H, $R_3$ = H, n = 2

11
11.1: $R_1$ = OBn, $R_2$ = H, $R_3$ = H, n = 4
11.2: $R_1$ = H, $R_2$ = OBn, $R_3$ = H, n = 4
11.3: $R_1$ = H, $R_2$ = H, $R_3$ = OBn, n = 4
11.4: $R_1$ = OBn, $R_2$ = H, $R_3$ = H, n = 2

12
12.1: $R_1$ = OBn, $R_2$ = H, $R_3$ = H, n = 4
12.2: $R_1$ = H, $R_2$ = OBn, $R_3$ = H, n = 4
12.3: $R_1$ = H, $R_2$ = H, $R_3$ = OBn, n = 4
12.4: $R_1$ = OBn, $R_2$ = H, $R_3$ = H, n = 2

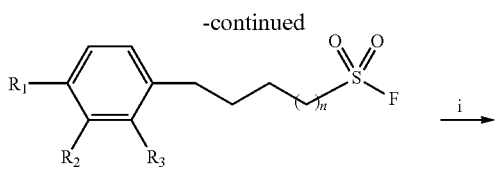

13

13.1: $R_1$ = OBn, $R_2$ = H, $R_3$ = H, n = 4
13.2: $R_1$ = H, $R_2$ = OBn, $R_3$ = H, n = 4
13.3: $R_1$ = H, $R_2$ = H, $R_3$ = OBn, n = 4
13.4: $R_1$ = OBn, $R_2$ = H, $R_3$ = H, n = 2

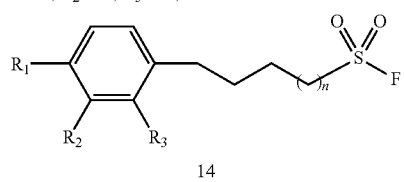

14

14.1: $R_1$ = OH, $R_2$ = H, $R_3$ = H, n = 4
14.2: $R_1$ = H, $R_2$ = OH, $R_3$ = H, n = 4
14.3: $R_1$ = H, $R_2$ = H, $R_3$ = OH, n = 4
14.4: $R_1$ = OH, $R_2$ = H, $R_3$ = H, n = 2

Reagents and conditions: (a) $Ph_3P$, PhH, reflux, 85-87%; (b) $(Me_3Si)_2N^-K^+$, THF, 0° C., then 2- or 3- or 4-anisaldehyde 91-93%; (c) $H_2$, Pd/C, AcOEt, 30 psi, r t, 6 h, 95-96% (d) $BBr_3$, $CH_2Cl_2$, −30° C. to r t, 2 h, 90-93% (e) $K_2CO_3$, acetone, BnBr, reflux, 6 h, 76-78%; (f) $Na_2SO_3$, $EtOH/H_2O$, reflux, 6 h or m. w, see text; (g) $SOCl_2$, PhH/DMF, $N_2$, 50° C., 3 h, 37-40% from 10; (h) $NH_4F$, acetone, $N_2$, reflux, 2 h, 91-93%; (i) $BF_3 \cdot OEt_2$, $HS(CH_2)_2SH$, $N_2$, r t, 1 h, 68-70%.

Experimental Procedures:

6-Phenoxyhexyltriphenylphosphonium bromide 6.1.

A mixture of 6-phenoxyhexyl bromide 5.1 (2.8 g, 10.9 mmol) and triphenylphosphine (314 g, 12 mmol) in anhydrous benzene (100 mL), under an argon atmosphere, was refluxed for two days. The reaction mixture was allowed to cool to room temperature and the precipitating product (6.1) was isolated by filtration under reduced pressure and washed with anhydrous diethyl ether (4.75 g, 84% yield). White solid, m p 143-145° C.

$^1$H NMR (500 MHz, $CDCl_3$) δ 7.89-7.85 (m as dd, 6H), 7.81-7.75 (m as td, 3H), 7.71-7.67 (m as td, 6H), 7.25 (t, J=7.7 Hz, 2H), 6.91 (t, J=7.7 Hz, 1H), 6.84 (d, J=7.7 Hz, 2H) 3.95-3.85 (m and t overlapping, especially 3.90, t, J=6.3 Hz, 4H), 1.79-1.65 (m, 6H), 1.49 (quintet, J=7.7 Hz; 2H).

4-Phenoxybutyltriphenylphosphonium bromide 6.2.

The title compound was synthesized as in 6.1 using 4-phenoxybutyl bromide (5.2) (22.0 g, 95.9 mmol) and triphenylphosphine (27.6 g, 105.5 mmol) in anhydrous benzene (50 mL), to give 6.1 (40.0 g, 85% yield). White solid, m p 185-186° C.

$^1$H NMR (500 MHz, $CDCl_3$) δ 7.88-7.84 (m as dd, 6H), 7.78-7.76 (m as td, 3H), 7.68-7.65 (m, 6H), 7.25 (t, J=7.7 Hz, 2H), 6.92 (t, J=7.7 Hz, 1H), 6.82 (d, J=7.7 Hz, 2H), 4.09 (t, J=4.5 Hz, 2H), 4.04-3.98 (m, 2H), 2.25 (quintet, J=6.4 Hz, 2H), 1.92-1.86 (m, 2H).

1-(4-Methoxyphenyl)-7-phenoxy-1-heptene (7.1).

To a suspension of 6-phenoxyhexyltriphenylphosphonium bromide (6.1) (4.60 g, 8.86 mmol) in dry THF (80 mL) at 0° C., under an argon atmosphere was added potassium bis (trimethylsilyl)amide (1.76 g, 8.86 mmol). The resulting slurry was stirred for 5 min at the same temperature and then a solution of 4-methoxybenzaldehyde (0.61 g, 4.46 mmol) in dry THF (10 mL) was added. The reaction mixture was stirred for an additional 10 min and quenched with saturated aqueous $NH_4Cl$ (20 mL). The resulting mixture was warmed to room temperature, diluted with $Et_2O$ (100 mL), the organic phase was separated and the aqueous phase extracted with $Et_2O$. The combined organic layer was washed with brine, dried over $MgSO_4$ and the solvent evaporated under reduced pressure. The residue obtained was purified through a short column of silica gel, eluting with 5% $Et_2O$-hexane, to give the product 7.1 (1.21 g, 92% yield, predominantly cis, cis:trans=96:4) as a colorless liquid.

$^1$H NMR (500 MHz, $CDCl_3$) δ 7.27 (t, J=7.5 Hz, 2H), 7.21 (d, J=8.7 Hz, 2H), 6.92 (t, J=7.5 Hz, 1H), 6.91-6.86 (m, overlapping signals, 4H), 6.35 (d, J=11.5 Hz, 1H,), 5.57 (dt, J=11.5 Hz, J=7.5 Hz, 1H), 3.94 (t, J=6.0 Hz, 2H), 3.81 (s, 3H), 2.41-2.20 (m, 2H), 1.78 (quintet, J=6.7 Hz, 2H), 1.58-1.48 (m, 4H).

1-(3-Methoxyphenyl)-7-phenoxy-1-heptene (7.2) was synthesized as described in 7.1 using 6.1 (3.20 g 6.16 mmol), dry THF (30 mL), potassium bis(trimethylsilyl)amide (1.23 g, 6.16 mmol), and 3-methoxybenzaldehyde (0.28 g, 2.05 mmol). The title compound (7.2) was isolated as a colorless liquid after purification by flash column chromatography (0.564 g, 93% yield, predominantly cis, cis:trans=95:5).

$^1$H NMR (500 MHz, $CDCl_3$) δ 7.27-7.21 (m, 3H), 6.92 (t, J=7.0 Hz, 1H), 6.90-6.86 (m, 3H), 6.81 (t, J=1.5 Hz, 1H), 6.78 (dd, J=8.5 Hz, J=1.5 Hz, 1H), 6.39 (d, J=11.7 Hz, 1H), 5.67 (dt, J=11.7 Hz, J=7.5 Hz, 1H), 3.94 (t, J=6.5 Hz, 2H), 3.80 (s, 3H), 2.37 (q, J=6.5, 2H), 1.78 (quintet, J=6.5 Hz, 2H), 1.56-1.48 (m, 4H).

1-(2-Methoxyphenyl)-7-phenoxy-1-heptene (7.3) was synthesized as described in 7.1 using 6.1 (2.0 g, 3.85 mmol), dry THF (30 mL), potassium bis(trimethylsilyl)amide (0.77 g, 3.85 mmol), and 2-methoxybenzaldehyde (0.20 g, 1.47 mmol). The title compound (7.3) was isolated as a colorless liquid after purification by flash column chromatography (0.396 g, 91% yield, predominantly cis, cis:trans=93:7).

$^1$H NMR (500 MHz, $CDCl_3$) δ 7.29-7.21 (m, 4H), 6.94-6.87 (m, 5H), 6.52 (d, J=11.2 Hz, 1H), 5.73 (di, J=11.2 Hz, J=7.5 Hz, 1H), 3.93 (t, J=6.7 Hz, 2H), 3.83 (s, 3H), 2.28 (m as q, J=7.2 Hz, 2H), 1.76 (quintet, J=7.2 Hz, 2H), 1.53-1.46 (m, 4H).

1-(4-Methoxyphenyl)-7-phenoxy-1-pentene (7.4) was synthesized as described in 7.1 using 6.2 (29.0 g, 58.8 nmol), dry THF (200 mL), potassium bis(trimethylsilyl)amide (11.7 g, 58.8 mmol) and 4-methoxybenzaldehyde (2.9 g, 14.7 mmol). The title compound (7.4) was isolated as a colorless liquid after purification by flash column chromatography (3.69 g, 93% yield, predominantly cis, cis:trans=96:4).

$^1$H NMR (500 MHz, $CDCl_3$) δ 7.26 (t, J=7.5 Hz, 2H), 7.22 (d, J=8.7 Hz, 2H), 6.92 (t, J=7.5 Hz, 1H), 6.87 (d, J=7.5 Hz, 2H), 6.85 (d, J=8.7 Hz, 2H), 6.39 (d, J=11.5 Hz, 1H), 5.60 (dt, J=11.5 Hz, J=7.0 Hz, 1H), 3.98 (t, J=6.0 Hz, 2H), 3.80 (s, 3H), 2.51 (m as qd, J=7.5 Hz, J=2.1 Hz, 2H), 1.94 (quintet, J=6.7 Hz 2H).

1-(4-Methoxyphenyl)-7-phenoxy-heptane (8.1).

To a stirred solution of 7.1 (1.19 g, 4.03 mmol) in AcOEt (40 mL) at room temperature was added 10% Pd/C (0.18 g, 15% w/w) and the resulting suspension was hydrogenated (30 psi, 6 h). The catalyst was removed by filtration through celite and the filtrate was evaporated under reduced pressure to give the title compound (8.1) (1.14 g, 95% yield) as a white solid (m p 32-34° C.).

$^1$H NMR (500 MHz, $CDCl_3$) δ 7.30 (t, J=8.5 Hz, 2H), 7.11 (d, J=8.2 Hz, 2H), 6.95 (t, J=8.5 Hz, 1H), 6.92 (d, J=8.5 Hz 2H), 6.84 (d, J=8.2 Hz, 2H), 3.97 (t, J=6.7 Hz, 2H), 3.81, (s, 3H) 2.57 (t, J=7.5 Hz, 2H), 1.78 (quintet, J=6.7 Hz, 2H), 1.62 (quintet, J=7.5 Hz, 2H), 1.48 (quintet, J=7.5 Hz, 2H), 1.44-1.34 (m, 4H).

1-(3-Methoxyphenyl)-7-phenoxy-heptane (8.2) was synthesized as described in 8.1 using 7.2 (0.55 g, 1.86 mmol), AcOEt (20 mL), and 10% Pd/C (0.080 g, 15% w/w). The title compound (8.2) was isolated as a colorless viscous liquid (0.53 g, 0.96% yield).

$^1$H NMR (500 MHz, CDCl$_3$) δ 7.27 (t, J=7.0 Hz, 2H), 7.19 (t, J=7.4 Hz, 1H), 6.92 (t, J=7.0 Hz, 1H), 6.89 (d, J=7.0 Hz, 2H), 6.77 (d, J=7.4 Hz, 1H), 6.73-6.71 (m, 2H), 3.94 (t, J=6.5 Hz, 2H), 3.79 (s, 3H), 2.58 (t, J=7.5 Hz, 2H), 1.77 (quintet, J=6.7 Hz, 2H), 1.62 (quintet, J=7.2 Hz, 2H), 1.50-1.42 (m, 2H), 1.42-1.34 (m, 4H).

1-(2-Methoxyphenyl)-7-phenoxy-heptane (8.3) was synthesized as described in 8.1 using 7.3 (0.35 g, 1.18 mmol), AcOEt (20 mL), and 10% Pd/C (0.050 g, 14% w/w). The title compound (8.3) was isolated as a colorless viscous liquid (0.33 g, 95% yield).

$^1$H NMR (500 MHz, CDCl$_3$)-7.27 (t, J=7.5 Hz, 2H), 7.16 (t, J=7.5 Hz, 1H), 7.12 (d, J=7.5 Hz, 1H), 6.94-6.83 (m, 5H), 3.95 (t, J=6.5 Hz, 2H), 3.81 (s, 3H), 2.60 (t, J=7.7, 2H), 1.78 (quintet, J=7.0 Hz, 2H), 1.59 (quintet, J=7.0 Hz, 2H), 1.48-1.43 (m, 2H), 1.42-1.38 (m, 4H).

1-(4-Methoxyphenyl)-5-phenoxy-pentane (8.4) was synthesized as described in 8.1 using 7.4 (3.67 g, 13.69 mmol), AcOEt (100 mL), and 10% Pd/C (0.550 g, 15% w/w). The title compound (8.3) was isolated as a white solid (m p 32-34° C.) in 95% yield (3.52 g).

$^1$H NMR (500 MHz, CDCl$_3$) δ 7.27 (t, J=7.5 Hz, 2H), 7.09 (d, J=8.5 Hz, 2H), 6.92 (t, J=7.5 Hz, 1H), 6.88 (d, J=7.5 Hz, 2H), 6.82 (d, J=8.5 Hz, 2H), 3.94 (t, J=6.5 Hz, 2H), 3.78 (s, 3H), 2.58 (t, J=7.7 Hz, 2H), 1.80 (quintet, J=6.7 Hz, 2H), 1.66 (quintet, J=7.0 Hz, 2H), 1.49 (quintet, J=7.5 Hz, 2H).

7-Bromo-1-(4-hydroxy-phenyl)-heptane (9.1).

To a stirred solution of 8.1 (1.1 g, 3.69 mmol) in anhydrous CH$_2$Cl$_2$ (40 mL), at −30° C., under an argon atmosphere was added BBr$_3$ (8 mL, 8 mmol, using a 1M solution in CH$_2$Cl$_2$) and the mixture gradually warmed to room temperature (2 h). Unreacted boron tribromide was destroyed by addition of aqueous saturated NaHCO$_3$ solution (10 mL) to the reaction mixture at 0° C. The resulting mixture was warmed to room temperature and diluted with Et$_2$O (40 mL). The organic layer was separated and the aqueous phase extracted with Et$_2$O. The combined organic layer was washed with brine, dried over MgSO$_4$ and the solvent evaporated under reduced pressure. The residue obtained was chromatographed through a short column of silica gel, eluting with 20% Et$_2$O-hexane to give 8.1 (0.930 g, 93% yield) as a viscous liquid.

$^1$H NMR (500 MHz, CDCl$_3$) δ 7.03 (d, J=8.5 Hz, 2H), 6.74 (d, J=8.5 Hz, 2H), 4.59 (br s, 1H), 3.34 (t, J=6.7 Hz, 2H), 2.53 (t, J=7.7 Hz, 2H), 1.84 (quintet, J=7.0 Hz, 2H), 1.57 (quintet, J=7.5 Hz, 2H), 1.46-1.38 (m, 2H), 1.36-1.31 (m, 4H).

7-Bromo-1-(3-hydroxy-phenyl)-heptane (9.2) was synthesized as in 9.1 using 8.2 (0.50 g, 1.68 mmol), in anhydrous CH$_2$Cl$_2$ (16 mL), and BBr$_3$ (1M solution in CH$_2$Cl$_2$, 3.7 mL, 3.7 mmol). The title compound (9.2) was isolated as a viscous liquid after purification by flash column chromatography (0.420 g, 92% yield).

$^1$H NMR (500 MHz, CDCl$_3$) δ 7.14 (t, J=8.0 Hz, 1H), 6.75 (d, J=8.0 Hz, 1H), 6.66-6.63 (d and dd overlapping, 2H), 4.67 (br s, 1H), 3.40 (t, J=6.7 Hz, 2H), 2.56 (t, J=7.7 Hz, 2H), 1.85 (quintet, J=7.0 Hz, 2H), 1.62 (quintet, J=7.5 Hz, 2H), 1.46-1.38 (m, 2H), 1.36-1.32 (m, 4H).

7-Bromo-1-(2-hydroxy-phenyl)-heptane (9.3) was synthesized as in 9.1 using 8.3 (0.30 g, 1.01 mmol) in anhydrous CH$_2$Cl$_2$ (10 mL), and BBr$_3$ (1M solution in CH$_2$Cl$_2$, 2.2 mL, 2.2 mmol). The title compound (9.3) was isolated as a viscous liquid after purification by flash column chromatography (0.247 g, 90% yield).

$^1$H NMR (500 MHz, CDCl$_3$) δ 7.11 (dd, J=7.5 Hz, J=1.5 Hz, 1H), 7.07 (td, J=7.5 Hz, J=1.5 Hz, 1H), 6.87 (td, J=7.5 Hz, J=1.5 Hz, 1H), 6.75 (dd, J=7.5 Hz, J=1.5 Hz, 1H), 4.62 (br s, 1H), 3.40 (t, J=7.0 Hz, 2H), 2.60 (t, J=8.0 Hz, 2H), 1.85 (quintet, J=6.7 Hz, 2H), 1.62 (quintet, J=7.2 Hz, 2H), 1.4 (quintet, J=7.5 Hz, 2H), 1.40-1.35 (m, 4H).

5-Bromo-1-(4-hydroxy-phenyl)-pentane (9.4) was synthesized as in 9.1 using 8.4 (3.43 g, 12.7 mmol) in anhydrous CH$_2$Cl$_2$ (120 mL), and BBr$_3$ (1M solution in CH$_2$Cl$_2$, 32 mL, 32 mmol). The title compound (9.4) was isolated as a viscous liquid after purification by flash column chromatography (2.84 g, 92% yield).

$^1$H NMR (500 MHz, CDCl$_3$) δ 7.04 (d, J=8.7 Hz, 2H), 6.75 (d, J=8.7 Hz, 2H), 4.68 (br s, 1H), 3.34 (t, J=6.7 Hz, 2H), 2.55 (t, J=7.7 Hz, 2H), 1.88 (quintet, J=7.7 Hz, 2H), 1.60 (quintet, J=7.7 Hz, 2H), 1.46 (quintet, J=7.5 Hz, 2H).

7-Bromo-1-(4-benzyloxy-phenyl)-heptane (10.1).

To a stirred solution of 9.1 (0.9 g, 3.32 mmol) in anhydrous acetone (40 mL), was added anhydrous K$_2$CO$_3$ (1.38 g, 10 mmol) and benzyl bromide (0.624 g, 3.65 mmol) and the mixture was refluxed for 6 h. The reaction mixture was cooled to room temperature, diluted with acetone and solid materials were filtered off. The filtrate was evaporated under reduced pressure and the residue obtained was dissolved in diethyl ether (50 mL). The ethereal solution was washed with water and brine, dried (MgSO$_4$) and evaporated. Purification by flash column chromatography on silica gel (5% Et$_2$O-hexane) afforded 10.1 (0.938 g, 78% yield) as a white solid (m p 32-34° C.).

$^1$H NMR (500 MHz, CDCl$_3$) δ 7.43 (d, J=7.0 Hz, 2H), 7.38 (t, J=7.0 Hz, 2H), 7.32 (t, J=7.0 Hz 1H), 7.08 (d, J=8.7 Hz, 2H) 6.90 (d, J=8.7 Hz 2H), 5.04 (s, 2H), 3.34 (t, J=7.0 Hz, 2H), 2.54 (t, J=7.7 Hz, 2H), 1.85 (quintet, H=7.5 Hz, 2H), 1.58 (quintet, J=7.5 Hz, 2H), 1.46-1.38 (m, 2H), 1.37-1.30 (m, 4H).

7-Bromo-1-(3-benzyloxy-phenyl)-heptane (10.2) was prepared as in 10.1 using 9.2 (0.4 g, 1.48 mmol), K$_2$CO$_3$ (0.612 g, 4.44 mmol) and benzyl bromide (0.278 g, 1.63 mmol). The title, compound (10.2) was isolated as a viscous liquid after purification by flash column chromatography (0.411 g, 77% yield).

$^1$H NMR (500 MHz, CDCl$_3$) δ 7.44 (d, J=7.5 Hz, 2H), 7.39 (t, J=7.5 Hz, 2H), 7.32 (t, J=7.5 Hz 1H), 7.19 (t, J=7.2 Hz, 1H) 6.83-6.77 (m, 3H), 5.05 (s, 2H), 3.40 (t, J=6.77 Hz, 2H), 2.56 (t, J=7.7 Hz, 2H), 1.84 (quintet, J=7.0 Hz, 2H), 1.60 (quintet, J=7.7 Hz, 2H), 1.42 (quintet, J=7.0 Hz, 2H), 1.35-1.32 (m, 4H).

7-Bromo-1-(2-benzyloxy-phenyl)-heptane (10.3) was prepared as in 10.1 using 9.3. (0.23 g, 0.85 mmol), K$_2$CO$_3$ (0.352 g, 2.55 mmol) and benzyl bromide (0.16 g, 0.935 mmol). The title compound (10.3) was isolated as a viscous liquid after purification by flash column chromatography (0.24 g, 78% yield).

$^1$H NMR (500 MHz, CDCl$_3$) δ 7.44 (d, J=7.5 Hz, 2H), 7.39 (t, J=7.5 Hz, 2H), 7.32 (t, J=7.5 Hz 1H), 7.18-7.13 (m, 2H), 6.92-6.88 (m, 2H), 5.08 (s, 2H), 3.37 (t, J=7.0 Hz, 2H), 2.67 (t, J=7.7 Hz, 2H), 1.82 (quintet, J=7.2 Hz, 2H), 1.62 (quintet, J=7.5 Hz, 2H), 1.39 (quintet, J=7.7 Hz, 2H), 1.36-1.32 (m, 4H).

5-Bromo-1-(4-benzyloxy-phenyl)-pentane (10.4) was prepared as in 10.1 using 9.4 (2.99 g, 12.3 mmol), K$_2$CO$_3$ (4.24 g, 30.75 mmol) and benzyl bromide (2.31 g, 13.53 mmol). The title compound (10.4) was isolated as a white semi-solid after purification by flash column chromatography (3.11 g, 76% yield).

$^1$H NMR (500 MHz, CDCl$_3$) δ 7.42 (d, J=7.5 Hz, 2H), 7.37 (t, J=7.5 Hz, 2H), 7.31 (t, J=7.5 Hz 1H), 7.08 (d, J=8.5 Hz,

2H), 6.90 (d, J=8.5 Hz, 2H), 5.03 (s, 2H), 3.39 (t, J=6.7 Hz, 2H), 2.56 (t, J=7.7 Hz, 2H), 1.87 (quintet, J=6.7 Hz, 2H), 1.61 (quintet J=7.7 Hz, 2H), 1.46 (quintet J=6.7 Hz, 2H).

7-(4-Benzyloxy-phenyl)-heptanesulfonic acid sodium salt (11.1).

A stirred mixture of 10.1 (0.9 g, 2.50 mmol) and anhydrous $Na_2SO_3$ (0.423 g, 3.36 mmol) in EtOH (20 mL)/$H_2O$ (10 ml) was heated under reflux (6 h) or microwaved using a CEM-discover system (ram time: 2 min, hold time: 5 min, temperature: 150° C., pressure: 250 psi, power: 250 W). The reaction mixture was cooled to room temperature and the solvent evaporated under reduced pressure. The residue obtained was scrupulously dried under high vacuum and the crude product (10.1, pale yellow solid) was used in the next step without further purification.

7-(3-Benzyloxy-phenyl)-heptanesulfonic acid sodium salt (11.2). Following the procedure described for 11.1 using 10.2 (0.4 g, 1.1 mmol), $Na_2SO_3$ (0.19 g, 1.5 mmol) and EtOH (8 mL)/$H_2O$ (4 ml) mixture, the crude 11.2 was obtained and used in the next step without further purification.

7-(2-Benzyloxy-phenyl)-heptanesulfonic acid sodium salt (11.3). Following the procedure described for 11.1 using 10.3 (0.231 g, 0.64 mmol), $Na_2SO_3$ (0.11 g, 0.89 mmol) and EtOH (8 mL)/$H_2O$ (4 ml) mixture, the crude 11.3 was obtained and used in the next step without further purification.

5-(4-Benzyloxy-phenyl)-pentanesulfonic acid sodium salt (11.4). Following the procedure described for 11.1 using 10.4 (0.95 g, 2.85 mmol), $Na_2SO_3$ (0.50 g, 4.0 mmol) and EtOH (25 mL)/$H_2O$ (7 ml) mixture, the crude 11.4 was obtained and used in the next step without further purification.

7-(4-Benzyloxy-phenyl)-heptanesulfonyl chloride (12.1).

To a stirred suspension of 11.1 (0.96 g, 2.50 mmol) in anhydrous benzene (20 mL)/DMF (2 ml), was added thionyl chloride (0.89 g, 7.5 mmol) and the resulting mixture was heated at 50° C. for 3 h under argon. The reaction mixture was quenched by dropwise addition of water (10 mL) at room temperature and extracted with diethyl ether. The organic layer was washed with brine, dried ($MgSO_4$) and the solvent was evaporated under reduced pressure. Purification by flash column chromatography on silica gel (20% diethyl ether-hexane) afforded 12.1 in 40% yield from 10.1 (0.38 g). White solid. m p 33-35° C.

$^1$H NMR (500 MHz, $CDCl_3$) δ 7.44 (d, J=7.5 Hz, 2H), 7.38 (t, J 7.5. Hz, 2H), 7.32 (t, J=7.5 Hz 1H), 7.08 (d, J=8.5 Hz, 2H), 6.90 (d, J=8.5 Hz, 2H), 5.04 (s, 2H), 3.64 (m as t, half of an AA'XX' system, 2H), 2.55 (t, J=7.5 Hz, 2H), 2.03 (quintet, J=7.7 Hz, 2H), 1.62-1.54 (m, 2H), 1.52-1.46 (m, 2H), 1.40-1.30 (m, 4H).

7-(3-Benzyloxy-phenyl)-heptanesulfonyl chloride (12.2) was synthesized as described in 12.1 using 11.2 (0.42 g, 1.1 mmol) and thionyl chloride (0.36 g, 3 mmol) in benzene (9 mL)/DMF (1 mL). Purification by flash column chromatography on silica gel gave the title compound (0.163 g, 39% yield from 10.2) as a viscous liquid.

$^1$H NMR (500 MHz, $CDCl_3$) δ 7.44 (d, J=7.5 Hz, 2H), 7.39 (t, J=7.5 Hz, 2H), 7.32 (t, J=7.5 Hz, 1H), 7.19 (t, J=7.2 Hz, 1H), 6.82-6.77 (m, 3H), 5.05 (s, 2H), 3.64 (m as t, half of an AA'XX' system, 2H), 2.58 (t, J=7.5 Hz, 2H), 2.02 (quintet, J=7.5 Hz, 2H), 1.62 (quintet, J=7.5 Hz, 2H), 1.48 (quintet, J=7.5 Hz, 2H), 1.42-1.32 (m, 4H).

7-(2-Benzyloxy-phenyl)-heptanesulfonyl chloride (12.3) was synthesized as described in 12.1 using 11.3 (0.46 g, 0.64 mmol) and thionyl chloride (0.228 g, 1.92 mmol) in benzene (9 mL)/DMF (1 mL). Purification by flash column chromatography on silica gel gave the title compound (0.092 g, 38% yield from 10.3) as a viscous liquid.

$^1$H NMR (500 MHz, $CDCl_3$) δ 7.44 (d, J=7.5 Hz, 2H), 7.39 (t, J=7.5 Hz, 2H), 7.33 (t, J=7.5 Hz 1H), 7.18-7.33 (m, 2H), 6.92-6.88 (m, 2H), 5.08 (s, 2H), 3.58 (m as t, half of an AA'XX' system, 2H), 2.67 (t, J=7.7 Hz, 2H), 1.99 (quintet, J=7.5 Hz, 2H), 1.62 (quintet, J=7.5 Hz, 2H), 1.46-1.4 (m, 2H), 1.36-1.32 (m, 4H).

5-(4-Benzyloxy-phenyl)-pentanesulfonyl chloride (12.4) was synthesized as described in 12.1 using 11.4 (0.96 g, 2.85 mmol) and thionyl chloride (1.00 g, 8.55 mmol) in benzene (27 mL)/DMF (3 mL). Purification by flash column chromatography on silica gel gave the title compound (0.36 g, 37% yield from 10.4) as a white solid (m p 58-60° C.).

$^1$H NMR (500 MHz, $CDCl_3$) δ 7.43 (d, J=7.5 Hz, 2H), 7.38 (t, J=7.5 Hz, 2H), 7.32 (t, J=7.5 Hz 1H), 7.07 (d, J=8.7 Hz, 2H), 6.90 (d, J=8.7 Hz, 2H), 5.04 (s, 2H), 3.64 (m as t, half of an AA'XX' system, 2H), 2.56 (t, J=7.2 Hz, 2H), 2.06 (quintet, J=7.7 Hz, 2H), 1.66 (quintet, J=7.5 Hz, 2H), 1.46 (quintet, J=7.7 Hz, 2H).

7-(4-Benzyloxy-phenyl)-heptanesulfonyl fluoride (13.1).

To a stirred solution of 12.1 (0.345 g, 0.9 mmol) in dry acetone (20 mL), was added anhydrous $NH_4F$ (0.066 g, 1.8 mmol) and the mixture refluxed for 2 hours. The reaction mixture was cooled to room temperature, the solvent was evaporated, and the residue obtained was dissolved in diethyl ether (20 mL). The ethereal solution was successively washed with water and brine, dried ($MgSO_4$) and concentrated under reduced pressure. Purification by flash column chromatography on silica gel (20% diethyl ether-hexane) afforded 13.1 (0.306 g, 93% yield) as a white solid (m p 35-38° C.).

$^1$H NMR (500 MHz, $CDCl_3$) δ 7.43 (d, J=7.5 Hz, 2H), 7.38 (t, J=7.5 Hz, 2H), 7.32 (t, J=7.5 Hz 1H), 7.08 (d, J=8.7 Hz, 2H), 6.90 (d, J=8.7 Hz, 2H), 5.04 (s, 2H), 3.36-3.32 (m, 2H), 2.54 (t, J=7.5 Hz, 2H), 1.94 (quintet, J=7.5 Hz, 2H), 1.62-1.54 (m, 2H), 1.52-1.44 (m, 2H), 1.40-1.30 (m, 4H).

7-(3-Benzyloxy-phenyl)-heptanesulfonyl fluoride (13.2) was prepared as in 13.1 using 12.2 (0.149 g, 0.39 mmol) and $NH_4F$ (0.029 g, 0.78 mmol) in dry acetone (10 mL). Purification by flash column chromatography on silica gel gave the title compound (0.128 g, 91% yield) as a viscous liquid.

$^1$H NMR (500 MHz, $CDCl_3$) δ 7.43 (d, J=7.5 Hz, 2H), 7.39 (t, J=7.5 Hz, 2H), 7.32 (t, J=7.5 Hz, 1H), 7.19 (t, J=7.2 Hz, 1H), 6.82-6.77 (m, 3H), 5.05 (s, 2H), 3.36-3.32 (m, 2H), 2.58 (t, J=7.5 Hz, 2H), 1.93 (quintet, J=7.7 Hz, 2H), 1.61 (quintet, J=7.5 Hz, 2H), 1.48 (quintet, J=7.2 Hz, 2H), 1.42-1.32 (m, 4H).

7-(2-Benzyloxy-phenyl)-heptanesulfonyl fluoride (13.3) was prepared as in 13.1 using 12.3 (0.09 g, 0.236 mmol) and $NH_4F$ (0.018 g, 0.486 mmol) in dry acetone (10 mL). Purification by flash column chromatography gave the title compound (0.079 g, 92% yield) as a viscous liquid.

$^1$H NMR (500 MHz, $CDCl_3$) δ 7.43 (d, J=7.2 Hz, 2H), 7.39 (t, J=7.2 Hz, 2H), 7.33 (t, J=7.2 Hz 1H), 7.17-7.14 (m, 2H), 6.92-6.89 (m, 2H), 5.08 (s, 2H), 3.35-3.32 (m, 2H), 2.67 (t, J=7.5 Hz, 2H), 1.89 (quintet, J=7.7 Hz, 2H), 1.62 (quintet, J=7.5 Hz, 2H), 1.46-1.4 (m, 2H), 1.36-1.32 (m, 4H).

5-(4-Benzyloxy-phenyl)-pentanesulfonyl fluoride (13.4) was synthesized as described in 13.1 using, 12.4 (0.3 g, 0.87 mmol) and $NH_4F$ (0.06 g, 1.64 mmol) in dry acetone (40 mL). Purification by flash column chromatography on silica gel gave the title compound (0.266 g, 91% yield) as a white solid (m p 66-68° C.).

$^1$H NMR (500 MHz, $CDCl_3$) δ 7.43 (d, J=7.5 Hz, 2H), 7.38 (t, J=7.5 Hz, 2H), 7.32 (t, J=7.5 Hz 1H), 7.08 (d, J=8.0 Hz, 2H), 6.90 (d, J=8.0 Hz, 2H), 5.04 (s, 2H), 3.35-3.32 (m, 2H), 2.58 (t, J=7.5 Hz, 2H), 1.96 (quintet, J=7.7 Hz, 2H), 1.65 (quintet J=7.5 Hz, 2H), 1.50 (quintet, J=7.5 Hz, 2H).

7-(4-Hydroxy-phenyl)-heptanesulfonyl fluoride (14.1).

To a solution of 13.1 (0.182 g, 0.5 mmol) in ethanedithiol (10 mL), at room temperature, under an argon atmosphere was added $BF_3.Et_2O$ (0.282 g, 2.0 mmol). The reaction mixture was stirred at room temperature for 1 hour and then diluted with diethyl ether (20 mL) and water (10 mL). The organic layer was separated and the aqueous phase extracted with diethyl ether. The combined organic layer was washed with brine, dried over $MgSO_4$ and concentrated under reduced pressure. The residue obtained was chromatographed through a column of silica gel eluting with 50% diethyl ether-hexane to give 14.1 (0.096 g, 70% yield) as a white solid (m p 47-51° C.).

$^1$H NMR (500 MHz, $CDCl_3$) δ 7.08 (d, J=9.0 Hz, 2H), 6.90 (d, J=9.0 Hz, 2H), 4.08 (br s, 2H), 3.36-3.32 (m, 2H), 2.55 (t, J=8.0 Hz, 2H), 1.98-1.90 (m, 2H), 1.62-1.54 (m, 2H), 1.52-1.44 (m, 2H) 1.38-1.34 (m, 4H).

7-(3-Hydroxy-phenyl)-heptanesulfonyl fluoride (14.2) was synthesized as described in 14.1 using 13.2 (0.1 g, 0.26 mmol) in ethanedithiol (5 mL) and $BF_3.Et_2O$ (0.14 g, 1.0 mmol). Purification by flash column chromatography on silica gel gave 14.2 (0.049 g, 69% yield) as a viscous liquid.

$^1$H NMR (500 MHz, $CDCl_3$) δ 7.14 (t, J=7.5 Hz, 1H), 6.74 (d, J=7.5 Hz, 1H), 6.66-6.64 (m, 2H), 4.70 (br s 1H), 3.36-3.32 (m, 2H), 2.56 (t, J=7.7 Hz, 2H), 1.94 (quintet, J=7.7 Hz, 2H), 1.61 (quintet, J=7.5 Hz, 2H), 1.49 (quintet, J=7.2 Hz, 2H), 1.42-1.32 (m, 4H).

7-(2-Hydroxy-phenyl)-heptanesulfonyl fluoride (14.3) was synthesized as described in 14.1 using 13.3 (0.065 g, 0.17 mmol) in ethanedithiol (5 mL) and $BF_3.Et_2O$ (0.092 g, 0.65 mmol). Purification by flash column chromatography gave 14.3 (0.033 g, 70% yield) as a viscous liquid.

$^1$H NMR (500 MHz, $CDCl_3$) δ 7.11-7.06 (m, 2H), 6.87 (dt, J=7.7 Hz, J=1.0 Hz, 1H), 6.75 (dd, J=7.7 Hz, J=1.0 Hz, 1H), 4.70 (br s, 1H), 3.35-3.32 (m, 2H), 2.61 (t, J=7.2 Hz, 2H), 1.94 (quintet, J=7.7 Hz, 2H), 1.66-1.58 (m, 2H), 1.52-1.46 (m, 2H), 1.42-1.34 (m, 4H).

5-(4-Hydroxy-phenyl)-pentanesulfonyl fluoride (14.4) was synthesized as described in 14.1 using, 13.4 (0.28 g, 0.83 mmol) in ethanedithiol (10 mL) and $BF_3.Et_2O$ (0.47 g, 3.32 mmol). Purification by flash column chromatography on silica gel gave 14.4 (0.139 g, 68% yield) as a white solid (m p 32-35° C.).

$^1$H NMR (500 MHz, $CDCl_3$) δ 7.02 (d, J=8.2 Hz, 2H), 6.76 (d, J=8.2 Hz, 2H), 4.65 (br s, 1H), 3.36-3.32 (m, 2H), 2.58 (t, J=7.2 Hz, 2H), 1.96 (quintet, J=7.7 Hz, 2H), 1.64 (quintet, J=7.5 Hz, 2H), 1.50 (quintet, J=7.5 Hz, 2H).

Sulfonyl fluoride 17 (shown in Scheme 3) was synthesized by a method depicted in Scheme 3 starting from commercially available 4-phenoxybutyl bromide (5.2).

Scheme 3

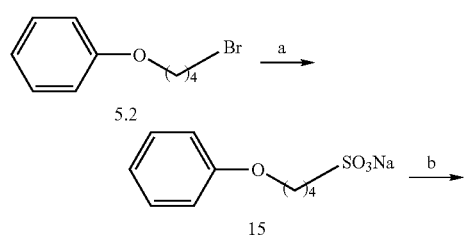

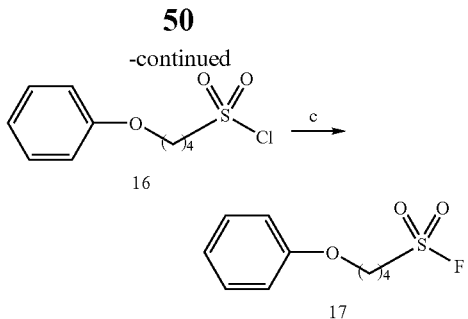

Reagents and conditions: (a) $Na_2SO_3$, $EtOH/H_2O$, reflux, 6 h or m.w, see text; (b) $SOCl_2$, PhH/DMF, $N_2$, 50° C., 3 h, 40%; (c) $NH_4F$, acetone, $N_2$, reflux, 2 h, 91%.

Experimental Procedure:

4-Phenoxybutyl sulfonic acid sodium salt (15). Following the procedure described for 11.1 using 5.2 (1.0 g, 4.37 mmol), $Na_2SO_3$ (0.77 g, 6.11 mmol), and EtOH (30 mL)/$H_2O$ (10 mL) mixture, the crude 15 was obtained and used in the next step without further purification.

4-Phenoxybutyl sulfonyl chloride (16) was synthesized as described in 12.1 using 15 (1.0 g, 4.37 mmol) and thionyl chloride (1.55 g, 13.0 mmol) in benzene (40 mL)/DMF (4 mL). Purification by flash column chromatography on silica gel afforded 15 (0.434 g, 40% yield) as a white solid (m p 65-67° C.).

$^1$H NMR (500 MHz, $CDCl_3$) δ 7.29 (t, J=8.2 Hz, 2H), 6.97 (t, J=8.2 Hz, 1H), 6.89 (d, J=8.2 Hz, 2H), 4.04 (t, J=5.7 Hz, 2H), 3.80 (m as t, half of an AA'XX' system, 2H), 2.29 (quintet, J=7.7 Hz, 2H), 2.01 (quintet, J=7.7 Hz, 2H).

4-Phenoxybutylsulfonyl fluoride (17) was synthesized as in 13.1 using 16 (0.4 g, 1.6 mmol) and $NH_4F$ (0.118 g, 3.2 mmol) in dry acetone (20 mL). Purification by flash column chromatography on silica gel gave 17 (0.338 g, 91% yield) as a white solid (m p 74-76° C.) $^1$H NMR (500 MHz, $CDCl_3$) δ 7.29 (t, J=7.5 Hz, 2H), 6.97 (t, J=7.5 Hz, 1H), 6.89 (d, J=7.5 Hz, 2H), 4.03 (t, J=5.5 Hz, 2H), 3.52-3.48 (m, 2H), 2.20 (quintet, J=7.7 Hz, 2H), 2.00 (quintet, J=8.0 Hz, 2H).

2. Synthesis of Sulfonyl Esters.

Sulfonyl ester 18 (shown in Scheme 4) was synthesized by a method depicted in Scheme 4 starting from 12.1.

Scheme 4

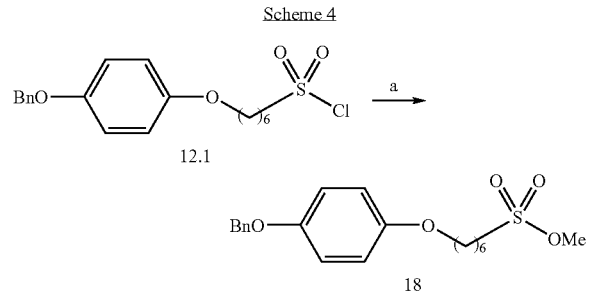

Reagents and conditions: (a) MeOH, r t, overnight 82%.

Experimental Procedure:

7-(4-Benzyloxy-phenyl)-heptane-1-sulfonic acid methyl ester (18).

A solution of 12.1 (0.050 g, 0.13 mmol) in MeOH (5 mL) was stirred at room temperature overnight.

The solvent was evaporated under reduced pressure and the residue obtained was dissolved in diethyl ether (20 mL). The ethereal solution was washed with water and brine, dried ($MgSO_4$) and evaporated under reduced pressure. Purification by flash column chromatography on silica gel (20% diethyl ether-hexane) gave the pure compound 18 (0.046 g, 82% yield), as a white solid (m p 57-59° C.).

$^1$H NMR. (500 MHz, CDCl$_3$) δ 7.43 (d, J=7.5 Hz, 2H), 7.38 (t, J=7.5 Hz, 2H), 7.32 (t, J=7.5 Hz 1H), 7.08 (d, J=8.7 Hz, 2H), 6.90 (d, J=8.7 Hz, 2H), 5.04 (s, 2H), 3.88 (s, 3H), 3.08 (m as t, half of an AA'XX' system, J=7.7 Hz, 2H), 2.54 (t, J=7.7 Hz, 2H), 1.85 (quintet, J=7.7 Hz, 2H), 1.56 (quintet, J=7.0 Hz, 2H), 1.46-1.39 (m, 2H), 1.38-1.30 (m, 4H).

3. Synthesis of Trifluoromethyl Ketones.

Trifluoromethyl ketones 23.1-12 and 24.1-10 (shown in Scheme 5) were synthesized by a method depicted in Scheme 5 starting from commercially available 2- or 3- or 4-(benzyloxy)phenol (19) and the appropriate ω-bromo-n-alkyl acid ethyl ester. 4-Phenoxy-butanoic acid (21.11) and 5-phenoxy-pentanoic acid (21.12) were also commercially available materials. Compound 24.5 was isolated in its hydrate form.

Scheme 5

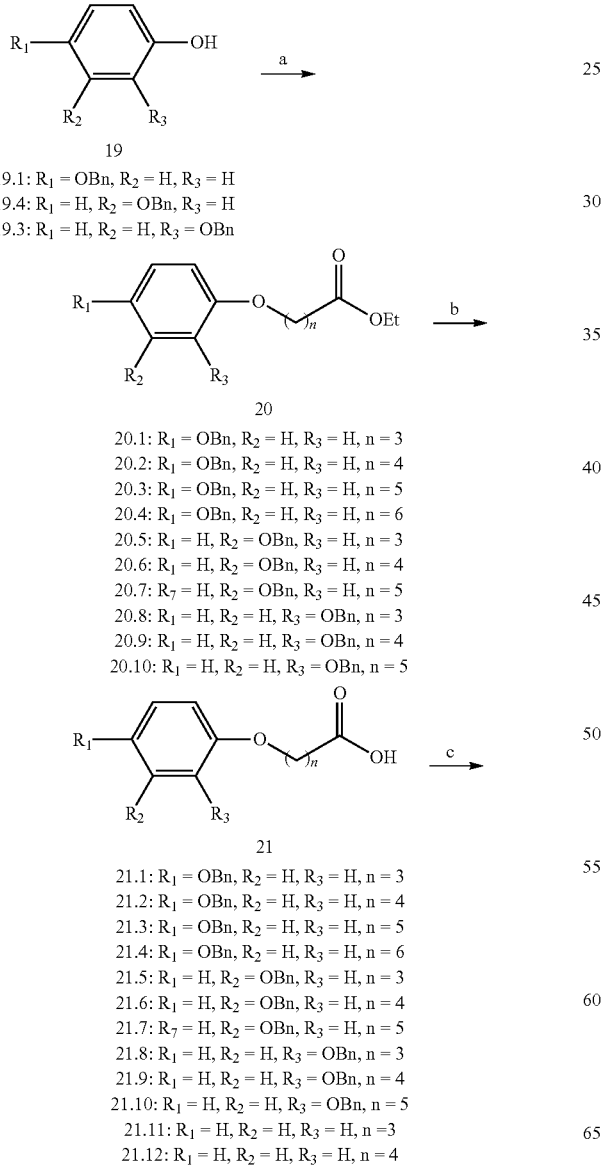

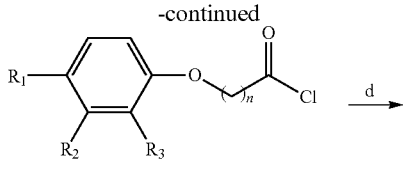

9
22.1: R$_1$ = OBn, R$_2$ = H, R$_3$ = H, n = 3
22.2: R$_1$ = OBn, R$_2$ = H, R$_3$ = H, n = 4
22.3: R$_1$ = OBn, R$_2$ = H, R$_3$ = H, n = 5
22.4: R$_1$ = OBn, R$_2$ = H, R$_3$ = H, n = 6
22.5: R$_1$ = H, R$_2$ = OBn, R$_3$ = H, n = 3
22.6: R$_1$ = H, R$_2$ = OBn, R$_3$ = H, n = 4
22.7: R$_1$ = H, R$_2$ = OBn, R$_3$ = H, n = 5
22.8: R$_1$ = H, R$_2$ = H, R$_3$ = OBn, n = 3
22.9: R$_1$ = H, R$_2$ = H, R$_3$ = OBn, n = 4
22.10: R$_1$ = H, R$_2$ = H, R$_3$ = OBn, n = 5
22.11: R$_1$ = H, R$_2$ = H, R$_3$ = H, n = 3
22.12: R$_1$ = H, R$_2$ = H, R$_3$ = H, n = 4

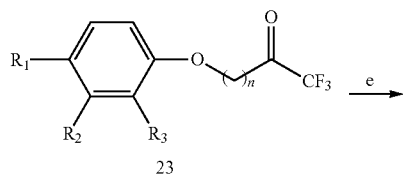

23
23.1: R$_1$ = OBn, R$_2$ = H, R$_3$ = H, n = 3
23.2: R$_1$ = OBn, R$_2$ = H, R$_3$ = H, n = 4
23.3: R$_1$ = OBn, R$_2$ = H, R$_3$ = H, n = 5
23.4: R$_1$ = OBn, R$_2$ = H, R$_3$ = H, n = 6
23.5: R$_1$ = H, R$_2$ = OBn, R$_3$ = H, n = 3
23.6: R$_1$ = H, R$_2$ = OBn, R$_3$ = H, n = 4
23.7: R$_7$ = H, R$_2$ = OBn, R$_3$ = H, n = 5
23.8: R$_1$ = H, R$_2$ = H, R$_3$ = OBn, n = 3
23.9: R$_1$ = H, R$_2$ = H, R$_3$ = OBn, n = 4
23.10: R$_1$ = H, R$_2$ = H, R$_3$ = OBn, n = 5
23.11: R$_1$ = H, R$_2$ = H, R$_3$ = H, n = 3
23.12: R$_1$ = H, R$_2$ = H, R$_3$ = H, n = 4

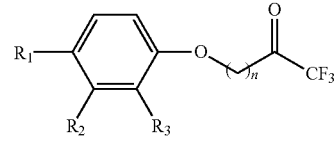

24
24.1: R$_1$ = OH, R$_2$ = H, R$_3$ = H, n = 3
24.2: R$_1$ = OH, R$_2$ = H, R$_3$ = H, n = 4
24.3: R$_1$ = OH, R$_2$ = H, R$_3$ = H, n = 5
24.4: R$_1$ = OH, R$_2$ = H, R$_3$ = H, n = 6
24.5*: R$_1$ = H, R$_2$ = OH, R$_3$ = H, n = 3
24.6: R$_1$ = H, R$_2$ = OH, R$_3$ = H, n = 4
24.7: R$_1$ = H, R$_2$ = OH, R$_3$ = H, n = 5
24.8: R$_1$ = H, R$_2$ = H, R$_3$ = OH, n = 3
24.9: R$_1$ = H, R$_2$ = H, R$_3$ = OH, n = 4
24.10: R$_1$ = H, R$_2$ = H, R$_3$ = OH, n = 5

*Compound 24.5 was isolated in its hydrate form.

Reagents and conditions: (a) K$_2$CO$_3$, 18-crown-6, Br—(CH$_2$),—COOEt, r t; (b) KOH, EtOH/H$_2$O, r t, 80-93% from 19; (c) (COCl)$_2$, CH$_2$Cl$_2$, r t; (d) (i) pyridine, CF$_3$COOCOCF$_3$, CH$_2$Cl$_2$, −78° C. to 0° C., (ii) H$_2$O, 0° C. to r t, 57-63% from 21; (e) H$_2$, Pd/C, EtOH, r t, 76-97%.

Experimental Procedures:
Esters 20.

A mixture of benzyloxyphenyl (19) (1 equiv.), ω-bromo-n-alkyl acid ethyl ester (1.2 equiv.), potassium carbonate (1.2 equiv.), and 18-crown-6 (1 equiv.) in anhydrous acetonitrile was stirred overnight at room temperature under an argon atmosphere. The reaction mixture was evaporated and the residue was partitioned between water and diethyl ether. The organic phase was separated, washed with brine, dried (MgSO$_4$), and the solvent was removed under reduced pressure to leave the crude product (20). This product contains small amounts of unreacted (ω-bromo-n-alkyl acid ethyl ester and it was used in the next step without purification. For analytical purposes 20.7 and 20.4 were further purified by flash column chromatography (20% diethyl ether-hexane) on silica gel. For a $^1$H NMR spectrum and an alternative method for the preparation of 20.4 see experimental given for the synthesis of α-keto-heterocycles.

6-[3-(Benzyloxy)phenoxy]hexanoic acid ethyl ester (20.7). Colorless oil.

$^1$H NMR (500 MHz, CDCl$_3$) δ 7.41 (d, J=7.3 Hz, 2H), 7.36 (t, J=7.3 Hz, 2H), 7.30 (t, J=7.3 Hz, 1H), 7.14 (t, J=8.2 Hz, 1H), 6.57-6.52 (m, 2H), 6.49 (dd, J=8.2 Hz, J=1.8 Hz, 1H), 5.01 (s, 2H), 4.11 (q, J=7.2 Hz, 2H), 3.91 (t, J=6.5 Hz, 2H), 2.31 (t, J=7.5 Hz, 2H), 1.80-1.73 (m, 2H), 1.72-1.64 (m, 2H), 1.51-1.43 (m, 2H), 1.24 (t, J=7.2 Hz, 3H).

Acids 21.

A mixture of the crude ester (20) and potassium hydroxide (1.3 equiv.) in EtOH/H$_2$O (10:1 mixture) was heated under reflux for 3-4 hours. The reaction mixture was cooled to room temperature and the solvent was removed under reduced pressure. The residue obtained was dissolved in water, and the pH was adjusted to 1 using concentrated HCl solution. The precipitated crude acid was isolated by filtration and dissolved in ethyl acetate. The resulting solution was washed with brine, dried (MgSO$_4$), and the solvent was evaporated to give the product 21 in 80-93% yield (from 19).

Selected Data of Synthesized Acids (21):

4-[4-(Benzyloxy)phenoxy]butanoic acid (21.1). White solid. m p 125-126° C.

$^1$H NMR (500 MHz, CDCl$_3$) δ 10.95 (br s, 1H), 7.41 (d, J=7.3 Hz, 2H), 7.37 (t, J=7.3 Hz, 2H), 7.31 (t, J=7.3 Hz, 1H), 6.90 (m as d, J=9.0 Hz, 2H), 6.81 (m as d, J=9.0 Hz, 2H), 5.01 (s, 2H), 3.97 (t, J=6.3 Hz, 2H), 2.58 (t, J=7.5 Hz, 2H), 2.09 (quintet, J=6.7 Hz, 2H); IR (neat) 2904, 2865, 1704, 1509 cm$^{-1}$.

5-[4-(Benzyloxy)phenoxy]pentanoic acid (21.2). White solid. m p 127-128° C.

$^1$H NMR (500 MHz, CDCl$_3$) δ 11.04 (br s, 1H), 7.42 (d, J=7.3 Hz, 2H), 7.37 (t, J=7.3 Hz, 2H), 7.31 (t, J=7.3 Hz, 1H), 6.89 (d, J=8.9 Hz, 2H), 6.81, (d, J=8.9 Hz, 2H), 5.01 (s, 2H), 3.92 (t, J=6.4 Hz, 2H), 2.44 (t, J=7.1 Hz, 2H), 1.85-1.79 (m, 4H); IR (neat) 2954, 2864, 1694, 1509 cm$^{-1}$.

6-[4-(Benzyloxy)phenoxy]hexanoic acid (21.3). White solid. m p 100-101° C.

$^1$H NMR (500 MHz, CDCl$_3$) δ 11.00 (br s, 1H), 7.42 (d, J=7.3 Hz, 2H), 7.37 (t, J=7.3 Hz, 2H), 7.31 (t, J=7.3 Hz, 1H), 6.89 (d, J=9.0 Hz, 2H), 6.81 (d, J=9.0 Hz, 2H), 5.01 (s, 2H), 3.90 (t, J=6.4 Hz, 2H), 2.39 (t, J=7.4 Hz, 2H), 1.78 (quintet, J=6.8 Hz, 2H), 1.71 (quintet, J=7.5 Hz, 2H), 1.60-1.45 (m, 2H); IR (neat) 2945, 2863, 1693, 1508 cm$^{-1}$.

7-[4-(Benzyloxy)phenoxy]heptanoic acid (21.4). White solid. m p 118-119° C.

$^1$H NMR (500 MHz, CDCl$_3$) δ 11.20 (br S, 1H), 7.42 (d, J=7.3 Hz, 2H), 7.37 (t, J=7.3 Hz, 2H), 7.31 (t, J=7.3 Hz, 11), 6.89 (d, J=9.0 Hz, 2H), 6.81 (d, J=9.0 Hz, 2H), 5.01 (s, 2H), 3.89 (t, J=6.4 Hz, 2H), 2.36 (t, J=7.4 Hz, 2H), 1.79-1.72 (m, 2H), 1.70-1.63 (m, 2H), 1.51-1.37 (m, 4H).

4-[3-(Benzyloxy)phenoxy]butanoic acid (21.5). White solid. m p 76-77° C.

5-[3-(Benzyloxy)phenoxy]pentanoic acid (21.6). White solid. m p 71-72° C.

$^1$H NMR (500 MHz, CDCl$_3$) δ 10.82 (br s, 1H), 7.45 (d, J=7.3 Hz, 2H), 7.38 (t, J=7.3 Hz, 2H), 7.32 (t, J=7.3 Hz, 1H), 7.17 (t, J=8.2 Hz, 1H), 6.57 (dd, J=8.2 Hz, J=2.0 Hz, 1H), 6.54 (t, J=2.0 Hz, 1H), 6.50 (dd, J=8.2 Hz, J=2.0 Hz, 1H), 5.04 (s, 2H), 3.95 (t, J=5.7 Hz, 2H), 2.44 (t, J=6.7 Hz, 2H), 1.87-1.80 (m, 4H).

6-[3-(Benzyloxy)phenoxy]hexanoic acid (21.7). White solid. m p 72-73° C.

$^1$H NMR (500 MHz, CDCl$_3$) δ 11.31 (br s, 11-1H), 7.42 (d, J=7.3 Hz, 2H), 7.38 (t, J=7.3 Hz, 2H), 7.32 (t, J=7.3 Hz, 1H), 7.16 (t, J=8.2 Hz, 1H), 6.56 (dd, J=8.2 Hz, J=1.8 Hz, 1H), 6.54 (t, J=1.8 Hz, 1H), 6.50 (dd, J=8.2 Hz, J=1.8 Hz, 1H), 5.04 (s, 2H), 3.93 (t, J=6.5 Hz, 2H), 2.39 (t, J=7.5 Hz, 2H), 1.83-1.75 (m, 2H), 1.74-1.67 (m, 2H), 1.56-1.48 (m, 2H).

4-[2-(Benzyloxy)phenoxy]butanoic acid (21.8). White solid. m p 75-76° C.

$^1$H NMR (500 MHz, CDCl$_3$) δ 9.50 (br s, 1H), 7-44 (d, J=7.4 Hz, 2H), 7.37 (t, J=7.4 Hz, 2H), 7.30 (t, J=7.4 Hz, 1H), 6.95-6.86 (m, 4H), 5.12 (s, 2H), 4.09 (t, J=5.9 Hz, 2H), 2.61 (t, J=7.1 Hz, 2H), 2.15 (quintet, J=6.5 Hz, 2H); IR (neat) 1693, 1590 cm$^{-1}$.

5-[2-(Benzyloxy)phenoxy]pentanoic acid (21.9). White solid. m p 74-75° C.

$^1$H NMR (500 MHz, CDCl$_3$) δ 11.02 (br s, 1H), 7.44 (d, J=7.4 Hz, 2H), 7.36 (t, J=7.4 Hz, 2H), 7.29 (t, J=7.4 Hz, 1H), 6.95-6.85 (m, 4H), 5.12 (s, 2H), 4.05 (t, J=5:9 Hz, 2H), 2.45 (t, J=7.1 Hz, 2H), 1.92-1.82 (m, 4H).

6-[2-(Benzyloxy)phenoxy]hexanoic acid (21.10). White solid. m p 77-78° C.

$^1$H NMR (500 MHz, CDCl$_3$) δ 10.92 (br s, 1H), 7.44 (d, J=7.3 Hz, 2H), 7.36 (t, J=7.3 Hz, 2H), 7.29 (t, J=7.3 Hz, 1H), 6.95-6.84 (m, 4H), 5.12 (s, 2H), 4.03 (t, J=6.4 Hz, 2H), 2.36 (t, J=7.2 Hz, 2H), 1.85 (quintet, J=6.7 Hz, 2H), 1.71 (quintet, J=7.3 Hz, 2H), 1.59-1.51 (m, 2H).

Carboxylic Acid Chlorides 22.

To a solution of acid 21 (1 equiv.) in anhydrous CH$_2$Cl$_2$ at room temperature, under an argon atmosphere was added oxalyl chloride (2 equiv.) over a 2-min period. The mixture was stirred for 2 h, solvent and excess oxalyl chloride were removed under reduced pressure, and the crude carboxylic acid chloride (22) was used in the next step without further purification.

Trifluoromethyl Ketones 23.

To a solution of carboxylic acid chloride 22 in anhydrous CH$_2$Cl$_2$ at −78° C. under an argon atmosphere were added successively trifluoroacetic anhydride (6 equiv.) and dry pyridine (8 equiv.). The reaction mixture was stirred at −78° C. for 2 hours, and then it was allowed to warm to 0° C. and stirred for an additional 2 hours period. Water was added dropwise, the resulting mixture was warmed to room temperature, and extracted with CH$_2$Cl$_2$. The organic layer was washed with brine, dried (MgSO$_4$) and the solvent was evaporated. Following the workup, the crude mixture was chromatographed on a silica gel column (eluting with 30% diethyl ether-hexane), and the fraction that contains the product was concentrated and dried in high vacuum (in the presence of P$_2$O$_5$) to give compound 23 in 57-63% yield (from 21).

Selected Data of Synthesized Trifluoromethyl Ketones (23):

1,1,1-Trifluoro-5-[4-(benzyloxy)phenoxy]-2-pentanone (23.1). White solid. m p 59-61° C. $^1$H NMR (500 MHz, CDCl$_3$) δ 7.41 (d, J=7.3 Hz, 2H), 7.37 (t, J=7.3 Hz, 2H), 7.30 (t, J=7.3 Hz, 1H), 6.89 (m as d, J=9.0 Hz, 2H), 6.79 (m as d, J=9.0 Hz, 2H), 5.01 (s, 2H), 3.96 (t, J=5.7 Hz, 2H), 2.93 (t, J=7.0 Hz, 2H), 2.14 (quintet, J=6.5 Hz, 2H); IR (neat) 1765, 1509 cm$^{-1}$.

1,1,1-Trifluoro-6-[4-(Benzyloxy)phenoxy]-2-hexanone (23.2). White solid. m p 95.5-96° C. $^1$H NMR (500 MHz, CDCl$_3$) δ 7.42 (d, J=7.3 Hz, 2H), 7.38 (t, J=7.3 Hz, 2H), 7.31 (t, J=7.3 Hz, 1H), 6.90 (d, J=8.9 Hz, 2H), 6.81 (d, J=8.9 Hz, 2H), 5.01 (s, 2H), 3.93 (t, J=6.4 Hz, 2H), 2.82 (t, J=7.1 Hz, 2H), 1.88 (quintet, J=7.1 Hz, 2H), 1.81 (quintet, J=6.6 Hz, 2H); IR (neat) 1759, 1509 cm$^{-1}$.

1,1,1-Trifluoro-7-[4-(Benzyloxy)phenoxy]-2-heptanone (23.3). White solid. m p 59-60° C. IR (neat) 1761, 1509 cm$^{-1}$.

1,1,1-Trifluoro-8-[4-(Benzyloxy)phenoxy]-2-octanone (23.4). White solid. m p 82-83° C. $^1$H NMR (500 MHz, CDCl$_3$) δ 7.42 (d, J=7.3 Hz, 2H), 7.38 (t, J=7.3 Hz, 2H), 7.31 (t, J=7.3 Hz, 1H), 6.89 (d, J=8.9 Hz, 2H), 6.81 (d, J=8.9 Hz, 2H), 5.01 (s, 2H), 3.90 (t, J=6.4 Hz, 2H), 2.73 (t, J=7.1 Hz, 2H), 1.80-1.67 (m, 4H), 1.52-1.45 (m, 2H), 1.44-1.36 (m, 2H).

1,1,1-Trifluoro-5-[3-(Benzyloxy)phenoxy]-2-pentanone (23.5). Colorless viscous oil.

$^1$H NMR (500 MHz, CDCl$_3$) δ 7.42 (d, J=7.3 Hz, 2H), 7.38 (t, J=7.3 Hz, 2H), 7.31 (t, J=7.3 Hz, 1H), 7.16 (t, J=8.2 Hz, 1H), 6.58 (dd, J=8.2 Hz, J=2.0 Hz, 1H), 6.52 (t, J=2.0 Hz, 1H), 6.48 (dd, J=8.2 Hz, J=2.0 Hz, 1H), 5.03 (s, 2H), 3.96 (t, J=5.9 Hz, 2H), 2.92 (t, J=6.9 Hz, 2H), 2.14 (quintet, J=6.5 Hz, 2H); IR (neat) 1763, 1591 cm$^{-1}$.

1,1,1-Trifluoro-6-[3-(Benzyloxy)phenoxy]-2-hexanone (23.6). Colorless viscous oil.

$^1$H NMR (500 MHz, CDCl$_3$) δ 7.42 (d, J=7.3 Hz, 2H), 7.38 (t, J=7.3 Hz, 2H), 7.32 (t, J=7.3 Hz, 1H), 7.17 (t, J=8.2 Hz, 1H), 6.58 (dd, J=8.2 Hz, J=2.0 Hz, 1H), 6.53 (t, J=2.0 Hz, 1H), 6.49 (dd, J=8.2 Hz, J=2.0 Hz, 1H); 5.04 (s, 2H), 3.96 (t, J=5.9 Hz, 2H), 2.81 (t, J=6.8 Hz, 2H), 1.91-1.78 (m, 4H).

1,1,1-Trifluoro-7-[3-(Benzyloxy)phenoxy]-2-heptanone (23.7). Colorless viscous oil.

1,1,1-Trifluoro-5-[2-(Benzyloxy)phenoxy]-2-pentanone (23.8). White solid. m p 50-51° C. $^1$H NMR (500 MHz, CDCl$_3$) δ 7.42 (d, J=7.4 Hz, 2H), 7.36 (t, J=7.4 Hz, 2H), 7.30 (t, J=7.4 Hz, 1H), 6.96-6.89 (m, 4H), 5.09 (s, 2H), 4.06 (t, J=5.9 Hz, 2H), 2.98 (t, J=7.0 Hz, 2H), 2.16 (quintet, J=6.5 Hz, 2H); IR (neat) 1763, 1593 cm$^{-1}$.

1,1,1-Trifluoro-6-[2-(Benzyloxy)phenoxy]-2-hexanone (23.9). Colorless viscous oil.

$^1$H NMR (500 MHz, CDCl$_3$) δ 7.42 (d, J=7.4 Hz, 2H), 7.35 (t, J=7.4 Hz, 2H), 7.29 (t, J=7.4 Hz, 1H), 6.93 (d, J=7.4 Hz, 1H), 6.91-6.86 (m and t overlapping, especially 6.90, t, J=3.9 Hz, 3H), 5.10 (s, 2H), 4.04 (t, J 35.9 Hz, 2H), 2.80 (t, J=6.9 Hz, 2H), 1.93-1.82 (m, 4H).

1,1,1-Trifluoro-7-[2-(Benzyloxy)phenoxy]-2-heptanone (23.10). White solid. m p 31-32° C. $^1$H NMR (500 MHz, CDCl$_3$) δ 7.43 (d, J=7.3 Hz, 2H), 7.36 (t, J=7.3 Hz, 2H), 7.30 (t, J=7.3 Hz, 1H), 6.95-6.85 (m, 4H), 5.11 (s, 2H), 4.03 (t, J=6.4 Hz, 2H), 2.70 (t, J=7.1 Hz, 2H), 1.86 (quintet, J=6.7 Hz, 2H), 1.75 (quintet, J=7.3 Hz, 2H), 1.59-1.50 (m, 2H).

1,1,1-Trifluoro-5-phenoxy-2-pentanone (23.11). Colorless viscous oil.

$^1$H NMR (500 MHz, CDCl$_3$) δ 7.28 (t, J=7.4 Hz, 2H), 6.95 (t, J=7.4 Hz, 1H), 6.87 (d, J=7.4 Hz, 2H), 4.00 (t, J=5.8 Hz, 2H), 2.95 (t, J=7.0 Hz, 2H), 2.17 (quintet, J=6.4 Hz, 2H); $^{13}$C NMR (126 MHz, CDCl$_3$) δ 191.6 (q, J=35 Hz, C=O), 158.9, 129.9, 121.4, 116.0 (q, J=292 Hz, CF$_3$), 114.8, 66.1, 33.5, 22.8; IR (neat) 1763, 1601, 1588, 1498 cm$^{-1}$; mass spectrum m/z (relative intensity) 232 (M$^+$, 25), 139 (24), 94 (100), 77 (16), 69 (27). Exact mass calculated for C$_{11}$H$_{11}$O$_2$F$_3$; 232.0711; found, 232.0714.

1,1,1-Trifluoro-6-phenoxy-2-hexanone (23.12). White solid. m p 50-51° C.

$^1$H NMR (500 MHz, CDCl$_3$) δ 7.28 (t, J=7.4 Hz, 2H), 6.94 (t, J=7.4 Hz, 1H), 6.88 (d, J=7.4 Hz, 2H), 3.98 (t, J=5.9 Hz, 2H), 2.83 (t, J=6.7 Hz, 2H), 1.95-1.80 (m, 4H); $^{13}$C NMR (126 MHz, CDCl$_3$) δ 191.7 (q, J=35 Hz, C=O), 159.2, 129.9, 121.2, 116.0 (q, J=291 Hz, CF$_3$), 114.8, 67.5, 36.4, 28.6, 19.8; IR (neat) 1759, 1601, 1585, 1500 cm$^{-1}$.

Trifluoromethyl Ketones 24.

To a solution of trifluoromethyl ketone 23 (1 equiv.) in EtOH was added 10% Pd/C (7% w/w), and the resulting suspension was stirred vigorously under hydrogen atmosphere, overnight at room temperature. The catalyst was removed by filtration through Celite, and the filtrate was evaporated under reduced pressure. The residue obtained was chromatographed on a silica gel column (eluting with 60% diethyl ether-hexane), and the fraction that contains the product was concentrated and dried in high vacuum (in the presence of P$_2$O$_5$) to give compound 24 in 70-97% yield. Especially in case of compound 24.5 the hydrate was isolated in 80% yield.

Selected Data of Synthesized Trifluoromethyl Ketones (24):

1,1,1-Trifluoro-5-[4-(hydroxy)phenoxy]-2-pentanone (24.1). Colorless viscous oil. $^1$H NMR (500 MHz, CDCl$_3$) δ 6.76 (m as br s, 4H), 4.51 (br s, 1H), 3.95 (t, J=5.8 Hz, 2H), 2.95 (t, J=7.0 Hz, 2H), 2.15 (quintet, J=6.5 Hz, 2H); $^{13}$C NMR (126 MHz, CDCl$_3$) δ 191.5 (q, J=35 Hz, C=O), 152.7, 149.8, 116.2, 115.7, 115.6 (q, J=292 Hz, CF$_3$), 66.7, 33.2, 22.5; IR (neat) 3379 br, 1763, 1509 cm$^{-1}$.

1,1,1-Trifluoro-6-[4-(hydroxy)phenoxy]-2-hexanone (24.2). White solid. m p 63-64° C. $^1$H NMR (500 MHz, CDCl$_3$) δ 6.76 (m as br s, 4H), 4.57 (br s, 1H), 3.92 (ti J=6.4 Hz, 2H), 2.82 (t, J=7.1 Hz, 2H), 1.88 (quintet, J=7.1 Hz, 2H), 1.81 (quintet, J=6.6 Hz, 2H); IR (neat) 3398 br, 1754, 1509 cm$^{-1}$.

1,1,1-Trifluoro-7-[4-(hydroxy)phenoxy]-2-heptanone (24.3). Colorless viscous oil.

IR (neat) 3386 br, 1762, 1509 cm$^{-1}$.

1,1,1-Trifluoro-8-[4-(hydroxy)phenoxy]-2-octanone (24.4). White solid. m p 61-62° C. $^1$H NMR (500 MHz, CDCl$_3$) δ 6.77 (m as d, J=9.1 Hz, 2H), 6.75 (m as d, J=9.1 Hz, 2H), 4.40 (br s, 1H), 3.89 (t, J=6.4 Hz, 2H), 2.73 (t, J=7.1 Hz, 2H), 1.80-1.67 (m, 4H), 1.52-1.45 (m, 2H), 1.44-1.36 (m, 2H).

1,1,1-Trifluoro-2,2-dihydroxy-5-[3-(hydroxy)phenoxy]pentane (24.5). White solid. m p 76-77° C.

$^1$H NMR (500 MHz, CDCl$_3$/DMSO-d$_6$) δ 8.53 (br s, exchange with D$_2$O, 1H), 7.06 (t, J=8.2 Hz, 1H), 6.47-6.42 (m, 2H), 6.39 (dd, J=8.2 Hz, J=1.9 Hz, 1H), 5.49 (br s, exchange with D$_2$O, 2H), 3.99 (t, J=6.1 Hz, 2H), 2.05 (m, 2H), 1.95 (t, J=7.1 Hz, 2H); IR (neat) 3300 br, 1605 cm$^{-1}$.

1,1,1-Trifluoro-6-[3-(hydroxy)phenoxy]-2-hexanone (24.6). Colorless viscous oil.

$^1$H NMR (500 MHz, CDCl$_3$) δ 7.11 (t, J=8.2 Hz, 1H), 6.46 (dd, J=8.2 Hz, J=2.2 Hz, 1H), 6.42 (dd, J=8.2 Hz, J=2.2 Hz, 1H), 6.39 (t, J=2.2 Hz, 1H), 5.19 (br s, 1H), 3.94 (t, J=5.9 Hz, 2H), 2.81 (t, J=6.8 Hz, 2H), 1.90-1.77 (m, 4H).

1,1,1-Trifluoro-7-[3-(hydroxy)phenoxy]-2-heptanone (24.7). Orange viscous oil.

1,1,1-Trifluoro-5-[2-(hydroxy)phenoxy]-2-pentanone (24.8). Colorless viscous oil.

$^1$H NMR (500 MHz, CDCl$_3$) δ 6.95 (d, J=7.7 Hz, 1H), 6.89 (m as quintet, J=3.9 Hz, 1H), 6.83 (d, J=4.2 Hz, 2H), 5.52 (br s, 1H), 4.11 (t, J=6.0 Hz, 2H), 2.96 (t, J=6.9 Hz, 2H), 2.23 (quintet, J=6.5 Hz, 2H).

1,1,1-Trifluoro-6-[2-(hydroxy)phenoxy]-2-hexanone (24.9). White solid. m p 51-52° C. $^1$H NMR (500 MHz, CDCl$_3$) δ 6.94 (d, J=7.7 Hz, 1H), 6.90-6.86 (m, 1H), 6.85-6.82 (m, 2H), 5.60 (br s, 1H), 4.07 (t, J=5.7 Hz, 2H), 2.83 (t, J=6.3 Hz, 2H), 1.94-1.84 (m, 4H).

1,1,1-Trifluoro-7-[2-(hydroxy)phenoxy]-2-heptanone (24.10). White semi-solid.

$^1$H NMR (500 MHz, CDCl$_3$) δ 6.84 (d, J=7.3 Hz, 1H), 6.80-6.72 (m, 3H), 5.58 (br s, 1H), 3.95 (t, J=6.4 Hz, 2H), 2.66 (t, J=7.1 Hz, 2H) 1.75 (quintet, J=6.7 Hz, 2H), 1.66 (quintet, J=7.3 Hz, 2H), 1.46-1.38 (m, 2H).

Trifluoromethyl ketones 27.1-4 (shown in Scheme 6) were synthesized by a method depicted in Scheme 6. 4-Phenyl-butyric acid (25.1), 5-phenyl-pentanoic acid (25.2), 6-phenyl-hexanoic acid (25.3) and 5-(4-methoxy-phenyl)-pentanoic acid (25.4) were commercially available starting materials.

Scheme 6

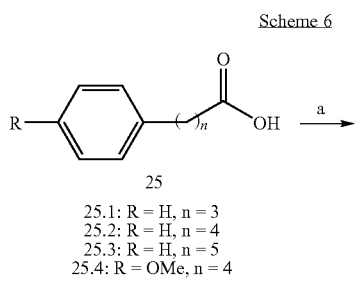

25
25.1: R = H, n = 3
25.2: R = H, n = 4
25.3: R = H, n = 5
25.4: R = OMe, n = 4

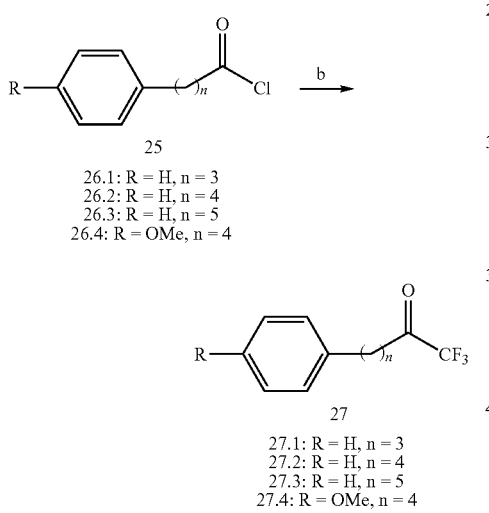

26.1: R = H, n = 3
26.2: R = H, n = 4
26.3: R = H, n = 5
26.4: R = OMe, n = 4

27
27.1: R = H, n = 3
27.2: R = H, n = 4
27.3: R = H, n = 5
27.4: R = OMe, n = 4

Reagents and conditions: (a) (COCl)$_2$, CH$_2$Cl$_2$, r t; (b) (i) pyridine, CF$_3$COOCOCF$_3$, CH$_2$Cl$_2$, −78° C. to 0° C., (ii) H$_2$O, 0° C. to r t, 61-63% from 25.

Experimental Procedures:

The synthesis of compounds 27 was carried out analogous to the preparation of compounds 23.

Selected Data of Synthesized Analogs 27.

1,1,1-Trifluoro-5-phenyl-2-pentanone (27.1). Colorless viscous oil.

IR (neat) 1762, 1604, 1498, 1454, 1403 cm$^{-1}$.

1,1,1-Trifluoro-6-phenyl-2-hexanone (27.2). Colorless viscous oil.

$^1$H NMR (500 MHz, CDCl$_3$) δ 7.27 (t, J=7.5 Hz, 2H), 7.17 (t, J=7.5 Hz, 1H), 7.15 (d, J=7.5 Hz, 2H), 2.70 (t, J=7.2 Hz, 2H), 2.63 (t, J=7.7 Hz, 2H), 1.76-1.62 (m, 4H); $^{13}$C NMR (126 MHz, CDCl$_3$) δ 191.7 (q, J=35 Hz, C=O), 142.0, 128.8, 128.7, 126.3, 116.0 (q, J=292 Hz, CF$_3$), 36.6, 35.8, 30.8, 22.4; IR (neat) 1763, 1604, 1497, 1454, 1404 cm$^{-1}$.

1,1,1-Trifluoro-7-phenyl-2-heptanone (27.3)

$^1$H NMR (500 MHz, CDCl$_3$) δ 7.27 (t, J=7.5 . Colorless viscous oil. Hz, 2H), 7.18 (t, J=7.5 Hz, 1H), 7.16 (d, J=7.5 Hz, 2H), 2.69 (t, J=7.2 Hz, 2H), 2.61 (t, J=7.7 Hz, 2H), 1.70 (quintet, J=7.6 Hz, 2H), 1.64 (quintet, J=7.6 Hz, 2H), 1.37 (quintet, J=7.7 Hz, 2H); IR (neat) 1763, 1604, 1497, 1454, 1402 cm$^{-1}$; mass spectrum m/z (relative intensity) 244 (M$^-$, 21), 175 (8), 117 (20), 91 (100), 77 (6). Exact mass calculated for C$_{13}$H$_{15}$OF$_3$; 244.1075; found, 244.1073.

1,1,1-Trifluoro-6-(4-methoxy-phenyl)-2-hexanone (27.4). Colorless viscous oil.

$^1$H NMR (500 MHz, CDCl$_3$) δ 7.07 (d, J=8.4 Hz, 2H), 6.82 (d, J=8.4 Hz, 2H), 3.77 (s, 3H), 2.71 (t, J=6.9 Hz, 2H), 2.58 (t, J=7.4 Hz, 2H), 1.70 (quintet, J=7.1 Hz, 2H), 1.62 (quintet, J=6.8 Hz, 2H); IR (neat) 1763, 1612, 1584, 1512 cm$^{-1}$.

Trifluoromethyl ketones 30 and 35 (shown in Scheme 7) were synthesized by a method depicted in Scheme 7. 3-(Methoxycarbonyl)phenylboronic acid, 3-benzyloxyphenylboronic acid and 3-benzyloxybromobenzene (28) were commercially available starting materials while (3-bromophenyl)acetic acid methyl ester (31) was synthesized from commercially available 3-bromophenylacetic acid following a method disclosed in Luning, U et al., Eur. J. Org. Chem., 2002, 3294-3303, the contents of which are incorporated by reference.

Scheme 7

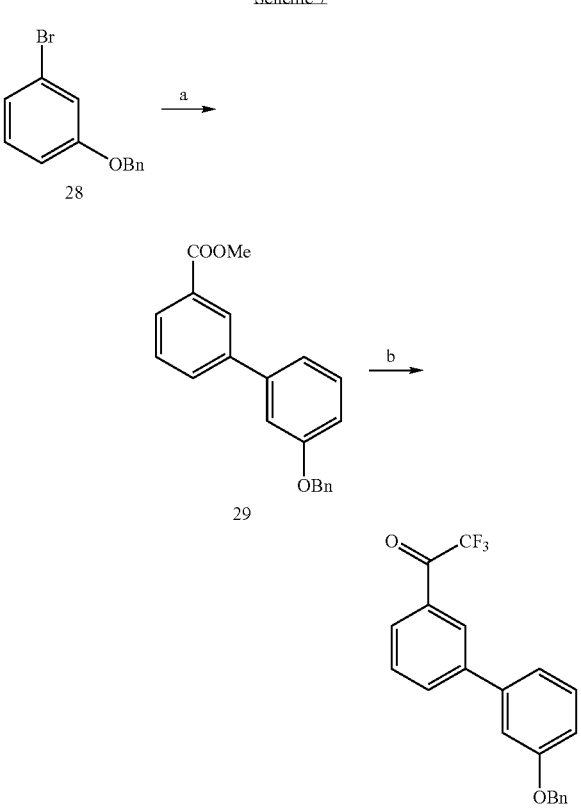

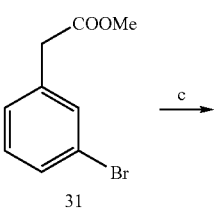

31

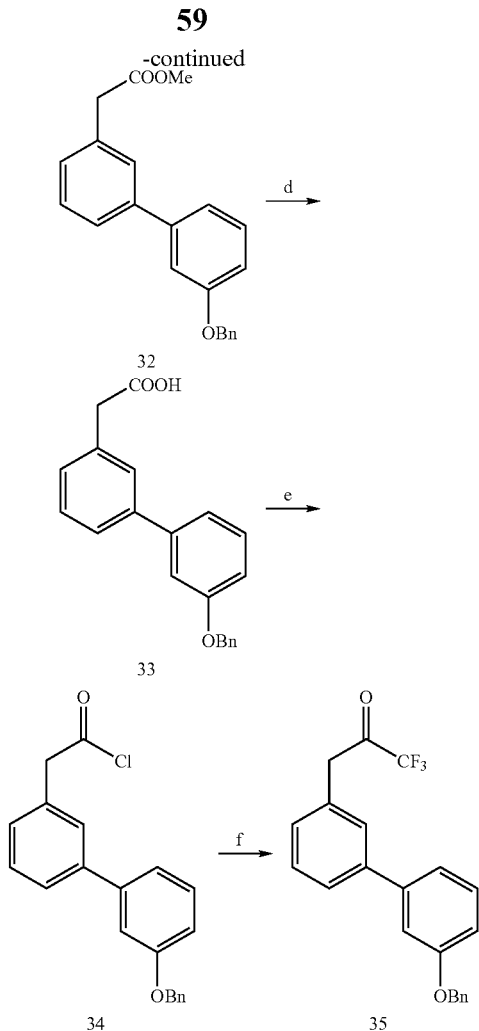

Reagents and conditions: (a) 3-(methoxycarbonyl)phenyl-boronic acid, Ba(OH)$_2$, Pd(PPh$_3$)$_4$, DME/H$_2$O, m.w, see text, 50%; (b) TMS—CF$_3$, TBAF, PhCH$_3$, N$_2$, −78° C. to r t, 18 h, 65%; (c) 3-benzyloxyphenylboronic acid, Ba(OH)$_2$, Pd(PPh$_3$)$_4$, DME/H$_2$O, m.w, see text, 48%; (d) KOH, EtOH/H$_2$O, 50° C., 2 h; (e) (COCl)$_2$, CH$_2$Cl$_2$, r t, 2 h; (f) (i) CF$_3$COOCOCF$_3$, pyridine, CH$_2$Cl$_2$, 0° C. to r t, (ii) H$_2$O, 0° C. to r t, 37% from 32.

Experimental Procedures:

3'-Benzyloxy-biphenyl-3-carboxylic acid methyl ester (29):

A degassed mixture of 3-benzyloxy-phenyl bromide (28) (0.176 g, 0.67 mmol), 3-methoxycarbonylphenylboronic acid (0.18 g, 1 mmol), barium hydroxide (0.25 g, 1.47 mmol), Pd(PPh$_3$)$_4$ (0.077 g, 0.067 mmol), DME (5 mL) and H$_2$O (3 mL) was microwaved with vigorous stirring using a CEM-discover system (ram time: 2 min, hold time: 5 min, temperature: 120° C., pressure: 200 psi, power: 250 W). The crude reaction mixture filtered through a plug of celite and concentrated in vacuo. The residue obtained was purified by flash column chromatography (25% diethyl ether-hexane) to give the title compound (29) (0.118 g, 60% yield) as a viscous liquid.

$^1$H NMR (500 MHz, CDCl$_3$) δ 8.27 (t, J=1.5 Hz, 1H), 8.20 (dd, J=8.0 Hz, J=1.5 Hz, 1H), 7.76 (dd, J=8.0 Hz, J=2.0 Hz, 1H), 7.50 (t, J=8.0 Hz, 1H), 7.47 (d, J=7.5 Hz, 2H), 7.42-7.32 (m, 4H), 7.25-7.22 (m, 2H), 7.00 (dd, J=8.2 Hz, J=2.0 Hz, 1H), 5.13 (s, 2H), 3.95 (s, 3H).

1,1,1-Trifluoro-2-(3-benzyloxy-biphenyl-3-yl)-2-ethanone (30).

A solution of 29 (0.1 g, 0.314 mmol) in anhydrous toluene (5 mL) was cooled to −78° C., under nitrogen, and trifluoromethyltrimethylsilane (62.5 mg, 0.44 mmol) was added. The mixture was stirred for 15 min at −78° C., then a 1M anhydrous solution of tetrabutylammonium fluoride in THF (0.026 ml, 0.026 mmol) was added and the resultant mixture was gradually warmed to room temperature. After stirring for 12 h at room temperature, the reaction mixture was diluted with 4N HCl solution (2 mL) and stirred for an additional 2 h period. The organic layer was separated and the aqueous layer was extracted with diethyl ether (20 mL). The combined organic layer was washed with aqueous saturated NaHCO$_3$ solution (5 mL) and brine, dried (MgSO$_4$) and concentrated under reduced pressure. The residue was purified by flash column chromatography on silica gel (25% diethyl ether-hexane) and the fraction that contains the product 30 and its hydrate form (2:1 ratio by $^1$H NMR) was concentrated and dried in high vacuum (in the presence of P$_2$O$_5$) to give pure compound 30 (0.0876 g, 76% yield) as a viscous liquid.

$^1$H NMR (500 MHz, CDCl$_3$) δ 8.26 (s, 1H), 8.04 (d, J=7.5 Hz, 1H), 7.90 (d, J=8.0 Hz, 1H), 7.61 (t, J=7.5 Hz, 1H), 7.47 (d, J=8.0 Hz, 2H), 7.44-7.38 (m, 3H), 7.3 (t, J=7.2 Hz, 1H), 7.22-7.20 (m, 2H), 7.03 (dd, J=8.0 Hz, J=2.5 Hz, 1H), 5.08 (s, 2H).

2-(3-Benzyloxy-biphenyl-3-yl)-acetic acid methyl ester (32) was synthesized following the procedure described for the preparation of 29 using 3-bromo-phenyl acetic acid methyl ester (31) (0.31 g, 1.35 mmol), 3-benzyloxy-phenyl boronic acid (0.45 g, 2 mmol), barium hydroxide (0.5 g, 3 mmol) and Pd(PPh$_3$)$_4$ (0.15 g, 0.13 mmol), in DME (10 mL)/water (4 mL). Purification by flash column chromatography on silica gel gave pure compound 32 (0.22 g, 49% yield) as a white solid (m p 50-52° C.).

$^1$H NMR (500 MHz, CDCl$_3$) δ 7.49-7.45 (m, 4H), 7.42-7.32 (m, 5H), 7.27 (d, J=7.0 Hz, 1H), 7.21 (t, J=2.5 Hz, 1H) 7.19 ((dd, J=7.5 Hz, J=1.0 Hz, 1H), 6.97 (dd, J=8.0 Hz, J=2.5 Hz 1H), 5.1 (s, 2H), 3.71 (s, 3H), 3.69 (s, 2H).

2-(3-Benzyloxy-biphenyl-3-yl)-acetic acid (33).

A mixture of 26 (0.1 g, 0.3 mmol) and potassium hydroxide (0.08 g, 1.2 mmol) in wet EtOH (5 mL) was heated at 50° C., under nitrogen for 2 hours. The reaction mixture was cooled to room temperature and the solvent evaporated under reduced pressure. The residue obtained was dissolved in water (5 mL) and the pH was adjusted to 1 using 5% aqueous HCl solution (2 mL). The precipitated crude acid was isolated by filtration and dissolved in ethyl acetate. The resulting solution was washed with brine, dried (MgSO$_4$) and concentrated under reduced pressure to give 33 as a white solid (0.087 g, 91%), which was used in the next step without further purification.

1,1,1-Trifluoro-3-(3-benzyloxy-biphenyl-3-yl)-2-propanone (35).

To a solution of acid 33 (0.08 g, 0.25 mmol) in anhydrous CH$_2$Cl$_2$ at room temperature, under nitrogen, was added oxalyl chloride (0.25 mL, 0.5 mmol) over a 2-min period. The mixture was stirred for 2 hours, solvent and excess oxalyl chloride were removed under reduced pressure, and the crude carboxylic acid chloride (34) was used in the next step without further purification.

To a solution of 34 in anhydrous CH$_2$Cl$_2$ at 0° C. under a nitrogen atmosphere were added successively trifluoroacetic anhydride (1 mL, 1.5 mmol) and dry pyridine (0.16 mmol, 0.16 mL). The reaction mixture was stirred at 0° C. for 10 min, and then it was allowed to warm to room temperature and stirred for an additional 2 hours period. Water was added dropwise at 0° C., the resulting mixture was warmed to room temperature, and extracted with $CH_2Cl_2$. The organic layer was washed with dilute aqueous HCl solution, and saturated aqueous $NaHCO_3$ solution, dried ($MgSO_4$) and the solvent was evaporated. Following the workup, the crude mixture was chromatographed on a silica gel column (eluting with 30% diethyl ether-hexane) to give compound 35 (0.033 g, 36% yield) as a viscous liquid.

$^1$H NMR (500 MHz, $CDCl_3$) δ 7.56 (d, J=8.0 Hz, 1H), 7.49 (d, J=7.0 Hz, 2H), 7.47-7.41 (m, 4H), 7.40-7.35 (m, 3H), 7.23-7.19 (m, 3H), 7.03 (dd, J=8.0 Hz, J=2.5 Hz, 1H), 5.15 (s, 2H), 4.01 (s, 2H).

Trifluoromethyl ketones 39.1-4 and 40.1, 40.3 (shown in Scheme 8) were synthesized by a method depicted in Scheme 8. Resorcinol dimethyl ether 36.1 and 4'-bromo-2,2,2-trifluoroacetophenone were commercially available starting materials while olivetol dimethyl ether 36.2 was synthesized following a method disclosed in Nikas, S. P et al., Synth. Commun., 2002, 32, 1751 and Nikas, S. P. et al., J. Labelled Compd. Radiopharm., 2002, 45, 1065, the contents of each of which is incorporated by reference. The required resorcinol dimethyl ethers 36.3 and 36.4 were synthesized by methylation of commercially available 4-hexylresorcinol and 4,6-dichlororesorcinol respectively.

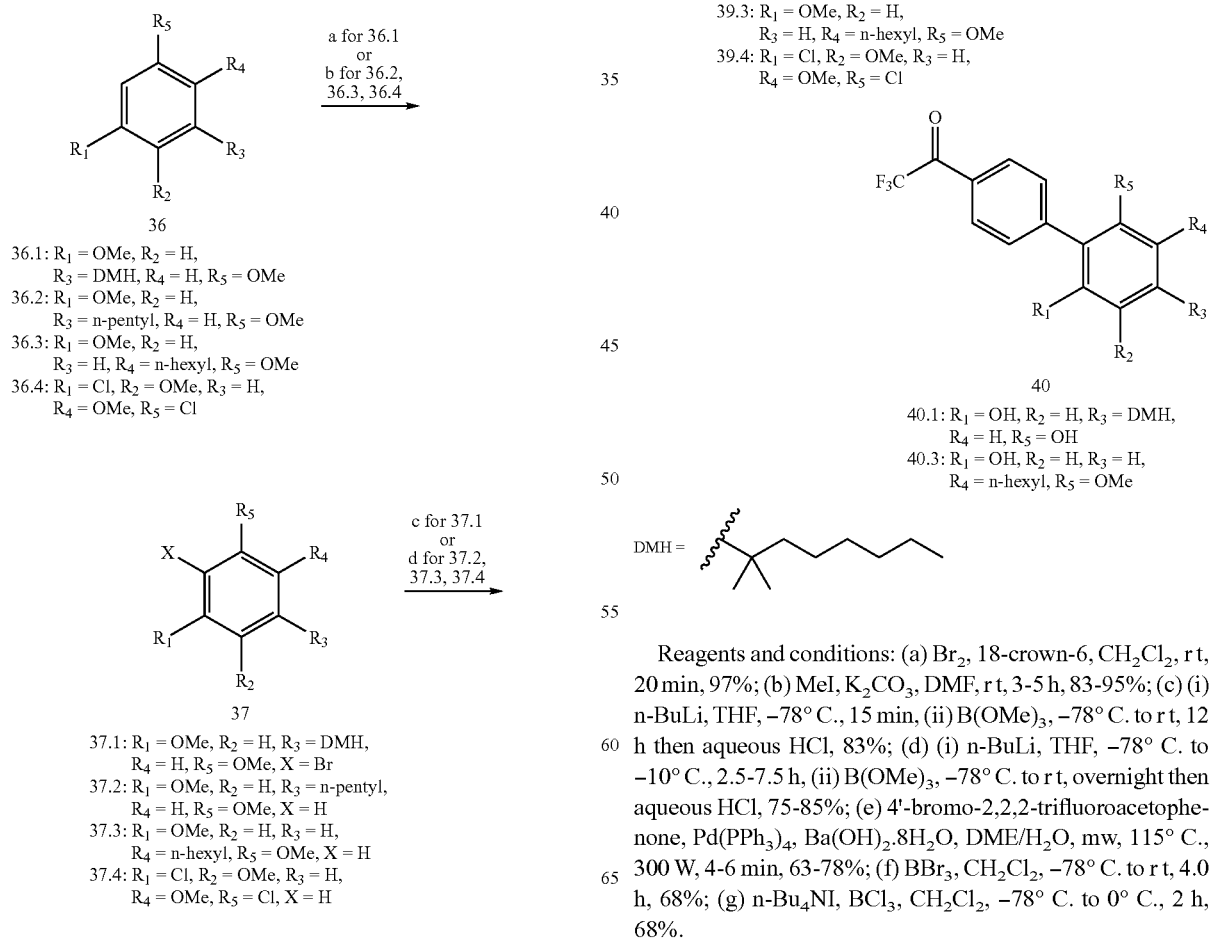

Reagents and conditions: (a) $Br_2$, 18-crown-6, $CH_2Cl_2$, r t, 20 min, 97%; (b) MeI, $K_2CO_3$, DMF, r t, 3-5 h, 83-95%; (c) (i) n-BuLi, THF, −78° C., 15 min, (ii) B(OMe)$_3$, −78° C. to r t, 12 h then aqueous HCl, 83%; (d) (i) n-BuLi, THF, −78° C. to −10° C., 2.5-7.5 h, (ii) B(OMe)$_3$, −78° C. to r t, overnight then aqueous HCl, 75-85%; (e) 4'-bromo-2,2,2-trifluoroacetophenone, Pd(PPh$_3$)$_4$, Ba(OH)$_2$.8H$_2$O, DME/H$_2$O, mw, 115° C., 300 W, 4-6 min, 63-78%; (f) BBr$_3$, $CH_2Cl_2$, −78° C. to r t, 4.0 h, 68%; (g) n-Bu$_4$NI, BCl$_3$, $CH_2Cl_2$, −78° C. to 0° C., 2 h, 68%.

Experimental Procedures:
Intermediates (37).
2-Bromo-5-(1,1-dimethylheptyl)-1,3-dimethoxybenzene (37.1).

To a vigorously stirred solution of 36.1 (2.09 g, 7.93 mmol) and 18-crown-6 in methylene chloride (70 mL) at room temperature was added bromine dropwise (0.43 mL, 8.30 mmol). Stirring was continued for 20 min, and the reaction mixture was successively washed with 10% sodium thiosulphate, saturated sodium bicarbonate solution and finally with brine. The organic layer was dried over $MgSO_4$ and evaporated, and the crude oil was purified by flash column chromatography (3% diethyl ether in hexane) to afford the title compound in 97% yield (2.66 g) as a colorless oil.

$^1$H NMR (500 MHz, $CDCl_3$) δ 6.54 (s, 2H), 3.90 (s, 6H), 1.58 (m, 2H), 1.29 (s, 6H), 1.25-1.19 (m, 6H), 1.05 (m, 2H), 0.85 (t, J=6.9 Hz, 3H).

Intermediates 37.2, 37.3 and 37.4.

A mixture of resorcinol 36.2 or 36.3 or 36.4 (1 equiv.), methyl iodide (2.2 equiv.) and potassium carbonate (2.5 equiv.) in anhydrous dimethylformamide was stirred for 3-5 hours at room temperature under an argon atmosphere. The reaction mixture was diluted with water and extracted with ethyl acetate. The organic phase was washed with water and brine, dried ($MgSO_4$), and the solvent was removed under reduced pressure. The residue was purified by flash column chromatography on silica gel (diethyl ether-hexane) to give the product in 83-95% yields.

Selected Data of Synthesized Intermediates 37.2, 37.3 and 37.4.

1,3-Dimethoxy-5-pentylbenzene (37.2).

$^1$H NMR (500 MHz, $CDCl_3$) δ 6.34 (d, J=2.0 Hz, 2H), 6.29 (t, J=2.0 Hz, 1H), 3.77 (s, 6H), 2.54 (t, J=7.2 Hz, 2H), 1.64-1.57 (m, 2H), 1.38-1.27 (m, 4H), 0.89 (t, J=7.3 Hz, 3H).

1,3-Dimethoxy-4-hexylbenzene (37.3)

$^1$H NMR (500 MHz, $CDCl_3$) δ 7.02 (d, J=8.5 Hz, 1H), 6.43 (d, J=2.5 Hz, 1H), 6.40 (dd, J=8.5 Hz, J=2.5 Hz, 1H), 3.78 (s, 3H), 3.77 (s, 3H), 2.52 (t, J=7.5 Hz, 2H), 1.56-1.50 (m, 2H), 1.36-1.25 (m, 6H), 0.88 (t, J=7.0, 3H).

Boronic Acids (38).

2,6-Dimethoxy-4-(2-methyloctane-2-yl)phenylboronic acid (38.1).

To a stirred solution of 37.1 (2.78 g, 8.0 mmol) in anhydrous THF (20 ml) under an argon atmosphere at −78° C. was added n-BuLi (5.5 ml, 8.8 mmol using 1.6 M solution in hexane) over a 30 min period. Stirring was continued at −78° C. for 15 min and then trimethyl borate (2.7 ml, 24 mmol) was added. Following addition, the reaction mixture was allowed to warm to room temperature over 12 hours period. The pH was adjusted to 6.5 by addition of 5% aqueous HCl solution at 0° C., and the mixture was extracted with dichloromethane. The organic layer was washed with brine, dried ($MgSO_4$) and the solvent was evaporated under reduced pressure. The residue was purified by flash column chromatography on silica gel (12% acetone in hexane) to give 38.1 as colorless oil, in 83% yield (2.1 g).

$^1$H NMR (500 MHz, $CDCl_3$) δ 6.54 (s, 2H), 3.89 (s, 6H), 1.55 (m, 2H), 1.26 (s, 6H), 1.19-1.23 (m, 6H), 1.05 (m, 2H), 0.85 (t, J=6.8 Hz, 3H).

Boronic Acids 38.2, 38.3, and 38.4.

To a solution of the resorcinol dimethyl ether (37.2 or 37.3 or 37.4, 1 equiv.) in dry THF, under an argon atmosphere at −78° C. was added n-BuLi dropwise (1.1 equiv. using a 1.6 solution in hexanes). The mixture was stirred for 1-6 h at −78° C., and then it was warmed to −10° C. and stirred for an additional 1.5 h. The reaction mixture was cooled to −78° C. and $(MeO)_3B$ (5 equiv.) was added. Following the addition, the mixture was warmed to room temperature and stirred overnight. The reaction was quenched by the dropwise addition of water, the pH was adjusted to 4 using a 5% aqueous HCl solution, and the mixture was extracted with AcOEt. The organic layer was washed with brine, dried ($MgSO_4$) and the solvent was evaporated under reduced pressure. The residue was purified by flash column chromatography on silica gel (acetone in hexane) to give boronic acid derivative (38.2 or 38.3 or 38.4) in 75-85% yields.

Selected Data of Synthesized Boronic Acids 38.2, 38.3, and 38.4.

4-Pentyl-2,6-dimethoxyphenyl boronic acid (38.2).

$^1$H NMR (500 MHz, $CDCl_3$) δ 7.18 (s, 2H), 6.45 (s, 2H), 3.90 (s, 6H), 2.61 (t, J=8.3 Hz, 2H), 1.63 (qt, J=6.9 Hz, 2H), 1.41-1.29 (m, 4H), 0.91 (t, J=7.2 Hz, 3H).

3-Hexyl-2,6-dimethoxyphenyl-boronic acid (38.3).

$^1$H NMR (500 MHz, $CDCl_3$) δ 7.28 (d, J=8.1 Hz, 1H), 6.72 (d, J=8.1 Hz, 1H), 3.89 (s, 3H), 3.78 (s, 3H), 2.57 (m as t, J=8.5 Hz, 2H), 1.62-1.56 (m, 2H), 1.37-1.29 (m, 6H), 0.89 (t, J=7.5 Hz, 3H).

Trifluoromethyl Ketones (39).

A degassed mixture of boronic acid 38 (1.1 equiv.) 4'-bromo-2,2,2-trifluoroacetophenone (1.0 equiv.), $Ba(OH)_2 \cdot 8H_2O$ (1.5 equiv.) $Pd(PPh_3)_4$ (0.03 equiv.), 1,2-dimethoxyethane and $H_2O$ was heated for 4-6 min at 115° C. under microwave irradiation (300 W) using a CEM Discover system. The reaction mixture was cooled to room temperature, diluted with ethyl acetate, and filtered through a short pad of silica gel. The filtrate diluted with brine and extracted with ethyl acetate. The organic layer was dried over $MgSO_4$, the solvent was evaporated, and the residue was purified by flash column chromatography on silica gel (acetone-hexane) to give 39 in 63-78% yields.

Selected Data of Synthesized Trifluoromethyl Ketones (39).

1-(2',6'-Dimethoxy-4'-pentylbiphenyl-4-yl)-2,2,2-trifluoroethanone (39.2).

$^1$H NMR (500 MHz, $CDCl_3$) δ 8.13 (d, J=38.1 Hz, 2H), 7.47 (d, J=8.1 Hz, 2H), 6.49 (s, 2H), 3.74 (s, 6H), 2.64 (t, J=7.8 Hz, 2H), 1.72-1.64 (m, 2H), 1.43-1.35 (m, 4H), 0.93 (t, J=7.5 Hz, 3H).

1-(2',6'-Dimethoxy-3'-hexylbiphenyl-4-yl) 2,2,2-trifluoroethanone (39.3).

$^1$H NMR (500 MHz, $CDCl_3$) δ 8.16 (d, J=8.5 Hz, 2H), 7.56 (d, 8.5 Hz, 2H), 7.17 (d, J=8.3 Hz, 1H), 6.73 (d, J=8.3 Hz, 1H), 3.73 (s, 3H), 3.27 (s, 3H), 2.61 (t, J=7.3 Hz, 2H), 1.61 (qt, J=6.8 Hz, 2H), 1.42-1.29 (m, 6H), 0.89 (t, J=7.1 Hz, 3H).

Trifluoromethyl Ketones (40).

1-(2',6'-dihydroxy-4'-(2-methyloctan-2-yl)biphenyl-4-yl)-2,2,2-trifluoroethanone (40.1).

To a solution of 39.1 (500 mg, 1.145 mmol) in dry dichloromethane at 0° C. under an argon atmosphere was added boron tribromide (2.8 mL, using 1M solution in $CH_2Cl_2$). Following the addition, the mixture was stirred until the reaction was completed (4 hours). Unreacted boron tribromide was destroyed by dropwise addition of water at 0° C. The resulting mixture was warmed to room temperature and diluted with dichloromethane. The organic layer was washed with saturated sodium bicarbonate solution, brine, dried over $MgSO_4$ and evaporated. Purification by flash column chromatography (18% acetone in hexane) gave the title compound in 68% yield (0.318 mg).

$^1$H NMR (500 MHz, $CDCl_3$) δ 8.21 (d, J=8.3 Hz, 2H), 7.68 (d, J=8.3 Hz, 2H), 6.54 (s, 2H), 4.77 (s, 2H, OH), 1.60-1.55 (m, 2H), 1.28 (s, 6H), 1.27-1.19 (m, 6H), 1.16-1.08 (m, 2H), 0.86 (t, J=6.5 Hz, 3H).

2,2,2-Trifluoro-1-(3'-hexyl-6'-hydroxy-2'-methoxybiphenyl-4-yl)ethanone (40.3).

Compound 39.3 (1 equiv.) and n-Bu$_4$NI (3 equiv.) were stirred in dry CH$_2$Cl$_2$ at −78° C. under nitrogen. A solution of BCl$_3$ (3.2 mL, using 1M solution in CH$_2$Cl$_2$) was added over 2 min period. After 5 min, the solution was warmed to 0° C. and stirring was continued for 2 h. The reaction was quenched with ice-water, the resulting mixture was stirred for 30 min, and partially concentrated to remove CH$_2$Cl$_2$. Water was added and the mixture was extracted with diethyl ether. The combined organic layer was washed with saturated aqueous NaCl solution, dried over MgSO$_4$, and evaporated. Purification by flash column chromatography on silica gel (18% acetone in hexane) gave the product 40.3 in 68% yield (270 mg).

$^1$H NMR (500 MHz, CDCl$_3$) δ 8.21 (d, J=8.0 Hz, 2H), 7.52 (d, J=8.0 Hz, 2H), 7.02 (d, J=8.3 Hz, 1H), 6.51 (d, J=8.3 Hz, 1H), 4.76 (s, 1H), 3.96 (s, 3H), 2.57 (t, J=7.8 Hz, 2H), 1.60 (qt, J=7.9 Hz, 2H), 1.42-1.28 (m, 6H), 0.89 (t, J=7.2 Hz, 3H).

4. Synthesis of Carbamates.

The carbamates 46.1, 46.2 or 46.3 shown in Scheme 9 were synthesized by a method depicted in Scheme 9 starting from commercially available 4-(4-methoxyphenyl)butanol (41).

Scheme 9

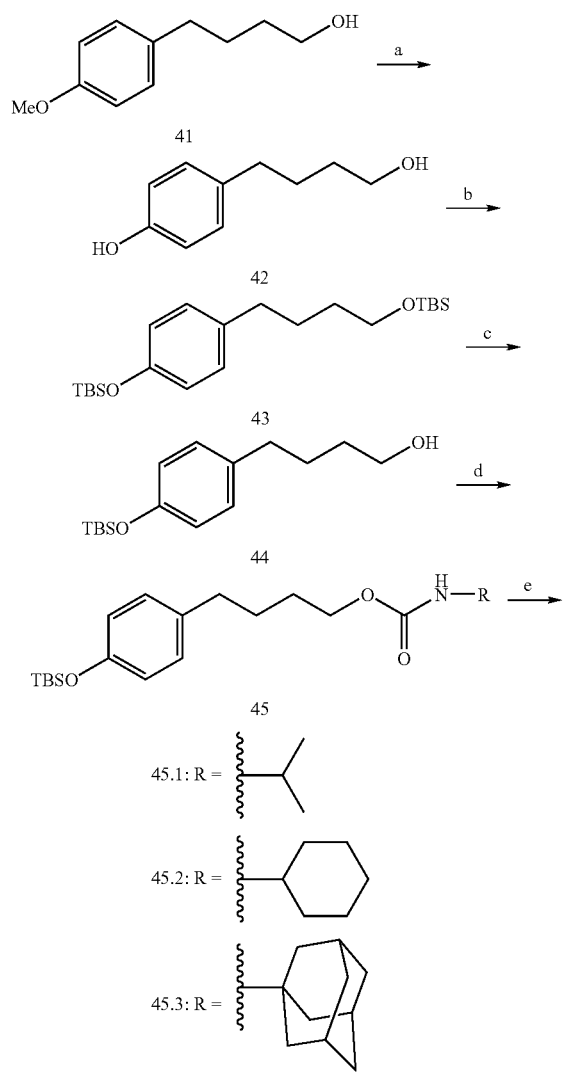

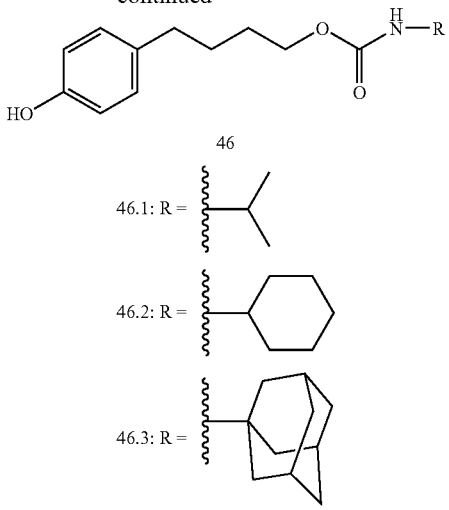

Reagents and conditions: (a) BBr$_3$, CH$_2$Cl$_2$, −10° C. to r t, 42%; (b) TBSCl, DMF, r t, 80%; (c) Sc(OTf)$_3$, MeCN/H$_2$O, r t, 73%; (d) (i) carbonyldiimidazole, CH$_2$Cl$_2$, 0° C., (ii) RNH$_2$, r t, 46-53%; (e) TBAF, THF, −10° C. to r t, 75-82%.

Experimental Procedures:

4-(4-Hydroxyphenyl)butanol (42).

To a stirred solution of 4-(4-methoxyphenyl)butanol (1 equiv.) in dry dichloromethane at −10° C. under an argon atmosphere was added boron tribromide (2.7 equiv., using a 1 M solution of boron tribromide in CH$_2$Cl$_2$). Stirring was continued at that temperature until completion of the reaction (4 hours). Unreacted boron tribromide was destroyed by addition of aqueous saturated NaHCO$_3$ solution at 0° C. The resulting mixture diluted with CH$_2$Cl$_2$ and water, the organic phase was separated, washed with brine, dried (MgSO$_4$) and evaporated. Purification by flash column chromatography on silica gel (30% diethyl ether-hexane) afforded the title compound in 42% yield.

1-(tert-Butyldimethylsilyloxy)-4-(tert-butyldimethylsilyloxybutyl)-benzene (43)

To a solution of imidazole (4 equiv.) in DMF was added 4-(4-hydroxyphenyl)butanol (1 equiv.) in DMF followed by tert-butyldimethylsilyl chloride (3 equiv.) in DMF. The reaction was allowed to stir at room temperature for 15 hours and then quenched by addition of saturated aqueous NaHCO$_3$ solution. The resulting mixture was extracted with diethyl ether, the ethereal extract was washed with water and brine, and dried over MgSO$_4$. Solvent evaporation and purification by flash column chromatography on silica gel (3% diethyl ether-hexane) afforded the title compound in 80% yield.

4-(4-tert-Butyldimethylsilyloxy)butanol (44).

To a solution of 1-(tert-butyldimethylsilyloxy)-4-(tert-butyldimethylsilyloxybutyl)-benzene (1 equiv.) in a mixture of acetonitrile/water (1:2.5) at room temperature was added scandium triflate (0.05 equiv.). The reaction mixture was stirred for 1 hour, diluted by addition of CH$_2$Cl$_2$ and the organic phase was separated. The aqueous phase was extracted with CH$_2$Cl$_2$ and the combined organic layer washed with brine, dried (MgSO$_4$) and evaporated. Purification by flash column chromatography on silica gel (20% diethyl ether-hexane) gave the title compound in 73% yield.

Intermediate Carbamates (45).

To a suspension of carbonyldiimidazole (1.5 equiv.) in anhydrous dichloromethane at 0° C. was added 4-(4-tertbutyldimethylsilyloxy)butanol (1 equiv.) in dichloromethane. The reaction mixture was stirred at room temperature for 1 hour and then the appropriate amine (1.1 equiv.) was added. Stirring was continued until completion of the reaction (8-10 hours). The reaction mixture was diluted with diethyl ether and 10% aqueous HCl solution. The organic phase was separated, washed with brine, dried (MgSO$_4$) and evaporated. Purification by flash column chromatography on silica gel (10% diethyl ether-hexane) gave intermediate carbamate 45 in 46-53% yield.

Carbamates (46).

To a stirred solution of intermediate carbamate 45 (1 equiv.) in THF at −10° C. was added dropwise tetra-n-butylammonium fluoride hydrate (1.3 equiv.) in THF. The reaction mixture was allowed to warm to room temperature, stirred for 1 hour and diluted with diethyl ether. The organic phase was separated, washed with water and brine, dried (MgSO$_4$) and evaporated. Purification by flash column chromatography on silica gel gave carbamate 46 in 75-82% yield.

Selected Data of Synthesized Carbamates (46):

4-(4-Hydroxyphenyl)butanol isopropylcarbamate (46.1). $^1$H NMR (400 MHz, CDCl$_3$) δ 7.01 (d, J=8.4 Hz, 2H), 6.76 (d, J=8.4 Hz, 2H), 4.55 (br s, 1H), 4.06 (t as br s, 2H), 3.81 (m, 1H), 2.54 (t, J=5.8 Hz, 2H), 1.71-1.59 (m, 4H), 1.14 (d, J=6.5 Hz, 6H).

4-(4-Hydroxyphenyl)butanol cyclohexylcarbamate (46.2). $^1$H NMR (400 MHz, CDCl$_3$) δ 6.99 (d, J=8.3 Hz, 2H), 6.75 (d, J=8.3 Hz, 2H), 6.23 (br s, 1H), 4.51 (br s, 1H), 4.05 (t as br s, 2H), 3.48 (m, 1H), 2.55 (t, J=5.8 Hz, 2H), 1.97-1.85 (m, 2H), 1.75-1.05 (m, 12H).

The carbamates 48.1-6, 52.1-4 and 53.1-4 shown in Scheme 10 were synthesized by a method depicted in Scheme 10 using commercially available 4-bromoaniline (47.1), 4-indoaniline (47.2), cyclohexanol, 1-adamantanyl, 2,6-difluorophenol, phenol, benzyl chloroformate, ethyl chloroformate, triphosgene, and the resorcinol derivative 49.

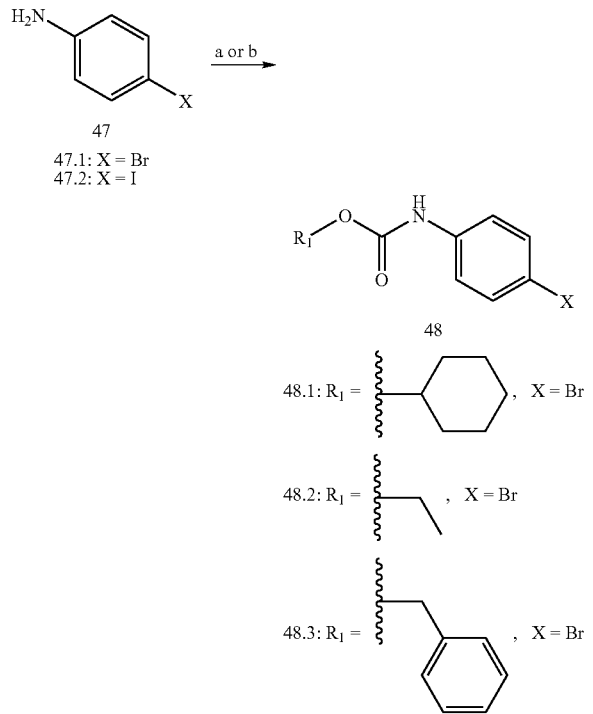

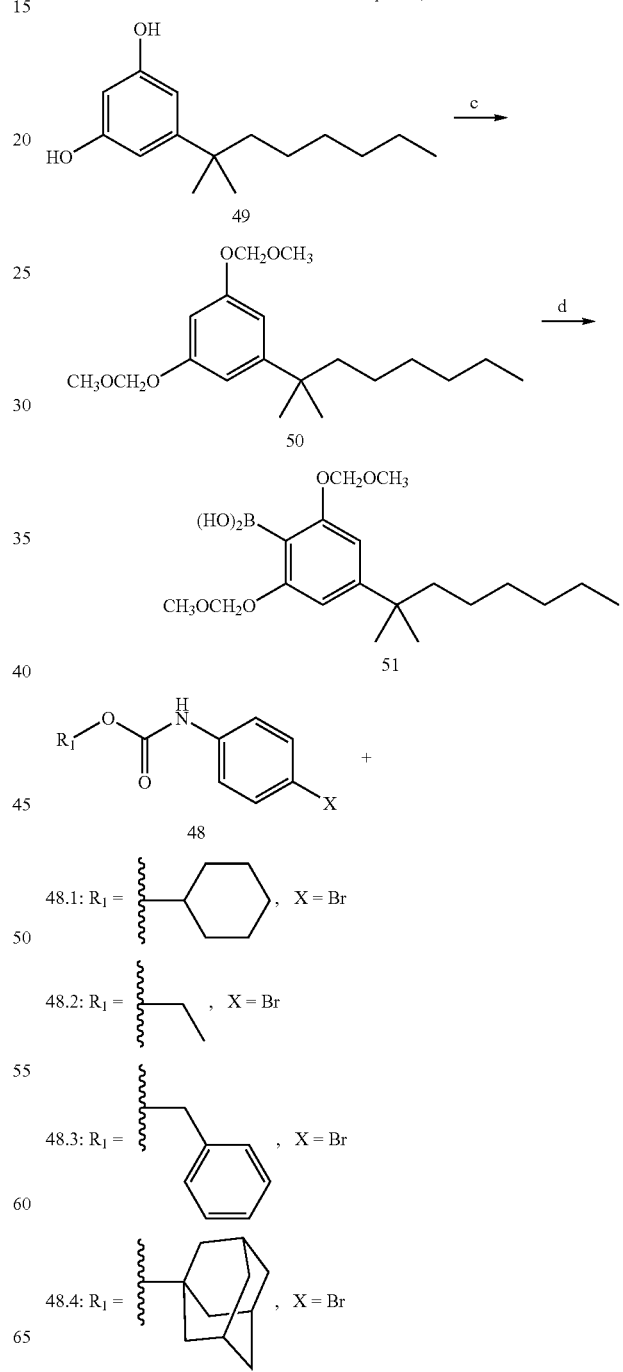

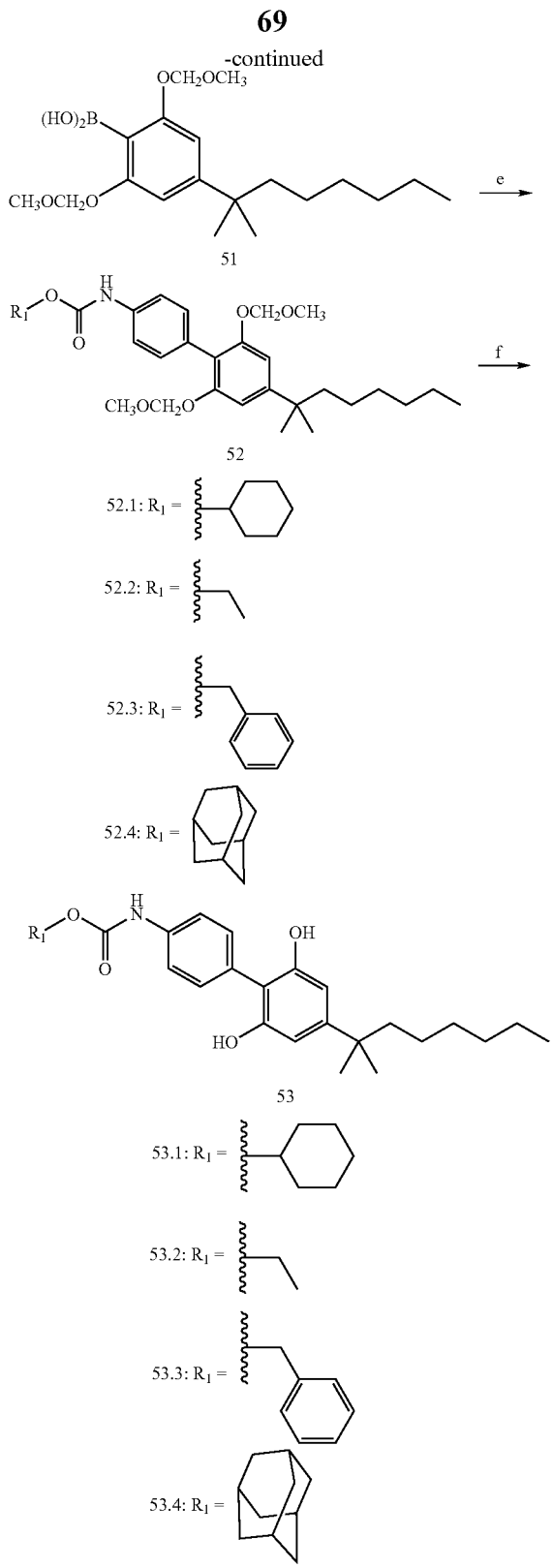

Reagents and conditions: (a) BnOCOCl or EtOCOCl, Na$_2$CO$_3$, toluene, r t, 4-6 h, 88-92%; (b) (i) (Cl$_3$CO)$_2$CO, toluene, reflux, 4-6 h, (ii) R$_1$OH, r t, 5 h, 70-78%; (c) CH$_3$OCH$_2$Cl, DIPEA, CH$_2$Cl$_2$, 0° C. to r t, 4 h, 75%; (d) (i) n-BuLi, −10° C., 1.5 h, (ii) B(OMe)$_3$, −78° C. to r t, overnight then aqueous HCl, 81%; (e) Pd(PPh$_3$)$_4$, Ba(OH)$_2$.8H$_2$O, DME/H$_2$O, m.w 110° C., 4-6 min, 58-77%; (f) 5N HCl, THF/i-PrOH, r t, 12-18 h, 60-72%.

Experimental Procedures:

Intermediate Carbamates (48).

Intermediate Carbamates 48.2, and 48.3.

To a stirred suspension of 4-bromoaniline 47.1 (1 equiv.) and sodium carbonate (1.5 equiv.) in anhydrous toluene at room temperature was added ethyl or benzyl chloroformate. Stirring was continued for 4-6 hours at the same temperature, insoluble materials were filtered off, and the filtrate was washed, with water and dried over MgSO$_4$. Solvent evaporation under reduced pressure and purification by flash column chromatography on silica gel (diethyl ether-hexane) gave pure products (48.2 or 48.3 respectively) in 88-92% yields.

Intermediate Carbamates 48.1, 48.4, 48.5, and 48.6.

To a stirred suspension of aryl amine (47.1 or 47.2) (1 equiv.) and sodium carbonate (1.5 equiv.) in anhydrous toluene, at room temperature under argon atmosphere was added triphosgene (1.2 equiv.). The reaction mixture was heated under reflux until TLC analysis indicated the total consumption of starting material (4-6 hours). The reaction mixture was cooled to room temperature, filtered, and the appropriate alcohol (1.1 equiv.) was added to the filtrate. The resulting mixture was stirred at room temperature for 5 hours and the solvent was evaporated under reduced pressure. Purification by flash column chromatography on silica gel gave the pure product in 70-78% yield.

Selected Data of Synthesized Intermediate Carbamates (48).

(4-Bromophenyl)carbamic acid cyclohexyl ester (48.1).

$^1$H NMR (500 MHz, CDCl$_3$) δ 7.40 (d, J=8.7 Hz, 2H), 7.28 (br d, J=8.7 Hz, 2H), 6.58 (br s, 1H, NH), 4.75 (m, 1H), 1.96-1.89 (m, 2H), 1.78-1.70 (m, 2H), 1.59-1.52 (m, 1H), 1.50-1.34 (m, 4H), 1.31-1.22 (m, 1H).

(4-Bromophenyl)carbamic acid benzyl ester (48.3).

$^1$H NMR (500 MHz, CDCl$_3$) δ 7.44-7.22 (m, 9H), 6.65 (br s, 1H, NH), 5.21 (s, 2H).

(4-Iodophenyl)carbamic acid phenyl ester (48.6).

$^1$H NMR (500 MHz, CDCl$_3$) δ 7.63 (d, J=8.5 Hz, 2H), 7.40 (t, J=8.5 Hz, 2H), 7.28-7.22 (m, 3H), 7.18 (d, J=8.0 Hz, 2H), 6.93 (br s, 1H, NH).

1,3-Bis(methoxymethoxy)-5-(1,1-dimethylheptyl)-benzene (50).

To a stirred solution of resorcinol (49) (1.00 g, 4.23 mmol) and N-ethyldiisopropylamine (3.04 mL, 16.92 mmol) in CH$_2$Cl$_2$ at 0° C. was added chloromethyl methyl ether (0.82 mL, 10.15 mmol) over 15 min period. The solution was warmed to room temperature, stirred for 4 hours and volatiles were removed in vacuo. The residue was purified by flash column chromatography on silica gel (diethyl ether-hexane) to give the title compound in 75% yield.

2,6-Bis(methoxymethoxy)-4-(1,1-dimethylheptyl)-phenyl boronic acid (51)

1,3-Bis(methoxymethoxy)-5-(1,1-dimethylheptyl)-benzene (50) (1 equiv.) was dissolved in dry THF (10 mL). The solution was cooled to −10° C. and n-BuLi (1.1 equiv. using 1.6 solution in hexanes) was added dropwise. The mixture was stirred for an additional 1.5 h, then it was cooled to −78° C. and (MeO)$_3$B (5 equiv.) was added. The reaction mixture was allowed to warm to room temperature and stirred overnight. The mixture was diluted with water, stirred for 30 min and the pH was adjusted to 4 with dilute aqueous HCl. The mixture was extracted with EtOAc, the organic layer was dried (MgSO$_4$) and the solvent was evaporated. Purification by flash column chromatography (hexane-acetone) gave the title compound in 81% yield.

¹H NMR (500 MHz, CDCl₃) δ 7.21 (s, 2H), 6.86 (s, 2H), 5.31 (s, 4H), 3.53 (s, 6H), 1.62-1.56 (m, 2H), 1.31-1.18 (m, 12H, especially 1.29, s, 6H), 1.12-1.04 (m, 2H), 0.87 (t, J=6.5 Hz, 3H).

Carbamates (52).

A degassed mixture of boronic acid (51) (1.1 equiv.), 4-bromo-2,2,2-trifluoroacetophenone (1.0 equiv.), Ba(OH)₂.8H₂O (1.5 equiv.), Pd(PPh₃)₄ (0.03 equiv.), 1,2-dimethoxy ethane and water was heated for 4-6 min at 110° C. under microwave irradiation using a CEM discover system. The reaction mixture was cooled to room temperature, diluted with ethyl acetate, and filtered through a short pad of silica gel. The filtrate diluted with brine and extracted with ethyl acetate. The organic layer was dried over MgSO₄, the solvent was evaporated, and the residue was purified by flash column chromatography on silica gel (acetone-hexane) to give product 52 in 58-77% yields.

Selected Data of Synthesized Carbamates (52).

2',6'-Bis(methoxymethoxy)-4'-(1,1-dimethylheptyl)[1,1'-biphenyl]-4-yl carbamic acid ethyl ester (52.2).

¹H NMR (500 MHz, CDCl₃) δ 7.40 (br d, J=8.9 Hz, 2H), 7.34 (d, J=8.9 Hz, 2H), 6.86 (s, 2H); 6.58 (br s, 1H, NH), 5.00 (s, 4H), 4.24 (q, J=7.5 Hz, 2H), 3.31 (s, 6H), 1.61-1.57 (m, 2H), 1.32 (t, J=7.5 Hz, 3H), 1.29 (s, 6H), 1.27-1.20 (m, 6H), 1.17-1.10 (m, 2H), 0.86 (t, J=7.6 Hz, 3H).

2',6'-Bis(ethoxymethoxy)-4'-(1,1-dimethylheptyl)[1,1'-biphenyl]-4-yl carbamic acid benzyl ester (52.3).

¹H NMR (500 MHz, CDCl₃) δ 7.43-7.33 (m, 9H), 6.86 (s, 2H), 6.68 (br s NH), 5.22 (s, 2H), 5.00 (s, 2H), 3.30 (s, 6H), 1.60-1.57 (m, 2H), 1.29 (s, 2H), 1.28-1.22 (m, 6H), 1.17-1.10 (m, 2H), 0.86 (t, J=7.0 Hz, 3H).

Carbamates (53).

To a stirred solution of 52 (1.0 equiv.) in isopropyl alcohol/THF mixture (1:1) were added few drops of 5N HCl solution. This mixture was stirred overnight at room temperature and evaporated to dryness. The residue was purified by flash column chromatography on silica gel (acetone-hexane) to give the product 53 in 60-72% yields.

Selected Data of Synthesized Carbamates (53).

2',6'-Dihydroxy-4'-(2-methyloctan-2-yl)biphenyl-4-yl carbamic acid cyclohexyl ester (53.1).

¹H NMR (500 MHz, CDCl₃) δ 7.59 (br d, J=8.3 Hz, 2H), 7.38 (d, J=8.3 Hz, 2H), 6.66 (br s, 1H, NH), 6.56 (s, 2H), 4.82-4.74 (m and s, overlapping, 3H, especially 4.76, s, 2H, OH), 1.99-1.93 (m, 2H), 1.79-1.74 (m, 2H), 1.61-1.54 (m, 2H), 1.52-1.37 (m, 6H), 1.33-1.18 (m and s, overlapping, 12H, especially 1.27, s, 6H, —C(CH₃)₂), 1.17-1.08 (m, 2H), 0.86 (t, J=7.0 Hz, 3H).

2',6'-Dihydroxy-4'-(1,1-dimethylheptyl)[1,1'-biphenyl]-4-yl carbamic acid ethyl ester (53.2).

¹H NMR (500 MHz, CDCl₃) δ 7.58 (br d, J=8.3 Hz, 2H), 7.38 (d, J=8.3 Hz, 2H), 6.68 (br s, 1H, NH), 6.56 (s, 2H), 4.74 (s, 2H, OH), 4.27 (q, J=7.5 Hz, 2H), 1.59-1.54 (m, 2H), 1.34 (t, J=7.5 Hz, 3H), 1.27 (s, 6H), 1.24-1.19 (m, 6H), 1.15-1.08 (m, 2H), 0.86 (t, J=7.2 Hz, 3H).

2',6'-Dihydroxy-4'-(2-methyloctane-2-yl)biphenyl-4-yl carbamic acid benzyl ester (53.3).

¹H NMR (500 MHz, CDCl₃) δ 7.59 (d, J=8.0 Hz, 2H), 7.44-7.36 (m, 7H), 6.77 (br s, 1H, NH), 6.56 (s, 2H), 5.23 (s, 2H), 4.73 (s, 2H), 1.58-1.55 (m, 2H), 1.28-1.18 (m and s, overlapping, 12H, especially 1.26, s, 6H, —C(CH₃)₂), 1.15-1.09 (m, 2H), 0.86 (t, J=7.0 Hz, 3H).

The carbamates 57.1 and 57.2 shown in Scheme 11 were synthesized by a method depicted in Scheme 11 starting from commercially available 4-bromobenzyl bromide (54).

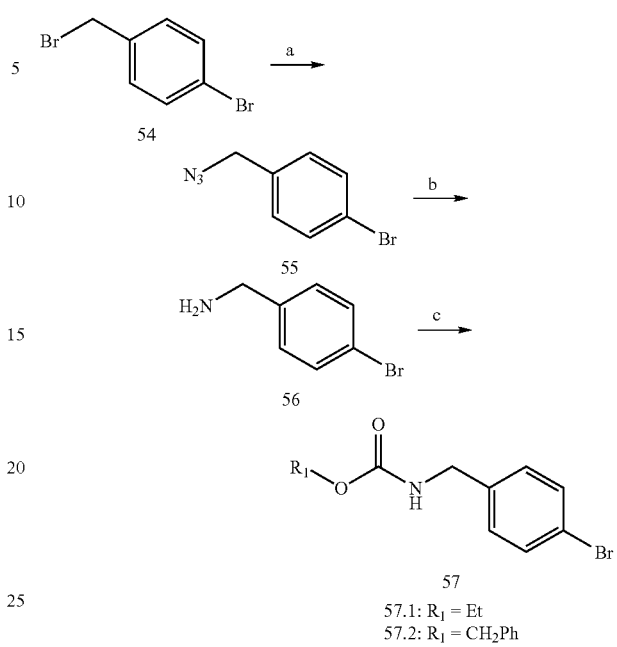

Scheme 11

57.1: R₁ = Et
57.2: R₁ = CH₂Ph

Reagents and conditions: (a) NaN₃, DMF, 50° C., 3 h, 92%; (b) PPh₃, THF/CH₃OH, reflux, 1.5 h, 63%; (c) R₁OCOCl, Na₂CO₃, toluene, r t, 4-6 h, 82-90%.

Experimental Procedures:

4-Bromobenzyl azide (55).

A mixture of 4-bromobenzyl bromide (54) and sodium azide (2.0 equiv.) in DMF was stirred at 50° C. for 3 h. The reaction mixture was diluted with water and extracted with CH₂Cl₂. The combined organic extract was dried over MgSO₄ and concentrated in vacuo. The residue was purified by flash chromatography to yield 55 as colorless oil in 92% yield.

¹H NMR (500 MHz, CDCl₃) δ 7.51 (d, J=8.5 Hz, 2H), 7.19 (d, J=8.5 Hz, 2H), 4.31 (s, 2H). IR (Neat): 2091, 1592, 1488 cm⁻¹.

4-Bromobenzyl Amine (56).

To a stirred solution of azide 55 (0.75 g, 3.54 mmol) in anhydrous methanol (10 mL) was added triphenylphosphine (1.39 g, 5.31 mmol) and the mixture was heated under reflux for 1.5 hours. The reaction mixture was cooled to room temperature and the solvent was removed under reduced pressure. The residue was purified by flash column chromatography on silica gel (acetone-hexane) to yield product 56 in 63% yield (0.41 g).

Carbamates (57).

To a stirred suspension of 4-bromobenzyl amine 56 (1 equiv.) and sodium carbonate (1.5 equiv.) in anhydrous toluene at room temperature was added ethyl or benzyl chloroformate. Stirring was continued for 4-6 hours at the same temperature, insoluble materials were filtered off, and the filtrate was washed with water and dried over MgSO₄. Solvent evaporation under reduced pressure and purification by flash column chromatography on silica gel (diethyl ether-hexane) gave pure product (57.1 or 57.2 respectively) in 82-90% yields.

Selected Data of Synthesized Carbamates (57).

(4-Bromobenzyl)carbamic acid benzyl ester (57.2).

¹H NMR (500 MHz, CDCl₃) δ 7.44 (d, J=7.7 Hz, 2H), 7.38-7.30 (m, 5H), 7.16 (d, J=7.7 Hz, 2H), 5.13 (s, 2H), 5.09 (br s, 1H, NH), 4.32 (d, J=5.5 Hz, 2H).

5. Synthesis of Ureas.

Ureas 59.1 and 59.2 (shown in Scheme 12) were synthesized by a method depicted in Scheme 12 starting from commercially available 3-phenyl-propyl isocyanate (58) and 2-aminomethyl-pyridine or 2-aminopyridine.

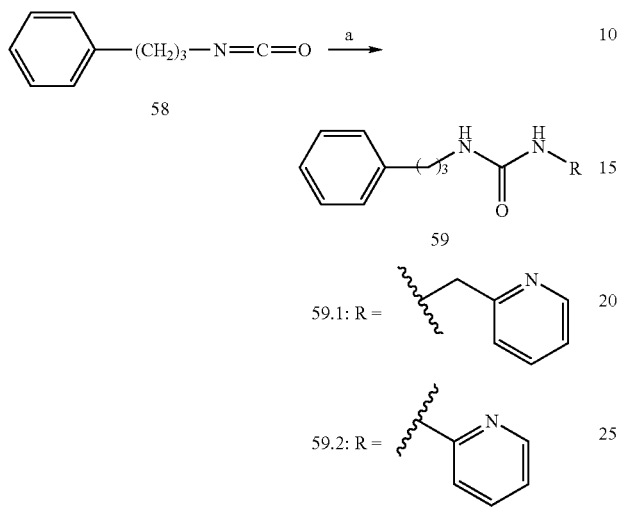

Reagents and conditions: (a) R—NH$_2$, THF or benzene, 0° C. to reflux 85-93%.

Experimental Procedures:

N-(3-phenylpropyl)-N'-(2-pyridinylmethyl)-urea (59.1)

To a solution of 3-phenylpropyl isocyanate (1.8 mmol) in anhydrous THF (10 mL) at 0° C. under an argon atmosphere was added 2-aminomethyl-pyridine (1.8 mmol). The reaction mixture was stirred at 0° C. for 10 min, the solvent was evaporated under reduced pressure, and the resultant solid was recrystallized from CH$_2$Cl$_2$/Et$_2$O to give pure 59.1 in 92% yield. White solid. m p 89-90° C. When anhydrous benzene was used as solvent the product was directly crystallized out and isolated by filtration (93% yield).

$^1$H NMR (500 MHz, CDCl$_3$) δ 8.47 (d, J=4.4 Hz, 1H), 7.61 (td, J=7.6 Hz, J=1.1 Hz, 1H), 7.28-7.22 (m, 3H), 7.19-7.10 (m, 4H), 5.97 (t, J=4.9 Hz, 11H, NH), 5.30 (br s, 11H, NH), 4.45 (d, J=5.4 Hz, 2H), 3.20 (td as q, J=6.4 Hz, 2H), 2.61 (t, J=7.6 Hz, 2H), 1.79 (quintet, J=7.3 Hz, 2H); IR (neat), 3320, 3028, 2941, 2860, 1620, 1594, 1568, cm$^{-1}$.

N-(3-phenylpropyl)-N'-(2-pyridinyl)-urea (59.2).

To a stirred solution of 3-phenylpropyl isocyanate (2 mmol) in anhydrous THF (15 mL) at 0° C. under an argon atmosphere was added 2-amino-pyridine (2 mmol). Following the addition, the reaction mixture was heated under reflux for 2 h, the solvent was evaporated under reduced pressure, and the resultant solid was recrystallized from CH$_2$Cl$_2$/Et$_2$O to give pure 59.2 in 85% yield. White solid. m p 127-128° C.

$^1$H NMR (500 MHz, CDCl$_3$) δ 9.72 and 9.66 (s and br s, overlapping, 2H, NH), 8.16 (d, J=4.3 Hz, 1H), 7.58 (t, J=7.1 Hz, 1H), 7.30 (t, J=7.4 Hz, 2H), 7.24 (d, J=7.4 Hz, 2H), 7.21 (t, J=7.4 Hz, 1H), 6.94 (d, J=7.1 Hz, 1H), 6.87 (m as t, J=6.4 Hz, 1H), 3.44 (td as q, J=6.4 Hz, 2H), 2.75 (t, J=7.6 Hz, 2H), 1.97 (quintet, J=7.2 Hz, 2H); IR (neat) 3221, 3054, 2980, 2918, 1682, 1602, 1583, 1549, 1480 cm$^-$.

6. Synthesis of α-Keto-Heterocycles.

α-Keto-oxadiazoles 65.1, 65.2 and 66 (shown in Scheme 13) were synthesized by a method depicted in Scheme 13 starting from 60.1 or 60.2 and 2-methyl-oxadiazole (63).

Phenol (60.1) and 4-benzyloxy-phenol (60.2) were commercially available while 2-methyl-oxadiazole (63) was prepared by a method disclosed in Ainsworth, C et al., J. Org. Chem. Soc., 1966, 31, 3442-3444 and in Ohmoto, K et al., J. Med. Chem., 2001, 44, 1268-1285, the contents of each of which is incorporated by reference.

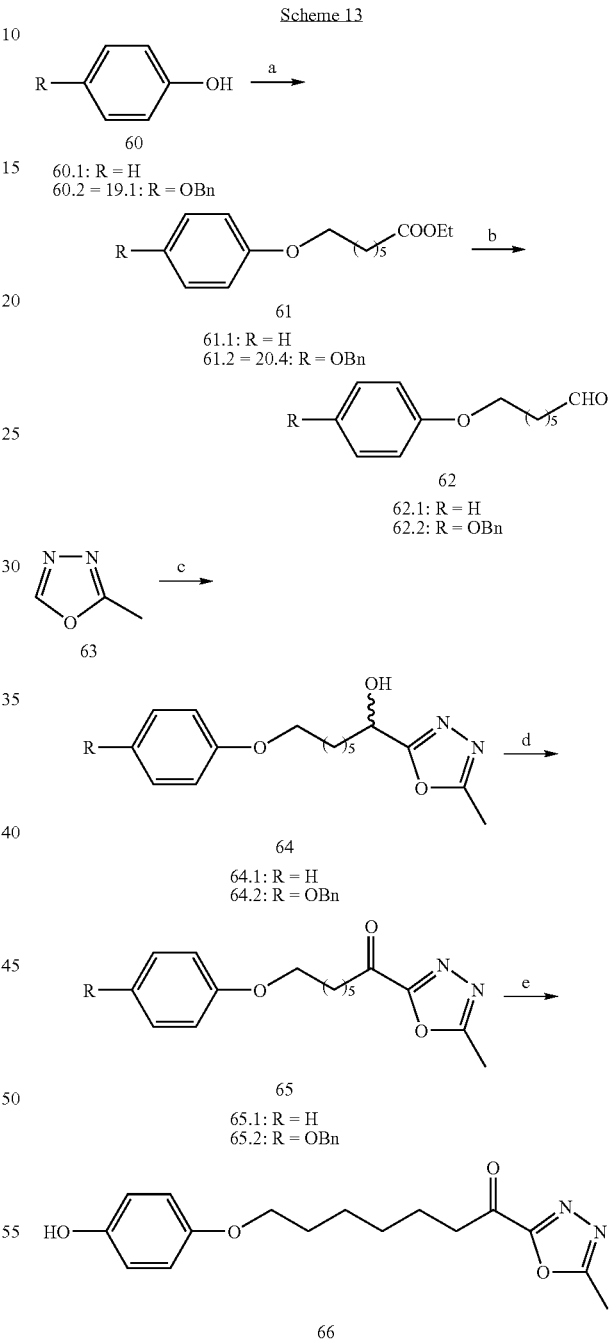

Reagents and conditions: (a) Br(CH$_2$)$_6$COOEt, K$_2$CO$_3$, 18-crown-6, acetone, 50° C., 12 h, 90-92%; (b) DIBAL-H, THF, −78° C., 1 h, 63-65%; (c) n-BuLi, MgBr$_2$.Et$_2$O, THF −78° C. to −50° C., then addition to 62.1 or 62.2, CeCl$_3$, −78° C., 52-55%; (d) Dess-Martin periodinane, CH$_2$Cl$_2$, r t, 80-82%; (e) Pd/C, H$_2$, AcOEt, r t, 71%.

Experimental Procedures:
7-(Phenoxy)heptanoic acid ethyl ester (61.1).

To a solution of 60.1 (0.7 g, 7.5 mmol) in dry acetone (50 mL), under a nitrogen atmosphere, was added 18-crown-6 (1.584 g, 6 mmol), anhydrous potassium carbonate (2.07 g, 15 mmol), and ethyl 7-bromoheptanoate (1.18 g, 5 mmol) successively. The mixture was stirred at 50° C. overnight and then it was cooled to room temperature and the solvent removed in vacuo. The residue obtained was partitioned between diethyl ether (50 mL), and water (10 mL). The organic phase was separated and the aqueous layer extracted with diethyl ether. The combined organic layer was washed with brine, dried ($MgSO_4$) and the solvent was removed under reduced pressure. Purification by flash column chromatography (20% diethyl ether-hexane) afforded 61.1 (1.72 g, 92% yield) as a colorless liquid.

$^1$H NMR (500 MHz, $CDCl_3$) δ 7.27 (dt, J=7.7 Hz, J=1.5 Hz, 2H), 6.92 (dt, J=7.7 Hz, J=1.5 Hz 1H), 6.89 (d, J=7.7 Hz, 2H), 4.12 (q, J=7.0 Hz, 2H), 3.95 (t, J=6.2 Hz, 2H), 2.31 (t, J=7.7 Hz, 2H), 1.78 (quintet, J=6.5 Hz, 2H), 1.66 (quintet, J=7.5 Hz, 2H), 1.49 (quintet, J=7.2 Hz, 2H), 1.40 (quintet, J=8.2, 2H), 1.25 (t, J=7.0 Hz, 2H).

7-[4-(Benzyloxy)phenoxy]heptanoic acid ethyl ester (61.2/20.4). An alternative method for the synthesis of the title compound was carried out analogous to the preparation of 61.1 using 60.2 (0.45 g, 2.255 mmol), 18-crown-6 (1.056 g, 4 mmol), potassium carbonate (1.38 g, 10 mmol), and $Br(CH_2)_6COOEt$, (0.8 g, 3.37 mmol) in dry acetone (40 mL). Purification by flash column chromatography on silica gel (20% diethyl ether-hexane) gave 61.2/20.4 (1.08 g, 90% yield) as a white solid (m p 57-61° C.).

$^1$H NMR (500 MHz, $CDCl_3$) δ 7.42 (d, J=7.5 Hz, 2H), 7.37 (t, J=7.5 Hz, 2H), 7.31 (t, J=7.5 Hz, 1H), 6.89 (d, J=8.7 Hz, 2H), 6.82 (d, J=8.7 Hz, 2H), 5.01 (s, 2H), 4.12 (q, J=7.0 Hz, 2H), 3.89 (t, J=6.5 Hz, 2H), 2.30 (t, J=7.5 Hz, 2H), 1.76 (quintet, J=6.7 Hz, 2H), 1.66 (quintet, J=7.5 Hz, 2H), 1.47 (quintet, J=7.2 Hz, 2H), 1.38 (quintet, J=6.7 Hz, 2M), 1.25 (t, J=7.0 Hz, 2H).

7-(Phenoxy)heptanal (62.1).

To a stirred solution of 61.1 (0.56 g, 2.24 mmol) in dry THF (20 mL), at −78° C., under a nitrogen atmosphere was added diisobutylaluminum hydride (5 mL, 5 mmol, using a 1M solution in hexanes) dropwise. The reaction mixture was stirred at the same temperature for 30 min and then quenched by dropwise addition of potassium sodium tartrate (10% solution in water). The resulting mixture was warmed to room temperature and stirred vigorously for 1 h. The organic layer was separated and the aqueous phase extracted with diethyl ether. The combined organic layer was washed with brine, dried ($MgSO_4$) and concentrated in vacuo. The residue was purified by column chromatography on silica gel, eluting with 25% diethyl ether-hexane to give 62.1 (0.26 g, 65% yield) as a colorless viscous liquid.

$^1$H NMR (500 MHz, $CDCl_3$) δ 9.80 (s, 1H), 7.27 (t, J=7.5 Hz, 2H), 6.93 (d, J=7.5 Hz, 2H), 6.89 (d, J=7.5 Hz, 2H), 3.95 (t, J=6.2 Hz, 2H), 2.45 (t, J=7.2 Hz, 2H), 1.79 (quintet, J=6.7 Hz, 2H), 1.67 (quintet, J=7.0 Hz, 2H), 1.50 (quintet, J=6.7 Hz, 2H), 1.41 (quintet, J=7.7 Hz, 2H).

7-[4-(Benzyloxy)phenoxy]heptanal 62.2 was synthesized analogous to the preparation of 62.1 using 61.2/20.4 (0.624 g, 2 mmol) and diisobutylaluminum hydride (4.5 mL, 4.5 mmol, using a 1M solution in hexanes) in THF (20 mL). Purification by flash column chromatography on silica gel gave 62.2 (0.39 g, 63% yield) as a white solid (m p 65-67° C.).

$^1$H NMR (500 MHz, $CDCl_3$) δ 9.80 (s, 1H), 7.42 (d, J=7.2 Hz, 2H), 7.38 (t, J=7.2 Hz, 2H), 7.31 (t, J=7.2 Hz, 1H), 6.90 (d, J=8.7 Hz, 2H), 6.82 (d, J=8.7 Hz, 2H), 5.01 (s, 2H), 3.90 (t, J=6.2 Hz, 2H), 2.44 (dt, J=7.2 Hz, J=2.0 Hz, 2H), 1.76 (quintet, J=7.5 Hz, 2H), 1.67 (quintet, J=7.5 Hz, 2H), 1.48 (quintet, J=7.2 Hz, 2H), 1.40 (quintet, J=7.7 Hz, 2H).

7-Phenoxy-1-(5-methyl-1,3,4-oxadiazol-2-yl)-heptan-1-ol (64.1).

To a stirred solution of 63 (0.252 g, 3 mmol) in anhydrous THF (5 mL), at −78° C., under a nitrogen atmosphere, was added n-BuLi (1.2 mL, 3 mmol, using a 2.5 M solution in hexanes) dropwise. Stirring was continued for 15 min at −78° C. and then $MgBr_2.Et_2O$ (0.774 g, 3 mmol) was added. The resulting mixture was warmed to −50° C. over a 2 hours period, and then it was transferred by cannula to a cooled (−78° C.) slurry of 62.1 (0.125 g, 0.6 mmol) and $CeCl_3$, (0.738 g, 3 mmol) in anhydrous THF (6 mL), which was previously stirred at room temperature for 2 hours under nitrogen. Following the addition, the resultant mixture was allowed to warm to room temperature over a 4 hours period. The reaction mixture was quenched with dropwise addition of 5% aqueous AcOH solution (10 mL), diluted with AcOEt (20 mL) and the organic phase was separated. The aqueous layer extracted with AcOEt, the combined organic layer was washed with aqueous saturated $NaHCO_3$ solution and brine, dried ($MgSO_4$) and the solvent was evaporated under reduced pressure. The residue obtained was purified by flash column chromatography on silica gel (75% ethyl acetate-hexane) to give 64.1 (92.5 mg, 53% yield) as a white solid (m p 50-52° C.).

$^1$H NMR (500 MHz, $CDCl_3$) δ 7.27 (t, J=7.7 Hz, 2H), 6.93 (t, J=7.7 Hz, 1H), 6.89 (d, J=7.7 Hz, 2H), 4.91 (t, J=6.2 Hz, 1H), 3.95 (t, J=6.7 Hz, 2H), 2.80 (br s, 1H), 2.54 (s, 3H), 1.98-1.90 (m, 2H), 1.78 (quintet, J=6.7 Hz, 2H), 1.54-1.40 (m, 6H).

7-(4-Benzyloxy-phenoxy)-1-(5-methyl-1,3,4-oxadiazol-2-yl)-heptan-1-ol (64.2). The synthesis was carried out analogous to the preparation of 64.1 using 62.2 (0.1 g, 0.32 mmol), cerium chloride (0.44 g, 1.6 mmol) and 63 (0.42 g, 1.6 mmol). Purification by flash column chromatography on silica gel gave pure 64.2 (0.077 mg, 55% yield) as a white solid (m p 98-100° C.).

$^1$H NMR (500 MHz, $CDCl_3$) δ 7.42 (d, J=7.5 Hz, 2H), 7.38 (t, J=7.5 Hz, 2H), 7.31 (t, J=7.5 Hz, 1H), 6.90 (d, J=8.7 Hz, 2H), 6.82 (d, J=8.7 Hz, 2H), 5.01 (s, 2H), 4.90 (q, J=6.0 Hz, 1H), 3.89 (t, J=6.5 Hz, 2H), 2.54 (s, 3H), 2.51 (d, J=6.0 Hz, 1H), 2.00-1.92 (m, 2H), 1.75 (quintet, J=7.5 Hz, 2H), 1.56-1.40 (m, 6H).

7-Phenoxy-1-(5-methyl-1,3,4-oxadiazol-2-yl)-heptan-1-one (65.1).

To a solution of 64.1 (64 mg, 0.22 mmol) in wet methylene chloride (5 mL) at room temperature, under nitrogen was added Dess-Martin periodinane (140 mg, 0.33 mmol) and the resulting suspension stirred for 2 hours. The reaction mixture was diluted with $Na_2S_2O_3$ (10% in $H_2O$) and saturated aqueous $NaHCO_3$ solution and the organic phase was separated. The aqueous layer was extracted with AcOEt and the combined organic layer was washed with brine, dried ($MgSO_4$) and evaporated under reduced pressure. The residue obtained was purified by flash column chromatography on silica gel (50% ethyl acetate-hexane) to give 65.1 (52 mg, 82% yield) as a white solid (m p 75-77° C.).

$^1$H NMR (500 MHz, $CDCl_3$) δ 7.27 (t, J=7.5 Hz, 2H), 6.93 (t, J=7.5 Hz, 1H), 6.89 (d, J=7.5 Hz, 2H), 3.95 (t, J=6.2 Hz, 2H), 3.15 (t, J=7.2 Hz, 2H), 2.64 (s, 3H), 1.84-1.77 (m, 4H), 1.52-1.44 (m, 4H).

7-(4-Benzyloxy-phenoxy)-1-(5-methyl-1,3,4-oxadiazol-2-yl)-heptan-1-one (65.2). The synthesis was carried out analogous to the preparation of 65.1 using 64.2 (60 mg, 0.15 mmol) and Dess-Martin periodinane (0.127 g, 0.3 mmol) in wet CH$_2$Cl$_2$ (5 mL). Purification by flash column chromatography on silica gel gave pure compound 65.2 (47.5 mg, 80% yield) as a white solid (m p 118-120° C.).

$^1$H NMR (500 MHz, CDCl$_3$) δ 7.42 (d, J=7.5 Hz, 2H), 7.38 (t, J=7.5 Hz, 2H), 7.31 (t, J=7.5 Hz, 1H), 6.90 (d, J=8.7 Hz, 2H), 6.82 (d, J=8.7 Hz, 2H), 5.01 (s, 2H), 3.90 (t, J=6.2 Hz, 2H), 3.14 (t, J=7.5 Hz, 2H), 2.64 (s, 3H), 1.84-1.74 (m, 4H), 1.54-1.44 (m, 4H).

7-(4-Hydroxy-phenoxy)-1-(5-methyl-1,3,4-oxadiazol-2-yl)-heptan-1-one (66). To a solution of 65.2 (30 mg, 0.076 mmol) in AcOEt (5 mL) was added 10% Pd/C (6 mg, 20% w/w) and the resulting suspension was stirred vigorously under hydrogen atmosphere, overnight at room temperature. The catalyst was removed by filtration through Celite, and the filtrate was evaporated under reduced pressure. The residue obtained was purified by flash column chromatography on silica gel (60% ethyl acetate-hexane) to give pure compound 66 (0.016 g, 71% yield) as a white solid (m p 134-135° C.).

$^1$H NMR (500 MHz, CDCl$_3$) δ 6.80-6.74 (m, 4H), 4.56 (br s, 1H), 3.89 (t, J=6.5 Hz, 2H), 3.14 (t, J=7.2 Hz, 2H), 2.64 (s, 3H), 1.84-1.74 (m, 4H), 1.54-1.44 (m, 4H).

α-Keto-oxadiazoles 73.1, 73.2 74.1 and 74.2 (shown in Scheme 14) were synthesized by a method depicted in Scheme 14 starting from 7-(phenoxy)heptanoic acid ethyl ester (61.1), 7-[4-(benzyloxy)phenoxy]heptanoic acid ethyl ester (61.2), and commercially available methyl glycolate (69).

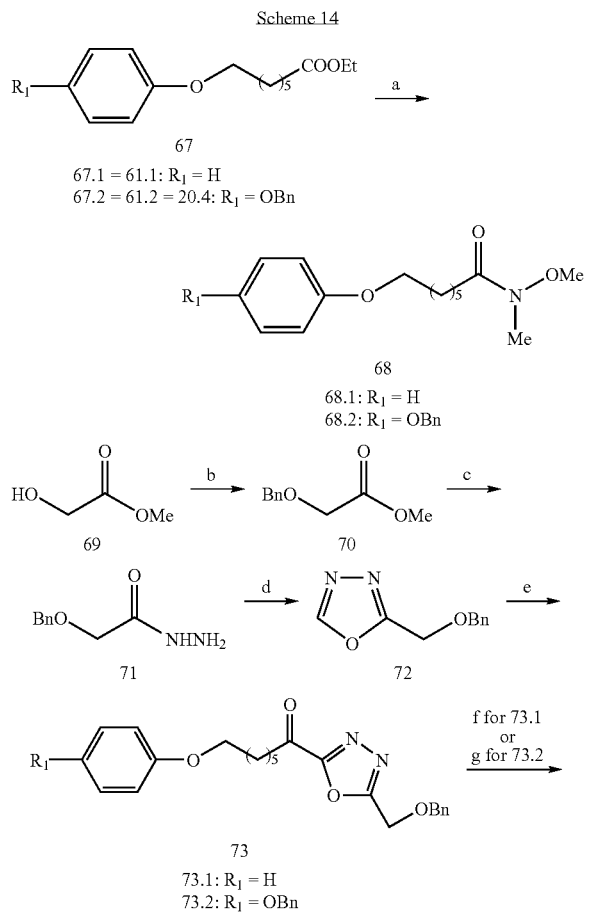

Scheme 14

67
67.1 = 61.1: R$_1$ = H
67.2 = 61.2 = 20.4: R$_1$ = OBn 68
68.1: R$_1$ = H
68.2: R$_1$ = OBn 73
73.1: R$_1$ = H
73.2: R$_1$ = OBn

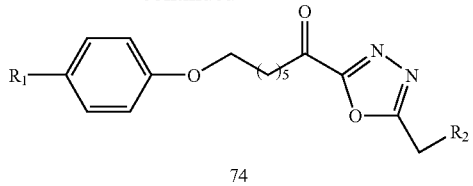

74
74.1: R$_1$ = H, R$_2$ = OH
74.2: R$_1$ = OH, R$_2$ = OBn

Reagents and conditions: (a) (MeO)MeNH$_2$$^{+Cl-}$, n-BuLi, THF, −78-C, 15 min, then addition of 67, −78° C., 40 min, 85-87%; (b) BnBr, Ag$_2$O, Et$_2$O, r t, 24 h, 70%; (c) H$_2$NNH$_2$.H$_2$O, MeOH, reflux, 3 h; (d) CH(OMe)$_3$, p-TSA, reflux, 3 h, 49% from 70; (e) n-BuLi, MgBr$_2$.Et$_2$O, THF −78° C. to −30° C., 2 h, then addition of 68.1 or 68.2, −30° C. to 0° C., 4 h, 53-55%. (f) 1,4-cyclohexadiene, 10% Pd/C, AcOH/MeOH, 45° C., 2 h, 25%; (g) H$_2$, 10% Pd/C, AcOEt, r t, overnight, 75%.

Experimental Procedures:

7-Phenoxy-(N-methoxy-N-methyl)-heptane-carboxamide (68.1). The title compound was synthesized analogously to 68.2 (see experimental below), using dry N,O-dimethylhydroxyl amine hydrochloride (488 mg, 5 mmol) in anhydrous THF (40 mL), n-BuLi (2.5 M solution in hexanes, 4 mL, 10 mmol) and 67.2 (250 mg, 1 mmol). The crude obtained after workup was chromatographed over a column of silica gel, eluting with 50% ethyl acetate-petroleum ether to afford 68.1 as a colorless liquid in 87% yield (230 mg).

$^1$H NMR (500 MHz, CDCl$_3$) δ 7.27 (t, J=8.0 Hz, 2H), 6.92 (t, J=8.0 Hz, 1H), 6.89 (d, J=8.0 Hz, 2H), 3.95 (t, J=6.5 Hz, 2H), 3.68 (s, 3H), 3.18 (s, 3H), 2.43 (t, J=7.5 Hz, 2H), 1.79 (quintet, J=6.5 Hz, 2H), 1.67 (quintet, J=7.5 Hz, 2H), 1.50 (quintet, J=7.0 Hz, 2H), 1.42 (quintet, J=7.0 Hz, 2H).

7-[(4-Benzyloxy-phenoxy)-N-methoxy-N-methyl]-heptane-carboxamide (68.2). To a stirred suspension of N,O-dimethylhydroxylamine hydrochloride (dry, 680 mg, 7 mmol) in anhydrous THF (40 mL) at −78° C., under an argon atmosphere, was added n-BuLi (2.5 M solution in hexanes, 5.6 mL, 14 mmol) dropwise. The mixture was stirred for 15 minutes after removing the dry ice/acetone bath (to ensure complete dissolution of the salt), cooled again to −78° C., and a solution of 67.1 (500 mg, 1.4 mmol) in anhydrous THF (10 mL) was added dropwise. The reaction mixture was stirred for an additional 40 minutes at the same temperature and diluted with aqueous NH$_4$Cl and the resulting mixture warmed to room temperature. The organic layer was separated and the aqueous layer extracted with ethyl acetate (2×20 mL). The combined organic layer was washed with brine (20 mL), dried over MgSO$_4$ and the solvent evaporated under reduced pressure. The crude product was chromatographed over a column of silica gel, eluting with 50% ethyl acetate-petroleum ether to afford 68.2 as a white solid (m p 54-55° C.) in 85% yield (440 mg).

$^1$H NMR (500 MHz, CDCl$_3$) δ 7.42 (d, J=7.0 Hz, 2H), 7.37 (t, J=7.0 Hz, 2H), 7.32 (t, J=7.0 Hz, 1H), 6.90 (d, J=9.0 Hz, 2H), 6.81 (d, J=9.0 Hz, 2H), 5.01 (s, 2H), 3.90 (t, J=6.2 Hz, 2H), 3.68 (s, 3H), 3.18 (s, 3H), 2.43 (t, J=7.5 Hz, 2H), 1.77 (quintet, 3=6.7 Hz, 2H), 1.67 (quintet, J=7.7 Hz, 2H), 1.48 (quintet, J=7.7 Hz, 2H), 1.40 (quintet, J=7.5 Hz, 2H).

Methyl-2-benzyloxy-acetate (70). To a stirred solution of methyl glycolate (2 g, 22.2 mmol) in anhydrous diethyl ether (100 mL), at room temperature, under a nitrogen atmosphere, was added silver(I)oxide (10.3 g, 44.4 mmol). The suspension was stirred for 15 minutes and benzyl bromide (4.5 g, 26.3 mmol) was added. The mixture was stirred at the same temperature for 24 h and the insoluble materials were removed by filtration through a short pad of celite. The filtrate was concentrated under reduced pressure and the crude product chromatographed over a column of silica gel, eluting with 20% diethyl ether-petroleum ether to give 70, as a colorless liquid in 70% yield (2.8 g).

$^1$H NMR (500 MHz, CDCl$_3$) δ 7.39-7.29 (m, 5H), 4.62 (s, 2H), 4.16 (s, 2H), 3.78 (s, 3H).

2-Benzyloxy-acetic hydrazide (71). A mixture of 70 (2.75 g, 15.3 mmol) in methanol (50 mL) and hydrazine hydrate (65% in water, 2.3 g, 30 mmol) was heated under reflux for 3 h. The reaction mixture was concentrated under reduced pressure and the residue was diluted with benzene. The solvent was evaporated and the crude product was further dried under high vacuum (6 h) to give 71 (2.75 g), as a light yellow waxy material, which was used in the next step without further purification.

$^1$H NMR (500 MHz, CDCl$_3$) δ 7.72 (br s, 1H, NH), 7.39-7.29 (m, 5H), 4.56 (s, 2H), 4.07 (s, 2H), 3.82 (br s, 2H, NH$_2$).

2-Benzyloxymethyl-1,3,4-oxadiazole (72). To a mixture of 71, (2.7 g, 15 mmol) and trimethyl orthoformate (5 mL) was added p-TSA, (anhydrous, 255 mg, 1.5 mmol). The mixture was refluxed for 3 h and the excess trimethyl orthoformate evaporated under reduced pressure. The crude product was purified over a column of silica gel, eluting with 30% acetone-petroleum ether to give 72 as a colorless liquid (1.4 g), in 49% yield (two steps). $^1$H NMR (500 MHz, CDCl$_3$) δ 8.43 (s, 1H), 7.39-7.31 (m, 5H), 4.77 (s, 2H), 4.64 (s, 2H).

7-(Phenoxy)-1-(5-benzyloxymethyl-1,3,4-oxadiazol-2-yl)-heptan-1-one (73.1). The title compound was synthesized analogously to 73.2 (see experimental below), using 72 (190 mg, 1 mmol), n-BuLi (2.5 M solution in hexane, 0.4 mL, 1 mmol), MgBr$_2$.Et$_2$O (284 mg, 1.1 mmol) and 68.1 (132 mg, 0.5 mmol). The crude obtained after workup was chromatographed over a column of silica gel, eluting with 30% ethyl acetate-petroleum ether to give 73.1 as a white solid (m p 61-63° C.) in 53% yield (104 mg).

$^1$H NMR (500 MHz, CDCl$_3$) δ 7.38-7.32 (m, 5H), 7.27 (t, J=7.0 Hz, 2H), 6.92 (t, J=7.0 Hz, 1H), 6.90 (d, J=7.0 Hz, 2H), 4.77 (s, 2H), 4.68 (s, 2H), 3.95 (t, J=6.2 Hz, 2H), 3.16 (t, J=7.2 Hz, 2H), 1.86-1.76 (m, 4H), 1.56-1.43 (m, 4H).

7-(4-Benzyloxy-phenoxy)-1-(5-benzyloxymethyl-1,3,4-oxadiazol-2-yl)-heptan-1-one (73.2).

To a stirred solution of 72 (380 mg, 2 mmol) in anhydrous THF (40 mL), at −78° C., under an argon atmosphere, was added n-BuLi (2.5 M solution in hexane, 0.8 mL, 2 mmol) dropwise. Stirring was continued for 15 min at the same temperature, and then MgBr$_2$.Et$_2$O (568 mg, 2.2 mmol) was added. The mixture was warmed to −30° C. over a 2 hours period, and then a solution of 68.2 (370 mg, 1 mmol) in THF (10 mL) was added. The mixture was gradually warmed to 0° C. and maintained at the same temperature for 4 h. The reaction mixture was diluted with aqueous NH$_4$Cl solution (20 mL) and ethyl acetate (50 ml) and gradually warmed to room temperature. The organic layer was separated and the aqueous layer was extracted with ethyl acetate (2×20 mL). The combined organic layer was washed with brine (30 mL), dried over MgSO$_4$ and the solvent evaporated under reduced pressure. The crude product was chromatographed over a column of silica gel, eluting with 30% ethyl acetate-petroleum ether to give 73.2 as a white solid (m p 95-97° C.) in 55% yield (275 mg).

$^1$H NMR (500 MHz, CDCl$_3$) δ 7.42 (d, J=8.0 Hz, 2H), 7.40-7.34 (m, 6H), 7.28-7.33 (m, 2H), 6.90 (d, J=8.5 Hz, 2H), 6.81 (d, J=8.5 Hz, 2H), 5.01 (s, 2H), 4.77 (s, 2H), 4.68 (s, 2H), 3.90 (t, J=6.2 Hz, 2H), 3.16 (t, J=7.2 Hz, 2H), 1.86-1.74 (m, 4H), 1.54-1.44 (m, 4H).

1-(5-hydroxymethyl-1,3,4-oxadiazol-2-yl)-7-phenoxy-heptan-1-one (74.1). To a stirred suspension of 73.1 (80 mg, 0.2 mmol) and Pd/C (160 mg) in AcOH/MeOH (1:10 mixture, 5 mL) at 45° C. was added 1,4-cyclohexadiene (304 mg, 4 mmol) over a period of 30 min. The mixture was stirred for an additional 2 h at the same temperature. The catalyst was removed by filtration through celite and the filtrate was evaporated under reduced pressure. The residue was purified through a column of silica, eluting with 45% ethyl acetate in petroleum ether to give 74.1 as a white solid (m p 83-85° C.) in 25% yield (15 mg).

$^1$H NMR (400 MHz, CDCl$_3$) δ 7.27 (t, J=7.0 Hz, 2H), 6.92 (t, J=7.0 Hz, 1H), 6.90 (d, J=7.0 Hz, 2H), 4.88 (s, 2H), 3.95 (t, J=6.5 Hz, 2H), 3.16 (t, J=7.2 Hz, 2H), 2.56 (br s, 1H, OH), 1.88-1.74 (m, 4H), 1.59-1.44 (m, 4H).

1-(5-benzyloxymethyl-1,3,4-oxadiazol-2-yl)-7-(4-hydroxyphenoxy)-heptan-1-one (74.2).

A mixture of 73.2 (50 mg, 0.1 mmol) and Pd/C (10 mg) in AcOEt (5 mL) was stirred vigorously under hydrogen overnight at room temperature. The catalyst was removed by filtration through celite and the filtrate was evaporated under reduced pressure. The crude material was purified through a column of silica gel, eluting with 45% ethyl acetate-petroleum ether to give 74.2 as a white solid in 75% yield (31 mg).

$^1$H NMR (500 MHz, CDCl$_3$) δ 7.38-7.31 (m, 5H), 6.79-6.73 (m, 4H), 4.77 (s, 2H), 4.68 (s, 2H), 4.50 (br s, 1H, OH), 3.90 (t, J=6.2 Hz, 2H), 3.15 (t, J=7.2 Hz, 2H), 1.84-1.74 (m, 4H), 1.56-1.44 (m, 4H).

α-Keto-oxadiazoles 78 and 81 (shown in Scheme 15) were synthesized by a method depicted in Scheme 15 starting from commercially available 3-benzyloxybromobenzene (28) and 3-anisaldehyde (79).

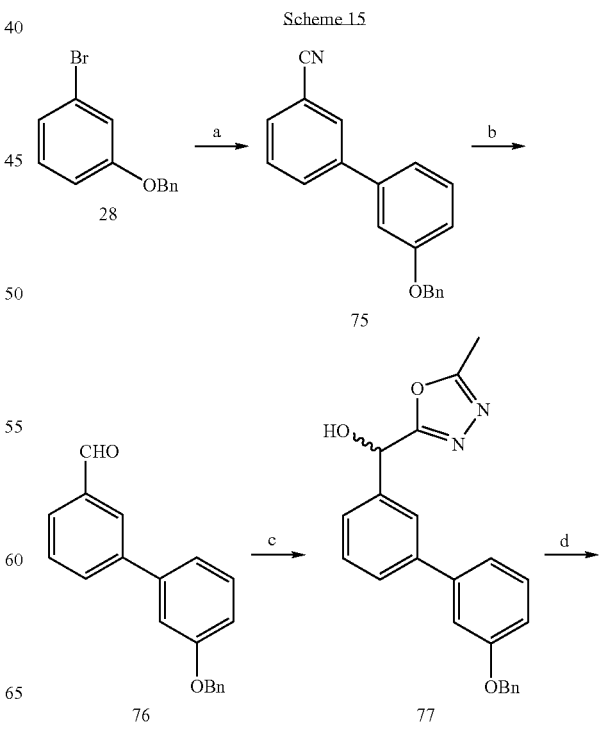

Scheme 15

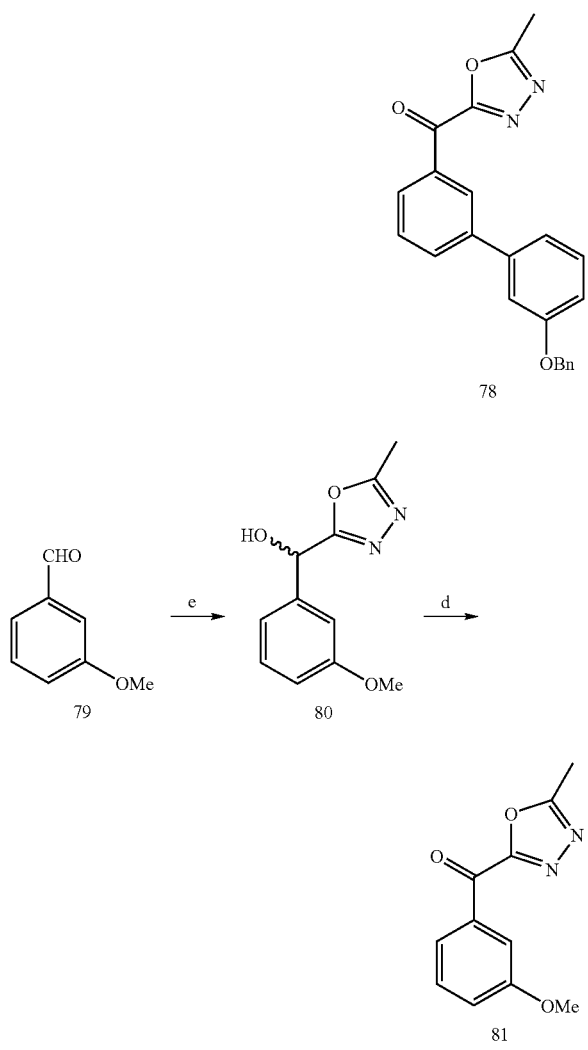

Reagents and conditions: (a) 3-cyanophenylboronic acid, Ba(OH)$_2$, Pd(PPh$_3$)$_4$, DME/H$_2$O, reflux, 6 h, 52%; (b) DIBAL-H, THF, −78° C., 1 h, 65%; (c) 63, n-BuLi, MgBr$_2$.Et$_2$O, THF −78° C. to −45° C., 2 h, then addition of 76, −78° C. to −45° C., 2 h, 59%; (d) Dess-Martin periodinane, CH$_2$Cl$_2$, 50° C., 2 h, 80-82%; (e) 63, n-BuLi, MgBr$_2$.Et$_2$O, THF, −78° C. to −50-C, 2 h, then addition of 79, −78° C., 2 h, 57%.

Experimental Procedures:

3-(3-Benzyloxy-phenyl)benzonitrile (75).

A degassed mixture of 3-benzyloxy-phenyl bromide (28) (0.2 g, 0.76 mmol), 3-cyanophenylboronic acid (0.223 g, 1.52 mmol), barium hydroxide (0.285 g, 1.67 mmol), Pd(PPh$_3$)$_4$ (0.088 g, 0.076 mmol), DME (5 mL) and H$_2$O (3 mL) was heated (80° C.) for 6 hours with vigorous stirring under an argon atmosphere. The reaction mixture was cooled to room temperature, diluted with ethyl acetate, and filtered through a plug of celite. The filtrate was diluted with brine; the organic phase was separated, dried (MgSO$_4$) and concentrated in vacuo. The residue obtained was purified by flash column chromatography (20% diethyl ether-hexane) to give 75 (0.130 g, 60% yield) as a viscous liquid.

$^1$H NMR (500 MHz, CDCl$_3$) δ 7.85 (t, J=2.5 Hz, 1H), 7.78 (dt, J=7.5 Hz, J=1.5 Hz, 1H), 7.63 (dt, J=8.0 Hz, J=1.5 Hz, 1H), 7.53 (t, J=8.0 Hz, 1H), 7.46 (d, J=7.5 Hz, 2H), 7.44-7.37 (m, 3H), 7.35 (t, J=7.0 Hz, 1H), 7.18-7.14 (m, 2H), 7.02 (dd, J=8.5 Hz, J=2.5 Hz, 1H), 5.17 (s, 2H).

3-(3-Benzyloxy-phenyl)benzaldehyde (76).

To a stirred solution of 75 (0.12 g, 0.42 mmol) in anhydrous THF (10 mL) at −78° C., under a nitrogen atmosphere was added diisobutylaluminum hydride (0.5 mL, 0-5 mmol, using a 1M solution in hexane) dropwise. The reaction mixture was stirred at the same temperature for 1 hour and then quenched by dropwise addition of potassium sodium tartrate (10% solution in water). The resulting mixture was warmed to room temperature, diluted with diethyl ether (20 mL) and stirred vigorously for 1 h. The organic phase was separated and the aqueous phase was extracted with diethyl ether. The combined organic layer was washed with brine, dried (MgSO$_4$) and evaporated under reduced pressure. The residue obtained was purified by flash column chromatography on silica gel (20% diethyl ether-hexane) to give 76 (0.091 g, 75% yield) as a viscous liquid.

$^1$H NMR (500 MHz, CDCl$_3$) δ 10.08 (s, 1H), 8.09 (t, J=1.5 Hz, 1H), 7.85 (dt, J=7.5 Hz, J=1.5 Hz, 2H), 7.60 (t, J=7.7 Hz, 1H), 7.47 (d, J=7.5 Hz, 2H), 7.44-7.32 (m, 3H), 7.35 (t, J=7.5 Hz, 1H), 7.27-7.21 (m, 2H), 7.02 (dd, J=7.7 Hz, J=2.0 Hz, 1H), 5.14 (s; 2H).

1-(3'-Benzyloxy-1,1'-biphenyl-3-yl)-1-(5-methyl-1,3,4-oxadiazol-2-yl)-methanol (77).

To a stirred solution of 63 (0.118 g, 1.5 mmol), in dry THF (5 mL), at −78° C., under a nitrogen atmosphere, was added n-BuLi (0.6 mL, 1.5 mmol, using a 2.5M solution in hexane) dropwise. Stirring continued for 10 min at −78° C. and then MgBr$_2$.Et$_2$O (0.4 g, 1.5 mmol) was added. The resulting mixture was warmed to −45° C. over a 2 hours period, and then it was cooled back to −78° C., and a solution of 76 (0.081 g, 0.28 mmol) in dry THF (5 mL) was added dropwise. Following the addition, the reaction mixture was warmed to −45° C. over a 2 hours period and then diluted with aqueous NH$_4$Cl solution (5 mL) and AcOEt (20 mL). The resulting mixture was gradually warmed to room temperature, the organic phase was separated and the aqueous phase extracted with AcOEt. The combined organic layer was washed with brine, dried (MgSO$_4$) and evaporated under reduced pressure. The residue obtained was purified by flash column chromatography on silica gel (75% ethyl acetate-hexane) to give 77 (0.052 g, 50% yield) as a colorless viscous liquid.

$^1$H NMR (500 MHz, CDCl$_3$) δ 7.69 (m as br s, 1H), 7.59-7.56 (m, 1H), 7.47-7.45 (m, 4H), 7.40 (t, J=7.0 Hz, 2H), 7.37-7.32 (m, 2H), 7.20 (t, J=2.0 Hz, 1H), 7.18 (d J=8.0 Hz, 1H), 6.98 (dd, J=8.5 Hz, J=2.0 Hz, 1H), 6.08 (s, 1H), 5.12 (s, 2H), 3.22 (br s, 1H), 2.45, (s, 3H).

1-(3'-Benzyloxy-1,1'-biphenyl-3-yl)-1-(5-methyl-1,3,4-oxadiazol-2-yl)-ketone (78).

To a solution of 77 (45 mg, 0.12 mmol) in wet CH$_2$Cl$_2$ (5 mL) at room temperature, under nitrogen, was added Dess-Martin periodinane (1022 mg, 0.24 mmol) and the resulting suspension stirred for 2 hours at 50° C. The reaction mixture was cooled to room temperature, diluted with Na$_2$S$_2$O$_3$ (10% in H$_2$O) and saturated aqueous NaHCO$_3$ solution, and the organic phase was separated. The aqueous layer was extracted with AcOEt and the combined organic layer was washed with brine, dried MgSO$_4$) and evaporated under reduced pressure. The residue obtained was purified by flash column chromatography on silica gel (60% ethyl acetate-hexane) to give 78 (35.52 mg, 80% yield) as a white solid (m p 97-99° C.).

$^1$H NMR (500 MHz, CDCl$_3$) δ 8.70 (t, J=2.0 Hz, 1H), 8.54 (d, J=8.0 Hz, 1H), 7.90 (d, J=8.0 Hz, 1H), 7.62 (t, J=8.0 Hz, 1H), 7.48 (d, J=7.5 Hz, 2H), 7.42-7.40 (m, 3H), 7.34 (t, J=7.5

Hz, 1H), 7.27-7.25 (m, 2H), 7.01 (dd, J=7.0 Hz, J=2.0 Hz, 1H), 5.15 (s, 2H), 2.71 (s, 3H).

1-(3-Methoxy-phenyl)-1-(5-methyl-1,3,4-oxadiazol-2-yl)-methanol (80). The synthesis was carried out analogous to the preparation of 77 using 79 (0.14 g, 1.03 mmol) and 63 (0.29 g, 3.45 mmol). Purification by flash column chromatography on silica gel gave compound 80 (0.12 g, 53.4% yield) as a viscous liquid.

$^1$H NMR (500 MHz, CDCl$_3$) δ 7.30 (t, J=7.5 Hz, 1H), 7.06-7.02 (m, 2H), 6.90 (dd, J=7.5 Hz, J=2.5 Hz, 1H), 6.05 (d, J=5.0 Hz, 1H), 3.83 (s, 3H), 3.67 (d, J=5.0 Hz, 1H), 2.49 (s, 3H).

1-(3-Methoxy-phenyl)-1-(5-methyl-1,3,4-oxadiazol-2-yl)-ketone (81) was synthesized as in 78 using 80 (0.1 g, 0.454 mmol) and Dess-Martin periodinane (0.38 g, 0.9 mmol) in wet CH$_2$Cl$_2$ (10 mL). Purification by flash column chromatography on silica gel gave compound 81 (0.080 g, 82% yield) as a viscous liquid.

$^1$H NMR (500 MHz, CDCl$_3$) δ 8.10 (dt, J=7.5 Hz, J=1.5 Hz, 1H), 7.99 (t, J=1.5 Hz, 1H), 7.47 (t, J=7.5 Hz, 1H), 7.24 (dd, J=7.5 Hz, J=1.5 Hz, 1H), 3.90 (s, 3H), 2.70 (s, 3H).

7. Synthesis of Saccharin Analogs.

Saccharin analogs 83.1, 83.2, 83.3, 83.4, 83.5, 83.6, 83.7, 83.8, 83.9 and 84 (shown in Scheme 16) were synthesized by a method depicted in Scheme 16 starting from commercially available saccharin (82) and the appropriate bromide.

Scheme 16

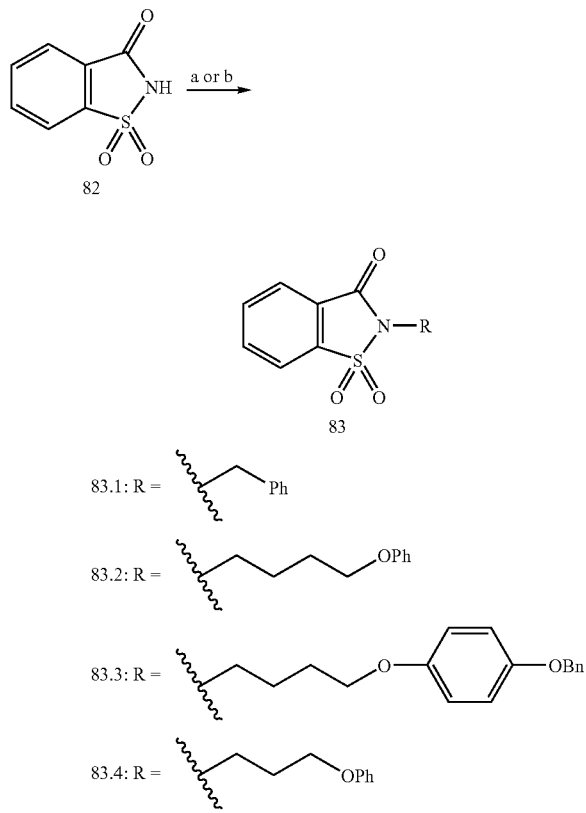

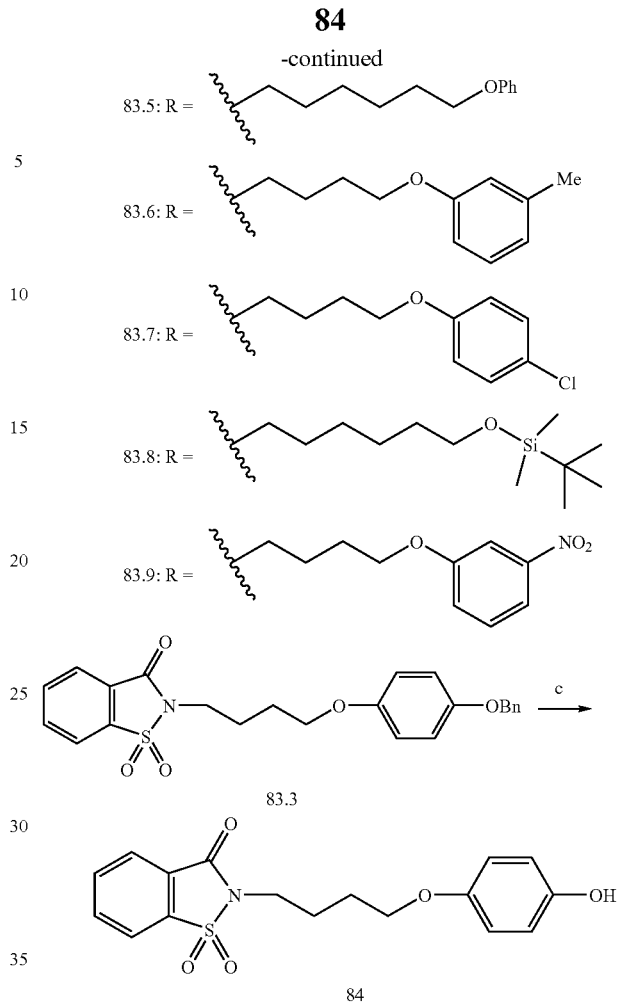

Reagents and conditions: (a) (i) NaH, THF, 0° C. to r t, 1 h, (ii) RBr, DMF, 80° C., 4 h, 66-67%; (b) (i) NaH, DMF, r t, 15 min, (ii) RBr, DMF, m.w, 150° C., 10 min, 45-65%; (c) 1,4-cyclohexadiene, Pd/C, EtOH, 50° C., 2 h, 56%.

Experimental Procedures:

N-(Phenylmethyl)saccharin (83.1).

To a stirred solution of saccharin 82 (0.154 g, 0.75 mmol) in anhydrous THF (10 mL) at 0° C., under nitrogen atmosphere was added NaH (0.019 g, 0.8 mmol, using a 60% dispersion in mineral oil) and the resulting slurry was gradually warmed to room temperature over 1 hour period. Solvent was removed under reduced pressure, and the saccharin sodium salt was dissolved in anhydrous DMF (5 mL). To this solution, was added a solution of benzyl bromide (0.051 g, 0.3 mmol) in DMF (5 mL), under nitrogen, at room temperature and the mixture warmed to 80° C. and stirred for 4 hours. The reaction mixture was cooled to room temperature and diluted with dropwise addition of water (5 mL) and AcOEt (20 mL). The organic layer was separated and the aqueous layer extracted with AcOEt. The combined organic layer was washed with brine, dried (MgSO$_4$) and the solvent removed in vacuo. The residue was purified by flash column chromatography on silica gel (50% diethyl ether-hexane) to give 83.1 (0.054 g, 66% yield), as a white solid (in p 106-108° C.).

$^1$H NMR (500 MHz, CDCl$_3$) δ 8.06 (d, J=7.0 Hz, 1H), 7.93 (d, J=7.0 Hz, 1H), 7.87 (td, J=7.0 Hz, J=1.2 Hz, 1H), 7.83 (td, J=7.0 Hz, J=1.2 Hz, 1H), 7.51 (d, J=7.5 Hz, 2H), 7.36 (t, J=7.5 Hz, 2H), 7.31 (t, J=7.0 Hz, 1H), 4.91 (s, 2H).

N-(4-Phenoxy-butyl)saccharin (83.2).

The synthesis was carried out analogous to the preparation of 83.1 using 82 (0.23 g, 1.25 mmol), NaH (0.030 g, 1.25 mmol) and 4-phenoxy-butyl bromide (0.115 g, 0.5 mmol) in DMF (5 mL). Purification by flash column chromatography on silica gel gave 83.2 (0.1 g, 67% yield) as a white solid (m p 92-94° C.).

$^1$H NMR (500 MHz, CDCl$_3$) δ 8.07 (d, J=7.0 Hz, 1H), 7.93 (d, J=7.0 Hz, 1H), 7.87 (td, J=7.0 Hz, J=1.2 Hz, 1H), 7.83 (td, J=7.0 Hz, J=1.2 Hz, 1H), 7.27 (t, J=7.5 Hz, 2H), 6.93 (t, J=7.5 Hz, 1H), 6.90 (d, J=7.5 Hz, 2H), 4.02 (t, J=6.5 Hz, 2H), 3.88 (t, J=7.2 Hz, 2H), 2.07 (quintet, J=6.9 Hz, 2H), 1.92 (quintet, J=6.9 Hz, 2H).

N-[4-(4-Benzyloxy-phenoxy)-butyl]saccharin (83.3).

The synthesis was carried out analogous to the preparation of 83.1 using 82 (0.307 g, 1.5 mmol), NaH (0.036 g, 1.5 mmol) and 4-(4-benzyloxy-phenoxy)-butyl bromide (0.2 g, 0.6 mmol) in DMF (5 mL). Purification by flash column chromatography on silica gel gave 83.3 (0.150 g, 66% yield) as a white solid (m p 82-84° C.).

$^1$H NMR (500 MHz, CDCl$_3$) δ 8.06 (d, J=7.0 Hz, 1H), 7.92 (d, J=7.0 Hz, 1H), 7.87 (td, J=7.0 Hz, J=1.2 Hz, 1H), 7.83 (td, J=7.0 Hz, J=1.2 Hz, 1H), 7.42 (d, J=7.5 Hz, 2H), 7.37 (t, J=7.5 Hz, 2H), 7.31 (t, J=7.5 Hz, 1H), 6.89 (d, J=9.0 Hz; 2H), 6.82 (d, J=9.0 Hz, 2H), 5.00 (s, 2H), 3.97 (t, J=6.4 Hz, 2H), 3.86 (t, J=7.2 Hz, 2H), 2.05 (quintet, J=6.9 Hz, 2H), 1.89 (quintet, J=6.9 Hz, 2H).

N-(3-Phenoxypropyl)saccharin (83.4). The title compound was synthesized analogously to 83.8 (see experimental below), using a solution of saccharin (92 mg, 0.5 mmol) in DMF (anhydrous, 4 mL), NaH (60% dispersion in mineral oil, 21 mg, 0.52 mmol) and a solution of 3-phenoxypropyl bromide (130 mg, 0.6 mmol) in anhydrous DMF (1 mL). The crude obtained after workup was purified by flash column chromatography on silica gel (25% ethyl acetate-petroleum ether) to give 83.4 as a white solid (m p 83-86° C.) in 65% yield (130 mg). $^1$H NMR (500 MHz, CDCl$_3$) δ 8.08 (dd, J=7.5 Hz, J=1.5 Hz, 1H), 7.95 (dd, J=7.5 Hz, J=1.5 Hz 1H), 7.89 (td, J=7.5 Hz, J=1.5 Hz, 1H), 7.85 (td, J=7.5 Hz, J=31.5 Hz, 1H), 7.30 (t, J=8.0 Hz, 2H), 6.97 (t, J=8.0 Hz, 1H), 6.93 (d, J=8.0 Hz, 2H), 4.11 (t, J=6.2 Hz, 2H), 4.04 (t, J=7.1 Hz, 2H), 2.36 (quintet, J=7.5 Hz, 2H).

N-(6-Phenoxyhexyl)saccharin (83.5). The title compound was synthesized analogously to 83.8 (see experimental below), using a solution of saccharin (92 mg, 0.5 mmol) in anhydrous DMF (, 4 mL), NaH (60% dispersion in mineral oil, 21 mg, 0.52 mmol), and a solution of 6-phenoxybutyl bromide (154 mg, 0.6 mmol) in DMF (anhydrous, 1 mL). The crude product obtained after workup was purified by flash column chromatography on silica gel (20% ethyl acetate-petroleum ether) to give 83.5 as a white solid (m p 64-66° C.) in 50% yield (90 mg). $^1$H NMR (500 MHz, CDCl$_3$) δ 8.07 (dd, J=7.5 Hz, J=1.5 Hz, 1H), 7.93 (dd, J=7.5 Hz, J=1.5 Hz 1H), 7.88 (td, J=7.5 Hz, J=1.5 Hz, 1H), 7.84 (td, J=7.5 Hz, J=1.5 Hz, 1H), 7.28 (t, J=7.5 Hz, 2H), 6.94 (t, J=7.5 Hz, 1H), 6.90 (d, J=7.5 Hz, 2H), 3.98 (t, J=6.5 Hz, 2H), 3.81 (t, J=7.5 Hz, 2H), 1.91 (quintet, J=7.2 Hz, 2H), 1.83 (quintet, J=7.2 Hz, 2H), 1.61-1.48 (m, 4H).

N-[4-(3-Methyl-phenoxy)-butyl]saccharin (83.6). The title compound was synthesized analogously to 83.8 (see experimental below), using a solution of saccharin (92 mg, 0.5 mmol) in anhydrous DMF (4 mL), NaH (60% dispersion in mineral oil, 21 mg, 0.52 mmol) and a solution of 1-(4-bromobutoxy)-3-methylbenzene (146 mg, 0.6 mmol) in DMF (anhydrous, 1 mL). The crude product obtained after workup was purified by flash column chromatography on silica gel (25% ethyl acetate-petroleum ether) to give 83.6 as a viscous liquid in 55% yield (95 mg).

$^1$H NMR (500 MHz, CDCl$_3$) δ 8.08 (dd, J=7.5 Hz, J=1.5 Hz, 1H), 7.94 (dd, J=7.5 Hz, J=1.5 Hz 1H), 7.88 (td, J=7.5 Hz, J=1.5 Hz, 1H), 7.85 (td, J=7.5 Hz, J=1.5 Hz, 1H), 7.17 (t, J=7.2 Hz, 1H), 6.77 (dd, J=7.2 Hz, 1.5 Hz, 1H), 6.74 (t, J=1.5 Hz, 1H), 6.72 (dd, J=7.2 Hz, J=1.5 Hz, 1H), 4.03 (t, J=6.5 Hz, 2H), 3.89 (t, J=7.5 Hz, 2H), 2.34 (s, 3H), 2.08 (quintet, J=7.5 Hz, 2H), 1.92 (quintet, J=7.0 Hz, 2H).

N-[4-(4-Chloro-phenoxy)-butyl]saccharin (83.7).

The title compound was synthesized analogously to 83.8 (see experimental below), using a solution of saccharin (92 mg, 0.5 mmol) in anhydrous DMF (4 mL), NaH (60% dispersion in mineral oil, 21 mg, 0.52 mmol) and a solution of 1-(4-bromobutoxy)-4-chlorobenzene (158 mg, 0.6 mmol) in anhydrous DMF (1 mL). The crude product obtained after workup was purified by flash column chromatography on silica gel (25% ethyl acetate-petroleum ether) to give 83.7 as a white solid (m p 85-88° C.) in 57% yield (104 mg).

$^1$H NMR (500 MHz, CDCl$_3$) δ 8.08 (d, J=7.2 Hz, 1H), 7.94 (d, J=7.2 Hz, 1H), 7.89 (td, J=7.2 Hz, J=1.2 Hz, 1H), 7.85 (td, J=7.2 Hz, J=1.2 Hz, 1H), 7.23 (d, J=8.7 Hz, 2H), 6.84 (d, J=8.7 Hz, 2H), 4.01 (t, J=6.2 Hz, 2H), 3.89 (t, J=7.5 Hz, 2H), 2.07 (quintet, J=7.5 Hz, 2H), 1.92 (quintet, J=8.2 Hz, 2H).

N-(6-tert-Butyldimethylsilyloxy-hexyl)saccharin (83.8). To a solution of saccharin (92 mg, 0.5 mmol) in anhydrous DMF (4 mL), at room temperature, under a nitrogen atmosphere, was added NaH (60% dispersion in mineral oil, 21 mg, 0.52 mmol). The mixture was stirred at the same temperature for additional 15 min, a solution of (6-bromohexyloxy)-tert-butyldimethylsilane (177 mg, 0.6 mmol) in DMF (1 mL) was added and the resulting mixture microwaved at 150° C. for 10 min. The reaction mixture was cooled to room temperature and diluted with water (5 mL) and AcOEt (10 mL). The organic layer was separated and the aqueous layer extracted with AcOEt (2×10 mL). The combined organic layer was washed with brine, dried (MgSO$_4$) and the solvent removed in vacuum. The residue was purified by flash column chromatography on silica gel (20% ethyl acetate-petroleum ether) to give 83.8 (89 mg, 45% yield), as a viscous liquid.

$^1$H NMR (400 MHz, CDCl$_3$) δ 8.07 (dd, J=7.4 Hz, J=1.5 Hz, 1H), 7.93 (dd, J=7.4 Hz, J=1.5 Hz 1H), 7.88 (td, J=7.4 Hz, J=1.5 Hz, 1H), 7.84 (td, J=7.4 Hz, J=1.5 Hz, 1H), 3.79 (t, J=7.5 Hz, 2H), 3.62 (t, J=6.4 Hz, 2H), 1.88 (quintet, J=7.3 Hz, 2H), 1.55 (quintet, J=6.7 Hz, 2H), 1.50-1.34 (m, 4H), 0.91 (s, 9H), 0.07 (s, 6H).

N-[4-(3-Nitro-phenoxy)-butyl]saccharin (83.9).

The title compound was synthesized analogously to 83.8, using a solution of saccharin (92 mg, 0.5 mmol) in anhydrous DMF (4 mL), NaH (60% dispersion in mineral oil, 21 mg, 0.52 mmol) and a solution of 1-(4-bromobutoxy)-3-nitrobenzene (164 mg, 0.6 mmol) in anhydrous. DMF (1 mL). The crude product obtained after workup was purified by flash column chromatography on silica gel (25% ethyl acetate-petroleum ether) to give 83.9 as a white solid (m p 87-89° C.) in 55% yield (95 mg).

$^1$H NMR (500 MHz, CDCl$_3$) δ 8.09 (dd; J=7.2 Hz, J=1.5 Hz, 1H), 7.95 (dd, J=7.2 Hz, J=1.5 Hz 1H), 7.90 (td, J=7.2 Hz, J=1.5 Hz, 1H), 7.86 (td, J=7.2 Hz, J=1.5 Hz, 1H), 7.83 (dd, J=8.0 Hz, J=1.8 Hz, 1H), 7.74 (t, J=1.8 Hz, 1H), 7.43 (t, J=8.0 Hz, 1H), 7.24 (dd, J=8.0 Hz, J=1.8 Hz, 1H), 4.12 (t, J=6.2 Hz, 2H), 3.91 (t, J=7.0 Hz, 2H), 2.10 (quintet, J=7.5 Hz, 2H), 1.98 (quintet, J=7.2 Hz, 2H).

N-[4-(4-Hydroxy-phenoxy)-butyl]saccharin (84).

To a stirred solution of 83.3 (0.1 g, 0.23 mmol) in EtOH (5 mL) was added 10% Pd/C (0.1 g, 100% w/w) and 1,4-cyclohexadiene (92 mg, 1.15 mmol) and the resulting suspension was stirred vigorously at 50° C. for 2 hours. The reaction mixture was cooled to room temperature, the catalyst was removed by filtration through Celite, and the filtrate was evaporated under reduced pressure. The residue was purified by flash column chromatography on silica gel (60% diethyl ether-hexane) to give 84 (0.044 g, 56% yield) as a white solid (m p 107-109° C.). $^1$H NMR (500 MHz, CDCl$_3$) δ 8.06 (d, J=7.0 Hz, 1H), 7.92 (d, J=7.0 Hz, 1H), 7.87 (td, J=7.0 Hz, J=1.2 Hz, 1H), 7.83 (td, J=7.0 Hz, J=1.2 Hz, 1H), 6.79 (d, J=9.0 Hz, 2H), 6.74 (d, J=9.0 Hz, 2H), 4.38 (br s, 1H), 3.96 (t, J=6.4 Hz, 2H), 3.89 (t, J=7.2 Hz, 2H), 2.05 (quintet, J=6.9 Hz, 2H), 1.89 (quintet, J=6.9 Hz, 2H).

8. Synthesis of α-Keto-Esters and α,α-Difluoromethylene-Ketones.

α-Keto-esters 87.1-4 and 87.7 (shown in Scheme 17) as well as α,α-difluoromethylene-ketones 89.1, 89.2, 89.4, and 89.7-14 (shown in Scheme 17) were synthesized by the methods depicted in Scheme 17. 3-Benzyloxyphenyl (85.1), 4-benzyloxyphenyl (85.5), 2-benzyloxyphenyl (85.6), 4-phenoxybutyl bromide (86.2), 5-phenoxypentyl bromide (86.4), 6-phenoxyhexyl bromide (86.7), 3-methyl-phenyl magnesium bromide, 2-bromopyridine, and 3-bromopyridine were commercially available materials. The 2-methyl-oxadiazole (63), 2-bromopyridine, and 3-bromopyridine were served as precursors for the preparation of the respective organolithium reagent using commercially available n-BuLi.

Scheme 17

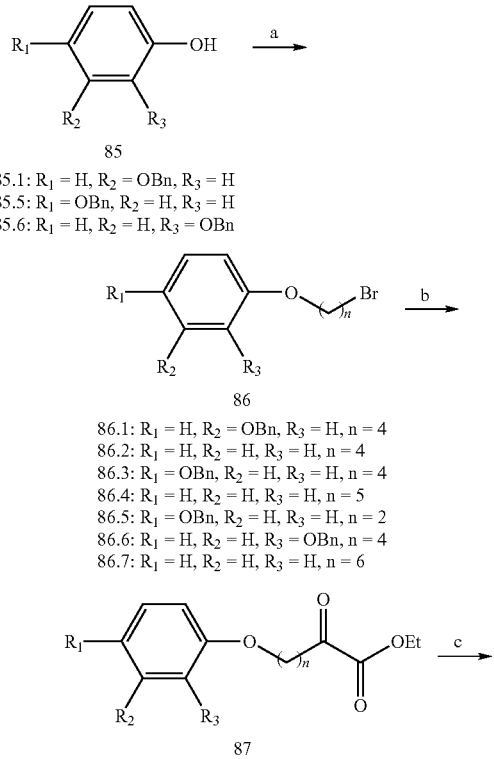

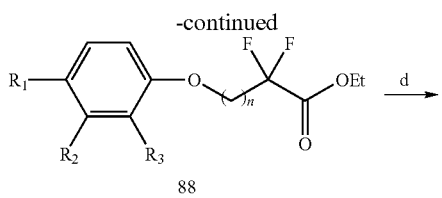

88.1: R$_1$ = H, R$_2$ = OBn, R$_3$ = H, n = 4
88.2: R$_1$ = H, R$_2$ = H, R$_3$ = H, n = 4
88.4: R$_1$ = H, R$_2$ = H, R$_3$ = H, n = 5
88.7: R$_1$ = H, R$_2$ = H, R$_3$ = H, n = 6

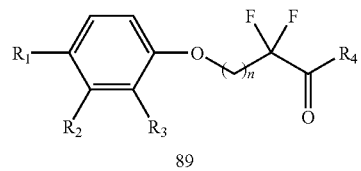

89.1: R$_1$ = H, R$_2$ = OBn, R$_3$ = H, R$_4$ = Me, n = 4
89.2: R$_1$ = H, R$_2$ = H, R$_3$ = H, R$_4$ = Me, n = 4
89.4: R$_1$ = H, R$_2$ = H, R$_3$ = H, R$_4$ = Me, n = 5

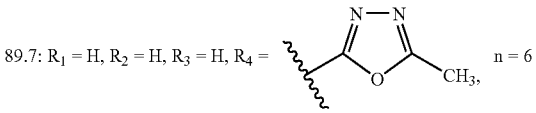

89.7: R$_1$ = H, R$_2$ = H, R$_3$ = H, R$_4$ =

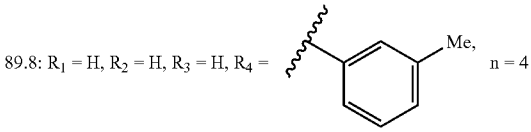

89.8: R$_1$ = H, R$_2$ = H, R$_3$ = H, R$_4$ =

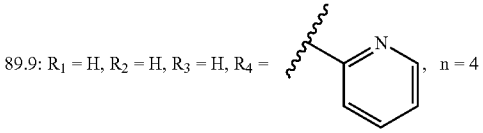

89.9: R$_1$ = H, R$_2$ = H, R$_3$ = H, R$_4$ =

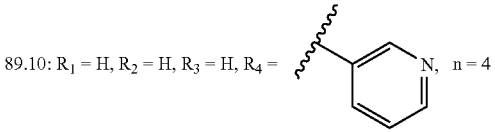

89.10: R$_1$ = H, R$_2$ = H, R$_3$ = H, R$_4$ =

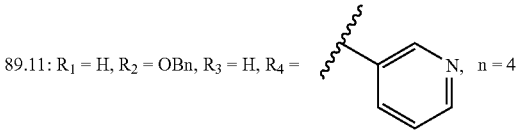

89.11: R$_1$ = H, R$_2$ = OBn, R$_3$ = H, R$_4$ =

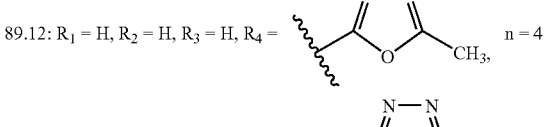

89.12: R$_1$ = H, R$_2$ = H, R$_3$ = H, R$_4$ =

89.13: R$_1$ = H, R$_2$ = OBn, R$_3$ = H, R$_4$ =

89.14: R$_1$ = H, R$_2$ = OBn, R$_3$ = H, R$_4$ =

Reagents and conditions: (a) Br—(CH$_2$)$_n$—Br, K$_2$CO$_3$, acetone or MeCN, reflux, 10-12 h, 68-74% for n=4, 5, 6 or NaH, DMF, r t to 80° C., 6 h, 64% for n=2; (b) Mg, THF, r t to gentle reflux, then addition to (COOEt)$_2$, THF, −78° C. to 10° C., 1 h, 45-65%; (c) DAST, CHCl$_3$, reflux, 3 h, 72-88% or DAST CHCl$_3$, m.w, 100° C., 300 W, 3-5 min, 74-86%, (d) R$_4$Li, THF or Et$_2$O, −78° C. to r t, 1-2 h, 65-78%.

Experimental Procedures:

Bromides (86).

A mixture of phenol derivative 85 (1 equiv.), α,ω-dibromoalkane (1.5 equiv.) and anhydrous potassium carbonate was stirred under refluxed in dry acetone or acetonitrile for 10-12 hours, then it was cooled to room temperature and solid materials were filtered off. The filtrate was evaporated, water was added to the residue and the mixture was extracted with diethyl ether. The ethereal layer was washed with 10% sodium hydroxide solution, water and brine, dried (MgSO$_4$) and concentrated under reduced pressure. Purification by flash column chromatography on silica gel (diethyl ether-hexane) gave compound 86 as colorless viscous oil in 68-74% yields.

For the synthesis of bromide 86.5 the following procedure was used.

A mixture of 4-benzyloxy-phenol 85.5 (1 equiv.) and NaH in anhydrous dimethylformamide was stirred at room temperature for 15 min under argon. To this mixture was added 1,2-dibromoethane (1.5 equiv.) and stirring was continued at 80° C. for 6 hours. The reaction mixture was cooled to room temperature, diluted with water and extracted with diethyl ether. The ethereal layer was washed with water and brine, dried (MgSO$_4$) and concentrated under reduced pressure. Purification by flash column chromatography on silica gel (diethyl ether-hexane) gave product 86.5 in 64% yield.

Selected Data of Synthesized Bromides (86)

1-Bromo-4-[3-(benzyloxy)phenoxy]butane (86.1).

$^1$H NMR (500 MHz, CDCl$_3$) δ 7.43 (d, J=7.6 Hz, 2H), 7.39 (t, J=7.6 Hz, 2H), 7.32 (t, J=7.6 Hz, 1H), 7.17 (t, J=8.5 Hz, 1H), 6.58 (dd, J=8.5 Hz, J=2.5 Hz, 1H), 6.54 (t, J=2.5 Hz, 1H), 6.50 (dd, J=8.5 Hz, J=2.5 Hz, 1H), 5.04 (s, 2H), 3.97 (t, J=6.3 Hz, 2H), 3.48 (t, J=6.5 Hz, 2H), 2.06 (m, 2H), 1.93 (m, 2H).

1-Bromo-2-[4-(benzyloxy)phenoxy]ethane (86.5).

$^1$H NMR (500 MHz, CDCl$_3$) δ 7.43 (d, J=7.3 Hz, 2H), 7.38 (t, J=7.3 Hz, 2H), 7.32 (t, J=7.3 Hz, 1H), 6.92 (d, J=8.5 Hz, 2H), 6.85 (d, J=8.5 Hz, 2H), 5.07 (s, 2H), 4.24 (t, J=6.5 Hz, 2H), 3.61 (t, J=6.5 Hz, 2H).

α-Keto-esters (87).

To a three-neck round bottom flask containing Mg turnings (1.2 equiv.) equipped with a magnetic stirrer and dimroth condenser was added a solution of alkyl bromide 86 (1 equiv.) in anhydrous THF via syringe and external heating under argon atmosphere. The reaction mixture was refluxed gently for 30-40 min. and then it was cooled to room temperature, before conveying it to a dropping funnel. The Grignard reagent was added dropwise to a solution of diethyl oxalate (1.5 equiv.) in THF at −78° C. The reaction mixture was warmed to 10° C. within 1 hour and then was quenched by the addition of saturated ammonium chloride solution. The organic layer was separated, the aqueous layer was extracted with diethyl ether and the combined organic layer was washed with brine, dried over MgSO$_4$ and evaporated. The residue was purified by flash column chromatography on silica gel (diethyl ether-hexane) to give pure compound 87 in 45-65% yields.

Selected Data of Synthesized α-Keto-esters (87).

2-Oxo-6-[4-(benzyloxy)phenoxy]hexanoic acid ethyl ester (87.3).

$^1$H NMR (500 MHz, CDCl$_3$) δ 7.44 (d, J=7.5 Hz, 2H), 7.40 (t, J=7.5 Hz, 2H), 7.34 (t, J=7.5 Hz, 1H), 6.91 (d, J=9.0 Hz, 2H), 6.83 (d, J=9.0 Hz, 2H), 5.03 (s, 2H), 4.33 (q, J=7.5 Hz, 2H), 3.94 (t, J=5.8 Hz, 2H), 2.95 (t, J=7.0 Hz, 2H); 1.90-1.79 (m, 4H); 1.38 (t, J=7.5 Hz, 3H).

2-Oxo-7-phenoxy-heptanoic acid ethyl ester (87.4).

$^1$H NMR (500 MHz, CDCl$_3$) δ 7.27 (t, J=7.6 Hz, 2H), 6.93 (t, J=7.6 Hz, 1H), 6.88 (d, J=7.6 Hz, 2H), 4.32 (q, J=7.5 Hz, 2H), 3.96 (t, J=6.0 Hz, 2H), 2.88 (t, J=7.5 Hz, 2H), 1.81 (qt, J=6.5 Hz, 2H), 1.72 (qt, J=7.5 Hz, 2H), 1.56-1.49 (m, 2H), 1.37 (t, J=7.5 Hz, 3H).

α,α-Difluoro-esters (88).

To a stirred solution of α-keto-ester 87 (1 equiv.) in anhydrous chloroform at room temperature under an argon atmosphere was added diethylaminosulfur trifluoride (1.1 equiv.). The reaction mixture was heated under gentle reflux for 3 hours then it was cooled to room temperature and poured into ice-water. The organic layer was separated, washed with sat. NaHCO$_3$ solution and dried over MgSO$_4$. Volatiles were removed under reduced pressure and the crude product was purified by flash chromatography on silica gel (diethyl ether-hexane) to give pure compound 88 in 72-88% yields.

Alternatively, the reaction mixture was heated using microwave irradiation (300 W, 100° C., 3-5 min.). This was followed by work up and purification as described above to give compound 88 in 74-86% yields.

Selected Data of Synthesized α,α-difluoro-esters (88)

2,2-Difluoro-6-[3-(benzyloxy)phenoxy]hexanoic acid ethyl ester (88.1).

$^1$H NMR (500 MHz, CDCl$_3$) δ 7.43 (d, J=7.5 Hz, 2H), 7.38 (t, J=7.5 Hz, 2H), 7.32 (t, J=7.5 Hz, 1H), 7.17 (t, J=8.5 Hz, 1H), 6.57 (dd, J=8.5 Hz, J=2.5 Hz, 1H), 6.53 (t, J=2.5 Hz, 1H), 6.50 (dd, J=8.5 Hz, J=2.5 Hz, 1H), 5.04 (s, 2H), 4.32 (q, J=7.4 Hz, 2H), 3.94 (t, J=6.5 Hz, 2H), 2.19-2.08 (m, 2H), 1.82 (qt, J=7.9 Hz, 2H), 1.71-1.63 (m, 2H), 1.34 (t, J=7.4 Hz, 3H).

α,α-difluoromethylene-ketones (89).

To a stirred solution of α,α-difluoro-ester 88 (1 equiv.) in anhydrous THF or diethyl ether at −78° C. under an argon atmosphere was added the appropriate organolithium or organomagnesium reagent (1.1-1.5 equiv.) dropwise. The reaction mixture was allowed to warm to room temperature over 1-2 hours period and then it was quenched by the addition of saturated ammonium chloride solution. The organic phase was separated, the aqueous layer was extracted with diethyl ether or methylene chloride and the combined organic layer was washed with water and brine, dried (MgSO$_4$) and evaporated under reduced pressure. Purification by flash column chromatography on silica gel (diethyl ether-hexane or acetone-hexane) gave compound 89 in 65-78% yields.

Selected Data of Synthesized α,α-difluoromethylene-ketones (89).

3,3-difluoro-8-phenoxy-2-octanone (89.4).

$^1$H NMR (500 MHz, CDCl$_3$) δ 7.28 (m as t, J=7.5 Hz, 2H), 6.93 (m as t, J=7.5 Hz, 1H), 6.89 (m as d, J=7.5 Hz, 2H), 3.96 (t, J=6.3 Hz, 2H), 2.33 (t, J=1.5 Hz, 3H), 2.06-1.95 (m, 2H), 1.83-1.77 (m, 2H), 1.56-1.51 (m, 4H).

2,2-Difluoro-8-phenoxy-1-(5-methyl-1,3,4-oxadiazol-2-yl)-octan-1-one (89.7, mixture of keto and hydrate form in a 2.2:1 ratio).

$^1$H NMR (500 MHz, CDCl$_3$) δ 7.28 (t, J=7.2 Hz, 2H, keto form), 7.27 (t, J=7.2 Hz, 2H, hydrate form), 6.93 (t, J=7.2 Hz, 1H from keto form and 1H from hydrate form, overlapping), 6.89 (d, J=7.2 Hz, 2H, hydrate form), 6.88 (d, J=7.2 Hz, 2H, keto form), 4.46 (br s, 2H, OH, hydrate form), 3.95 (t, J=6.5 Hz, 2H, hydrate form), 3.94 (t, J=6.5 Hz, 2H, keto form), 2.70 (s, 3H, keto form), 2.60 (s, 3H, hydrate form), 2.44-2.32 (m, 2H, keto form), 2.16-2.00 (m, 2H, hydrate form), 1.82-1.74 (m, 2H from keto form and 2H from hydrate form, overlapping), 1.64-1.40 (m, 6H from keto form and 6H from hydrate form, overlapping); IR (neat) 3237 (br), 2942, 2866, 1734, 1600 cm$^{-1}$.

2,2-Difluoro-6-phenoxy-1-(pyridin-2-yl)-hexan-1-one (89.9).

$^1$H NMR (500 MHz, CDCl$_3$) δ 8.65 (m as dt, J=6.1 Hz, J=0.5 Hz, 1H), 8.03 (m as dt, J=8.0 Hz, J=1.0 Hz, 1H), 7.81 (ddd, J=8.0 Hz, J=8.0 Hz, J=1.7 Hz, 1H), 7.44 (ddd, J=8.0 Hz, J=6.1 Hz, J=1.7 Hz, 1H), 7.19 (t, J=7.8 Hz, 2H), 6.85 (t, J=7.8 Hz, 1H), 6.78 (d, J=7.8 Hz, 2H), 3.95 (t, J=6.5 Hz, 2H), 2.60-2.43 (m, 2H), 1.73 (qt, J=7.3 Hz, 2H), 1.67-1.62 (m, 2H).

2,2-Difluoro-6-phenoxy-1-(pyridin-3-yl)-hexan-1-one (89.10, hydrate form).

$^1$H NMR (500 MHz, DMSO-d$_6$) δ 8.70 (d, J=1.5 Hz, 1H), 8.53 (dd, J=5.2 Hz, J=1.5 Hz, 1H), 7.88 (dt, J=7.6 Hz, J=1.4 Hz, 1H), 7.39 (dd, J=7.6 Hz, J=5.2 Hz, 1H), 7.27 (t, J=7.4 Hz, 2H), 7.03 (s, 2H), 6.94-6.88 (m, 3H), 3.95 (t, J=6.2 Hz, 2H), 2.12-1.99 (m, 2M), 1.74 (qt, J=7.1 Hz, 2H), 1.61-1.53 (m, 2H).

2,2-Difluoro-6-[3-(benzyloxy)phenoxy]-1-(pyridin-3-yl)-hexan-1-one (89.11, hydrate form).

$^1$H NMR (500 MHz, CD$_3$OD) δ 8.68 (d, J=1.7 Hz, 1H), 8.52 (dd, J=5.1 Hz, J=1.7 Hz, 1H), 7.98 (dt, J=8.0 Hz, J=1.4 Hz, 1H), 7.46 (dd, J=8.0 Hz, J=5.1 Hz, 1H), 7.42 (d, J=7.4 Hz, 2H), 7.36 (t, J=7.4 Hz, 2H), 7.29 (t, J=7.4 Hz, 1H), 7.13 (t, J=8.2 Hz, 1H), 6.55 (dd, J=8.2 Hz, J=2.5 Hz, 1H), 6.51 (t, J=2.5 Hz, 1H), 6.47 (dd, J=8.2 Hz, J=2.5 Hz, 1H), 5.04 (s, 2H), 3.92 (t, J=6.5 Hz, 2H), 2.02 (m, 2H), 1.76 (qt, J=7.2 Hz, 2H), 1.64 (qt, J=7.3 Hz, 2H).

α-Keto-esters 91.1-6 (shown in Scheme 18) as well as α,α-difluoromethylene-ketones 93.1, 93.2, 93.5, and 93.7-9 (shown in Scheme 18) were synthesized by the methods depicted in Scheme 18. 4-Bromobiphenyl (90.1), bromobenzene (90.2), 3-bromobiphenyl (90.3), 2-bromobiphenyl (90.4), benzoxazole, benzothiazole, 2,6-dibromopyridine, and 2-(4-bromophenyl)pyridine were commercially available materials. The 2-methyl-oxadiazole (63), benzoxazole, benzothiazole, 2,6-dibromopyridine, and 2-(4-bromophenyl)pyridine were served as precursors for the preparation of the respective organolithium agents using commercially available n-BuLi.

Scheme 18

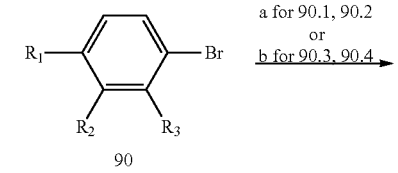

90
90.1: R$_1$ = Ph, R$_2$ = H, R$_3$ = H
90.2: R$_1$ = H, R$_2$ = H, R$_3$ = H
90.3: R$_1$ = H, R$_2$ = Ph, R$_3$ = H
90.4: R$_1$ = H, R$_2$ = H, R$_3$ = Ph

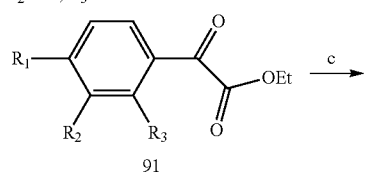

91
91.1: R$_1$ = Ph, R$_2$ = H, R$_3$ = H
91.2: R$_1$ = H, R$_2$ = H, R$_3$ = H
91.3: R$_1$ = H, R$_2$ = Ph, R$_3$ = H
91.4: R$_1$ = H, R$_2$ = H, R$_3$ = Ph
91.5: R$_1$ = Br, R$_2$ = H, R$_3$ = H
91.6: R$_1$ = H, R$_2$ = Me, R$_3$ = H

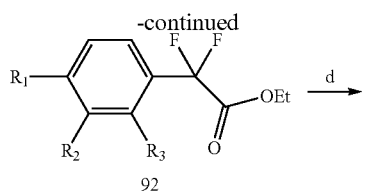

92
92.1: R$_1$ = Ph, R$_2$ = H, R$_3$ = H
92.2: R$_1$ = H, R$_2$ = H, R$_3$ = H
92.3: R$_1$ = H, R$_2$ = Ph, R$_3$ = H
92.4: R$_1$ = H, R$_2$ = H, R$_3$ = Ph
92.5: R$_1$ = Br, R$_2$ = H, R$_3$ = H

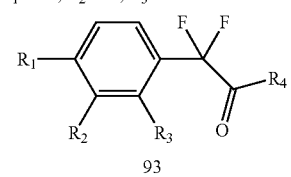

93

93.1: R$_1$ = Ph, R$_2$ = H, R$_3$ = H, R$_4$ = 2-methyl-1,3,4-oxadiazol-5-yl 93.2: R$_1$ = H, R$_2$ = H, R$_3$ = H, R$_4$ = benzoxazol-2-yl 93.5: R$_1$ = Br, R$_2$ = H, R$_3$ = H, R$_4$ = 2-methyl-1,3,4-oxadiazol-5-yl 93.7: R$_1$ = Ph, R$_2$ = H, R$_3$ = H, R$_4$ = 6-bromopyridin-2-yl 93.8: R$_1$ = H, R$_2$ = H, R$_3$ = H, R$_4$ = benzothiazol-2-yl 93.9: R$_1$ = H, R$_2$ = H, R$_3$ = H, R$_4$ = 4-(pyridin-2-yl)phenyl Reagents and conditions: (a) Mg, THF, reflux, then addition to (COOEt)$_2$, THF, −78° C. to 10-C, 1 h, 55-65%; (b) n-BuLi, THF, −78° C., 15 min, then addition to (COOEt)$_2$, THF, −78° C. to 0° C., 1 h, 58-68%; (c) DAST CHCl$_3$, m.w, 100° C., 300 W, 3-5 min, 78-86%, (d) R$_4$Li, THF or Et$_2$O, −78° C. to r t, 1-2 h, 68-80%.

Experimental Procedures:

α-Keto-esters (91).

To a three-neck round bottom flask containing Mg turnings (1.2 equiv.) equipped with a magnetic stirrer and dimroth condenser was added a solution of alkyl bromide 90 (1 equiv.) in anhydrous THF via syringe and external heating under argon atmosphere. The reaction mixture was refluxed gently for 30-40 min. and then it was cooled to room temperature, before conveying it to a dropping funnel. The Grignard reagent was added dropwise to a solution of diethyl oxalate (1.5 equiv.) in THF at −78° C. The reaction mixture was warmed to 10° C. within 1 hour and then was quenched by the addition of saturated ammonium chloride solution. The organic layer was separated, the aqueous layer was extracted with diethyl ether and the combined organic layer was washed with brine, dried over $MgSO_4$ and evaporated. The residue was purified by flash column chromatography on silica gel (diethyl ether-hexane) to give pure compound 91 in 55-65% yields.

Selected Data of Synthesized α-Keto-esters (91)
Ethyl 2-(biphenyl-4-yl)-2-oxoacetate (91.1).
$^1$H NMR (500 MHz, $CDCl_3$) δ 8.09 (d, J=8.5 Hz, 2H), 7.74 (d, J=8.5 Hz, 2H), 7.65 (d, J=7.2 Hz, 2H), 7.49 (t, J=7.2 Hz, 2H), 7.43 (t, J=7.2 Hz, 1H), 4.47 (q, J=7.5 Hz, 2H), 1.45 (t, J=7.5 Hz, 3H).

Ethyl 2-(4-bromophenyl)-2-oxoacetate (91.5)
$^1$H NMR (500 MHz, $CDCl_3$) δ 7.92 (d, J=8.5 Hz, 2H), 7.68 (d, J=8.5 Hz, 2H), 3.98 (s, 3H).

α,α-Difluoro-esters (92).
To a solution of α-keto-ester 91 (1 equiv.) in anhydrous chloroform at room temperature was added diethylaminosulfur trifluoride (1.1 equiv.) and the reaction mixture was heated using microwave irradiation (300 W, 100° C.) for 3-5 min. The reaction mixture was cooled to room temperature and poured into ice-water. The organic layer was separated, washed with sat. $NaHCO_3$ solution and dried over $MgSO_4$. Volatiles were removed under reduced pressure and the crude product was purified by flash chromatography on silica gel (diethyl ether-hexane) to give pure compound 92 in 78-86% yields.

Selected Data of Synthesized α,α-difluoro-esters (92)
Ethyl 2-(biphenyl-4-yl)-2,2-difluoroacetate (92.1).
$^1$H NMR (500 MHz, $CDCl_3$) δ 7.68 (d, J=9.0 Hz, half of AA'BB'system, 2H), 7.66 (d, J=9.0 Hz, half of AA'BB' system, 2H), 7.58 (d, J=7.5 Hz, 2H), 7.46 (t, J=7.5 Hz, 2H), 7.39 (t, J=7.5 Hz, 1H), 4.32 (q, J=7.6 Hz, 2H), 1.33 (t, J=7.6 Hz, 3H).

Ethyl 2,2-difluoro-2-phenylacetate (92.2).
$^1$H NMR (500 MHz, $CDCl_3$) δ 7.62 (d, J=7.0 Hz, 2H), 7.50-7.43 (m, 3H), 4.29 (q, J=7.0 Hz, 2H), 1.29 (t, J=7.0 Hz, 3H).

Ethyl 2-(biphenyl-3-yl)-2,2-difluoroacetate (92.3).
$^1$H NMR (500 MHz, $CDCl_3$) δ 7.83 (br s, 1H), 7.72 (d, J=7.0 Hz, 1H), 7.58-7.61 (m, 3H), 7.53 (t, J=7.5 Hz, 1H), 7.47 (t, J=7.5 Hz, 2H), 7.39 (t, J=7.5 Hz, 1H), 4.32 (q, J=7.5 Hz, 2H), 1.32 (t, J=7.5 Hz, 3H).

Ethyl 2-(4-bromophenyl)-2,2-difluoroacetate (92.5).
$^1$H NMR (500 MHz, $CDCl_3$) δ 7.61 (d, J=8.0 Hz, 2H), 7.49 (d, J=8.0 Hz, 2H), 3.85 (s, 3H).

α,α-difluoromethylene-ketones (93).
To a stirred solution of α,α-difluoro-ester 92 (1 equiv.) in anhydrous THF or diethyl ether at −78° C. under an argon atmosphere was added the appropriate organolithium reagent (1.1 equiv.) dropwise. The reaction mixture was allowed to warm to room temperature over 1-2 hours period and then it was quenched by the addition of saturated ammonium chloride solution. The organic phase was separated, the aqueous layer was extracted with diethyl ether or methylene chloride and the combined organic layer was washed with water and brine, dried ($MgSO_4$), and evaporated under reduced pressure. Purification by flash column chromatography on silica gel (diethyl ether-hexane or acetone-hexane) gave compound (89) in 68-80% yields.

Selected Data of Synthesized α,α-difluoromethylene-ketones (93)
2-(Biphenyl-4-yl)-2,2-difluoro-1-(5-methyl-1,3,4-oxadiazol-2-yl)ethanone (93.1).
$^1$H NMR (500 MHz, acetone-$d_6$) δ 7.73 (d, J=8.5 Hz, 1H), 7.71 (d, J=8.0 Hz, 1H), 7.68 (d, J=8.5 Hz, 1H), 7.50 (t, J=8.0 Hz, 2H), 7.41 (t, J=8.0 Hz, 1H), 2.54 (s, 3H).

2-(4-Bromophenyl)-2,2-difluoro-1-(5-methyl-1,3,4-oxadiazol-2-yl)ethanone (93.5).
$^1$H NMR (500 MHz, acetone-$d_6$) δ 7.65 (d, J=8.0 Hz, 2H), 7.55 (d, J=8.0 Hz, 2H), 2.54 (s, 3H).

2-(Biphenyl-4-yl)-1-(6-bromopyridin-2-yl)-2,2-difluoroethanone (93.7).
$^1$H NMR (500 MHz, $CDCl_3$) δ 8.03 (dd, J=7.7 Hz, J=1.2 Hz, 1H), 7.87 (d, J=8.2 Hz, 2H), 7.69 (t, J=7.7 Hz, 1H), 7.67 (d, J=8.2 Hz, 2H), 7.63 (dd, J=7.7 Hz, J=1.2 Hz, 1H), 7.59 (d, J=7.5 Hz, 2H), 7.45 (t, J=7.5 Hz, 2H), 7.37 (t, J=7.5 Hz, 1H).

α,α-difluoromethylene-ketones 96.1 and 96.2 (shown in Scheme 19) were synthesized by the method depicted in Scheme 19 using commercially available ethyl bromodifluoroacetate, 6-phenoxyhexyl bromide, and 4-bromobiphenyl.

Scheme 19

Reagents and conditions: (a) 2-bromopyridine, Cu, DMSO; 50° C., 2 h, 82%; (b) RMgBr, THF, −78° C. to 10° C., 1 h, 50-67%.

Experimental Procedures:
Ethyl 2-(2-pyridyl)-2,2-difluoroacetate (95).
To a solution of ethyl bromodifluoroacetate (1.1 equiv.) and 2-bromopyridine (1 equiv.) in DMSO was added copper bronze (2.2 equiv.) and the mixture was heated to 50° C. with stirring for 2 hours. The reaction mixture was cooled to room temperature and diluted with ethyl acetate. A solution of potassium dihydrogen phosphate was added and the mixture stirred for 30 minutes before filtering. The copper salts were washed with ethyl acetate and the organic layer was washed with water. Solvent evaporation and purification by flash column chromatography on silica gel (diethyl ether-hexane) gave the title compound as a colorless oil in 82% yield.

Compound (96).
To a three-neck round bottom flask containing Mg turnings (1.2 equiv.) equipped with a magnetic stirrer and condenser was added a solution of the appropriate bromide (1 equiv.) in dry THF via syringe. The reaction mixture was refluxed gently for 30-40 minutes, cooled to room temperature and it was transferred to the addition funnel. The Grignard reagent was added dropwise to a solution of ethyl 2-(2-pyridyl)-2,2-difluoroacetate (1 equiv.) in THF at −78° C. The reaction mixture was warmed to 10° C. within 1 hour and then quenched by the addition of saturated ammonium chloride solution. The organic layer was separated, the aqueous layer was extracted with diethyl ether and the combined organic layer was washed with brine, dried over MgSO$_4$ and evaporated. The residue was purified by flash column chromatography on silica gel (diethyl ether-hexane) to give pure compound 96 in 50-67% yield.

Selected Data of Synthesized α,α-difluoromethylene-ketones (96).

1,1-Difluoro-8-phenoxy-1-(pyridin-2-yl)octan-2-one (96.1).

$^1$H NMR (500 MHz, CDCl$_3$) δ 8.62 (d, J=5.0 Hz, 1H), 7.84 (t, J=7.5 Hz, 1H), 7.71 (d, J=5.0 Hz, 1H), 7.40 (dd, J=7.5 Hz, J=5.0 Hz, 1H), 7.27 (t, J=8.3 Hz, 2H), 6.93 (t, J=8.3 Hz, 1H), 6.87 (d, J=8.3 Hz, 2H), 3.94 (t, J=6.5 Hz, 2H), 2.86 (t, J=7.5 Hz, 2H), 1.77 (qt, J=7.5 Hz, 2H), 1.70 (qt, J=7.0 Hz, 2H), 1.48 (qt, J=7.0 Hz, 2H), 1.39 (qt, J=7.4 Hz, 2H).

1 (Biphenyl-4-yl)-2,2-difluoro-2-(pyridin-2-yl)ethanone (96.2)

$^1$H NMR (500 MHz, CDCl$_3$) δ 8.63 (d, J=4.5 Hz, 1H), 8.13 (d, J=8.5 Hz, 2H), 7.91 (td, J=7.5 Hz, J=1.5 Hz, 1H), 7.86 (d, J=8.5 Hz, 1H), 7.65 (d, J=8.5 Hz, 2H), 7.60 (d, J=7.5 Hz, 2H), 7.46 (t, J=7.5 Hz, 2H), 7.38-7.43 (m, 2H).

IR (neat)=3060, 1707, 1273, 1146, 906.

Some of the compounds included in this disclosure were isolated in their hydrate form or as mixtures of the keto and the hydrate form. A method for converting the hydrate to the keto form is given below.

A solution of the hydrate form or mixture of hydrate/keto forms in an anhydrous solvent (for example benzene) was stirred at room temperature in the presence of a drying agent (for example molecular sieves) for approximately 0.5-4 hours under an argon atmosphere. The drying agent was removed by filtration and the filtrate was evaporated to give the keto form quantitatively. Alternatively, the hydrate form or the mixture of hydrate/keto forms was dried under high vacuum in the presence of a drying agent (for example P$_2$O$_5$) to give the keto form.

What is claimed is:

1. A compound of formula R—X—Y, or any pharmaceutically acceptable salt thereof including all stereoisomers, wherein:

Y is selected from the following structures:

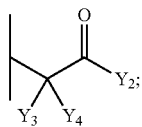

Y$_2$ is selected from -aryl-alkyl-Y$_{14}$, -heteroaryl, -heteroaryl-alkyl, -heteroaryl-alkyl-Y$_{14}$, -cycloalkyl, -heterocyclic, —C$_{1-5}$-alkyl-Y$_{14}$, -aryl-Y$_{14}$, -heteroaryl-Y$_{14}$;

Y$_3$ and Y$_4$ are each F;

Y$_{14}$ is selected from —OH, SH, —N$_3$, —NCS, —CONH$_2$, —SO$_2$NH$_2$, —COOH, —COOMe, —NO$_2$, —SO$_3$H, —P(O)(OH)$_2$;

X is selected from —(CH$_2$)$_n$— and —(CH$_2$)$_j$-A-(CH$_2$)$_k$—;

A is selected from O and NH;

n is an integer from 0 to about 15;

j is an integer from 0 to about 10;

k is an integer from 1 to about 10;

R is selected from the following structures:

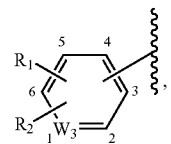

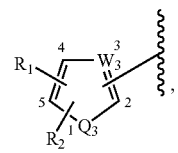

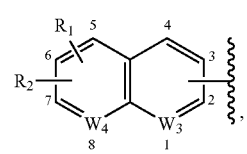

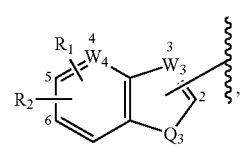

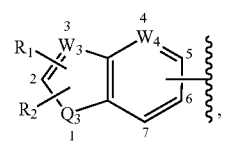

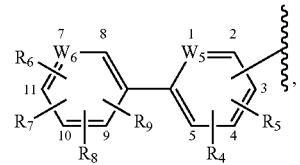

wherein:

W$_3$ is selected from CH and N if W$_3$ is not bonded to X or R1 or R2, or W$_3$ is C if W$_3$ is bonded to X or R1 or R2, and if W$_3$ is N then it can occupy any position selected from 1, 2, 3, 4, 5 and 6 in I 8; 2, 3, 4 and 5 in I 9; 1, 2, 3 and 4 in I 10; 2 and 3 in I 11, I 12;

W$_4$ is selected from CH and N if W$_4$ is not bonded to X or R1 or R2, or W$_4$ is C if W$_4$ is bonded to X or R1 or R2, and if W$_4$ is N then it can occupy any position selected from 5, 6, 7 and 8 in I 10; 4, 5, 6 and 7 in I 11, I 12;

W$_5$ is selected from CH and N if W$_5$ is not bonded to X or R4 or R5, or W$_5$ is C if W$_5$ is bonded to X or R4 or R5 and if W$_5$ is N then it can occupy any position selected from 1, 2, 3, 4, and 5 in I 16;

W$_6$ is selected from CH and N if W$_6$ is not bonded to R6 or R7 or R8 or R9, or W$_6$ is C if W$_6$ is bonded to R6 or R7 or R8 or R9, and if W$_6$ is N then it can occupy any position selected from 7, 8, 9, 10, and 11 in I 16;

Q$_3$ is selected from CH$_2$, O, S and NH if Q$_3$ is not bonded to X or R1 or R2, or Q$_3$ is selected from CH and N if Q$_3$ is bonded to X or R1 or R2;

R1 and R2 are each independently selected from —H, —F, —Cl, —Br, —I, —OH, —SH, —NH₂, —CN, —N₃, —NCS, —CONH₂, —SO₂NH₂, —COOH, —NO₂, —CHO, —CF₃, —SO₃H, —O—P(O)(OH)₂, -alkyl-R₃, -aryl-R₃, -heteroaryl-R₃, -Z-alkyl-R₃, -Z-aryl-R₃, -Z-heteroaryl-R₃, -Z-alkyl-aryl-R₃, -Z-alkyl-heteroaryl-R₃, —N(alkyl-R₃)₂, —C(O)N(alkyl-R₃)₂ and —SO₂N(alkyl-R₃)₂;

Z is selected from —O, —S, —NH;

R₃ is selected from —H, —F, —Cl, —Br, —I, -Me, -Et, —OH, —OAc, —SH, —NH₂, —CN, —N₃, —NCS, —CONH₂, —SO₂NH₂, —COOH, —NO₂, —CHO, —CF₃;

R4, R5, R6, R7, R8 and R9 are each independently selected from —H, —F, —Cl, —Br, —I, —OH, —OMe, —OEt, —OCH₂OCH₃, —OAc, —SH, —SMe, —SEt, —NH₂, —CN, —N₃, —NCS, —CONH₂, —SO₂NH₂, —COOH, —NO₂, —CHO, —CF₃, -alkyl, -alkyl-R₃.

2. The compound of claim 1 selected from:

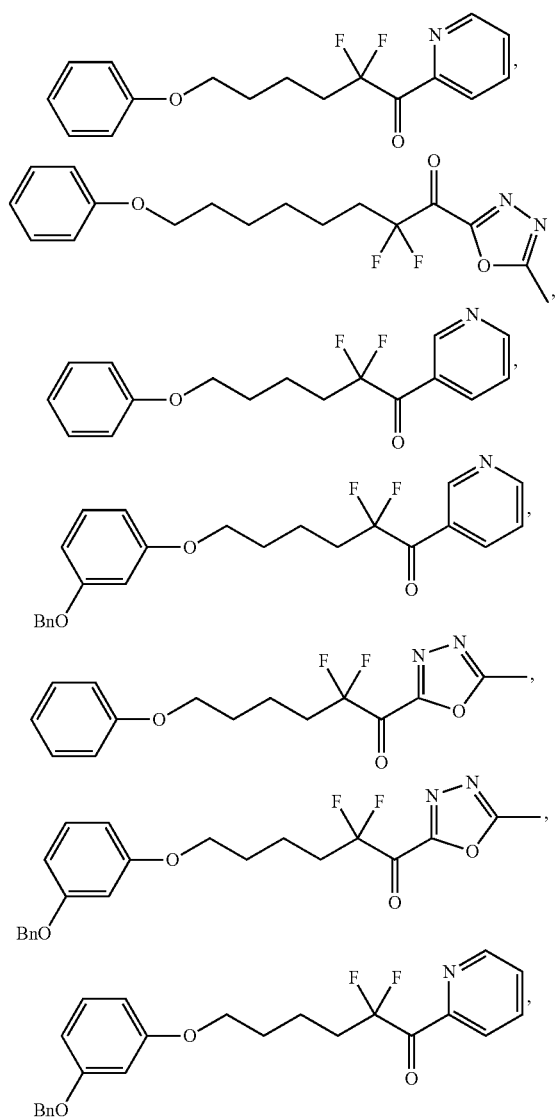

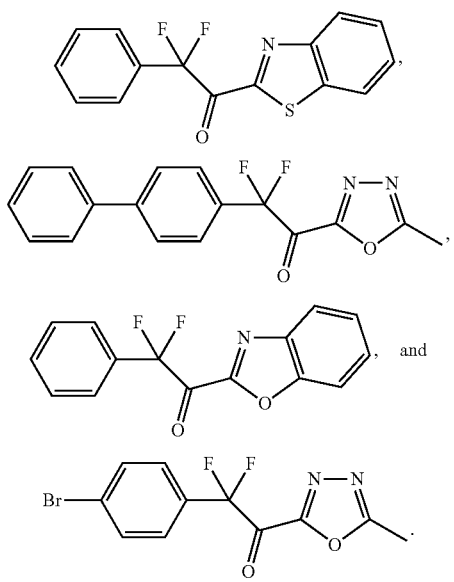

3. A medicament comprising a physiologically acceptable excipient and a therapeutically effective amount of a compound of formula R—X—Y, or any pharmaceutically acceptable salt thereof including all stereoisomers, the compound being in isolated and purified form, wherein:

Y is selected from the following structures:

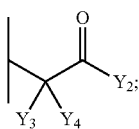

$Y_2$ is selected from -aryl-alkyl-$Y_{14}$, -heteroaryl, -heteroaryl-alkyl, -heteroaryl-alkyl-$Y_{14}$, -cycloalkyl, -heterocyclic, —$C_{1-5}$-alkyl-$Y_{14}$, -aryl-$Y_{14}$, -heteroaryl-$Y_{14}$;

$Y_3$ and $Y_4$ are each F;

$Y_{14}$ is selected from —OH, SH, —N₃, —NCS, —CONH₂, —SO₂NH₂, —COOH, —COOMe, —NO₂, —SO₃H, —P(O)(OH)₂;

X is selected from —(CH₂)ₙ— and —(CH₂)ⱼ-A-(CH₂)ₖ—;

A is selected from O and NH;

n is an integer from 0 to about 15;

j is an integer from 0 to about 10;

k is an integer from 0 to about 10;

R is selected from the following structures:

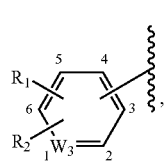

-continued

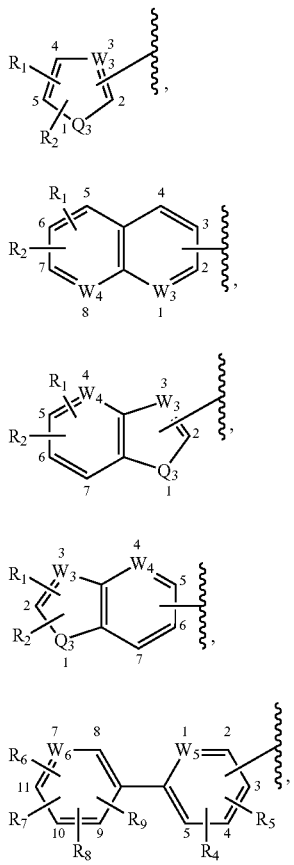

wherein:
- W$_3$ is selected from CH and N if W$_3$ is not bonded to X or R1 or R2, or W$_3$ is C if W$_3$ is bonded to X or R1 or R2, and if W$_3$ is N then it can occupy any position selected from 1, 2, 3, 4, 5 and 6 in I 8; 2, 3, 4 and 5 in I 9; 1, 2, 3 and 4 in I 10; 2 and 3 in I11, I 12;
- W$_4$ is selected from CH and N if W$_4$ is not bonded to X or R1 or R2, or W$_4$ is C if W$_4$ is bonded to X or R1 or R2, and if W$_4$ is N then it can occupy any position selected from 5, 6, 7 and 8 in I 10; 4, 5, 6 and 7 in I 11, I 12;
- W$_5$ is selected from CH and N if W$_5$ is not bonded to X or R4 or R5, or W$_5$ is C if W$_5$ is bonded to X or R4 or R5 and if W$_5$ is N then it can occupy any position selected from 1, 2, 3, 4, and 5 in I 16;
- W$_6$ is selected from CH and N if W$_6$ is not bonded to R6 or R7 or R8 or R9, or W$_6$ is C if W$_6$ is bonded to R6 or R7 or R8 or R9, and if W$_6$ is N then it can occupy any position selected from 7, 8, 9, 10, and 11 in I 16;
- Q3 is selected from CH$_2$, O, S and NH if Q$_3$ is not bonded to X or R1 or R2, or Q$_3$ is selected from CH and N if Q$_3$ is bonded to X or R1 or R2;
- R1 and R2 are each independently selected from —H, —F, —Cl, —Br, —I, —OH, —SH, —NH$_2$, —CN, —N$_3$, —NCS, —CONH$_2$, —SO$_2$NH$_2$, —COOH, —NO$_2$, —CHO, —CF$_3$, —SO$_3$H, —O—P(O)(OH)$_2$, -alkyl-R$_3$, -aryl-R$_3$, -heteroaryl-R$_3$, -Z-alkyl-R$_3$, -Z-aryl-R$_3$, -Z-heteroaryl-R$_3$, -Z-alkyl-aryl-R$_3$, -Z-alkyl-heteroaryl-R$_3$, —N(alkyl-R$_3$)$_2$, —C(O)N(alkyl-R$_3$)$_2$ and —SO$_2$N(alkyl-R$_3$)$_2$;
- Z is selected from —O, —S, —NH;
- R$_3$ is selected from —H, —F, —Cl, —Br, —I, -Me, -Et, —OH, —OAc, —SH, —NH$_2$, —CN, —N$_3$, —NCS, —CONH$_2$, —SO$_2$NH$_2$, —COOH, —NO$_2$, —CHO, —CF$_3$;
- R4, R5, R6, R7, R8 and R9 are each independently selected from —H, —F, —Cl, —Br, —I, —OH, —OMe, -OEt, —OCH$_2$OCH$_3$, —OAc, —SH, —SMe, —SEt, —NH$_2$, —CN, —N$_3$, —NCS, —CONH$_2$, —SO$_2$NH$_2$, —COOH, —NO$_2$, —CHO, —CF$_3$, -alkyl, -alkyl-R$_3$.

4. The medicament of claim 3, further comprising at least one material selected from a vehicle, a diluent, a carrier, an adjuvant, a flavoring, a colorant, a wetting agent, an emulsifying agent, a pH buffering agent and a preservative.

5. The medicament of claim 3, wherein the compound is selected from:

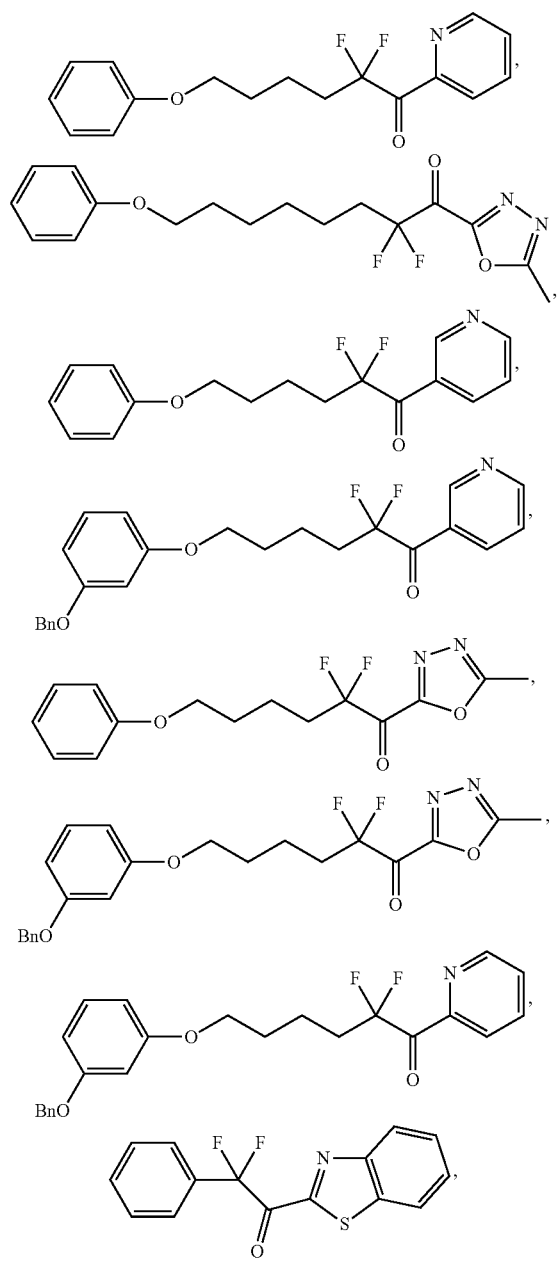

101
-continued
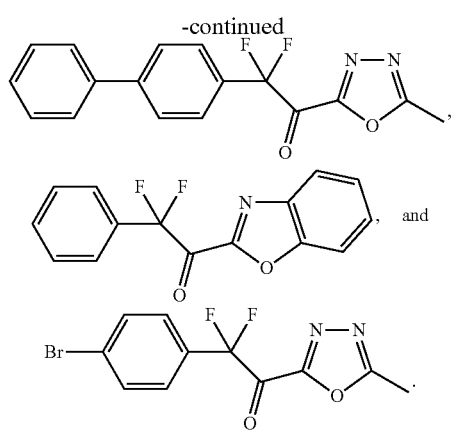
6. A compound selected from:
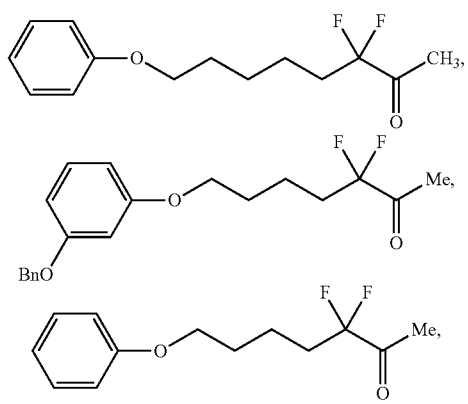
102
-continued
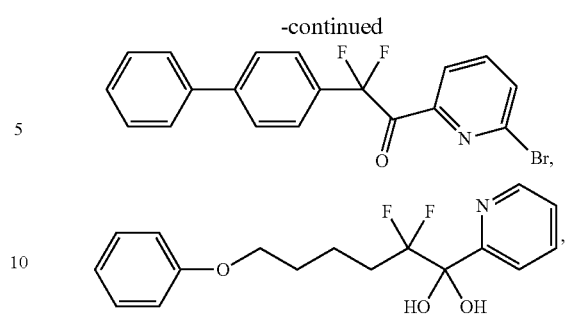
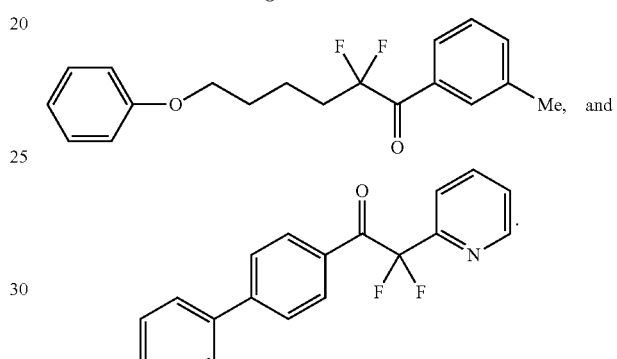
* * * * *